United States Patent [19]

Smith

[11] Patent Number: 4,851,425

[45] Date of Patent: Jul. 25, 1989

[54] CYCLOPENTAPYRAZOLE AND TETRAHYDROINDAZOLE COMPOUNDS AND THEIR USE AS ANTI-INFLAMMATORY AND ANTI-ALLERGIC AGENTS

[75] Inventor: Herman W. Smith, Kalamazoo, Mich.

[73] Assignee: The Upjohn Company, Kalamazoo, Mich.

[21] Appl. No.: 14,768

[22] PCT Filed: Jun. 3, 1986

[86] PCT No.: PCT/US86/01233

§ 371 Date: Feb. 3, 1987

§ 102(e) Date: Feb. 3, 1987

[87] PCT Pub. No.: WO86/07357

PCT Pub. Date: Dec. 18, 1986

[51] Int. Cl.$^4$ ............... A61K 31/415; C07D 231/56; C07D 401/06
[52] U.S. Cl. ............................ 514/406; 514/322; 546/199; 548/369
[58] Field of Search ............ 548/369; 514/406, 322; 546/199

[56] References Cited

FOREIGN PATENT DOCUMENTS 1948793 4/1971 Fed. Rep. of Germany ...... 548/369
2630015 1/1977 Fed. Rep. of Germany ...... 548/369

*Primary Examiner*—Mary C. Lee
*Assistant Examiner*—J. Richter
*Attorney, Agent, or Firm*—Donald L. Corneglio; Martha A. Cox

[57] ABSTRACT

The present invention provides novel compositions of matter and their therapeutic applications. More particularly, the present invention consists of novel cyclopentapyrazole and tetrahydroindazole compounds of formula XXX and their use as antiallergy agents, antiinflammatory agents or intermediates.

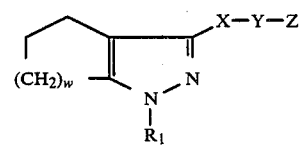

20 Claims, No Drawings

CYCLOPENTAPYRAZOLE AND TETRAHYDROINDAZOLE COMPOUNDS AND THEIR USE AS ANTI-INFLAMMATORY AND ANTI-ALLERGIC AGENTS

FIELD OF INVENTION

This invention relates to novel cyclopentapyrazole and tetrahydroindazole compounds and to the use of those compounds as anti-asthmatic agents, antiinflammatory agents or intermediates.

Structurally, the compounds of this invention are composed of a 1,3 substituted pyrazole ring additionally substituted at the four and five positions by a saturated cyclic ring of 5 or 6 carbon atoms.

INFORMATION DISCLOSURE

M. Nagakura et al., J. Med. Chem. 22: (No. 1), 48–52 (1979) describes 1-(2-)-aryl-4,5,6,7-tetrahydro-1H-indazole-5-carboxylic acid derivatives which demonstrated antiinflammatory activity in the carragenan edema test.

R. Fusco et al., Gazz. Chim. Ital. 91:1233–49 (1961) Chemical Abstract 2209C, 1962 describes the synthesis of 1-aryl-3-substituted-4,5,6,7-tetrahydroindazoles wherein the 3-substituent is e.g., a carboxy, carboxy ester or acetyl group.

M. Suzuki et al., Tetrahedron Letters 23: (No. 46), 4817–4820 (1982) describes the synthesis of a cyclopentapyrazole, referred to as a pyrazole prostacyclin.

R. Scuri, Boll. Chim. Farm., 109: (11), 674–81 (1970); Chemical Abstracts 75:3806b, describes 4,5-cyclomethylenepyrazoles (cyclopentapyrazoles and tetrahydroindazoles) having utility as spasmolytics, analgesics, antiinflammatories, antipyretics and CNS activities.

S. Nagai et al., Chem. Pharm. Bull., 27:1764–1770 (1979) describes the synthesis of (4S,7R)-7,8,8-trimethyl-1-phenyl-4,5,6,7-tetrahydro-1H-indazole-3-carboxylic acid and the corresponding 1-(4-methylphenyl) compound; (4S,7R)-7,8,8-trimethyl-1-phenyl-4,5,6,7-tetrahydro-4,7-methano-1H-indazole-3-methanol and (4S,7R)-7,8,8-trimethyl-1-phenyl-4,5,6,7-tetrahydro-4,7-methano-1H-indazole-3-ol.

G. G. Massaroli et al., Boll. Chim. Farm., 107(10), 613–28 (1968); CA 70:77861j, describe the synthesis of 1-aryl-3-acyl-4,5-cyclomethylenepyrazoles.

Polymethylene pyrazole derivatives having analgesic and antiinflammatory activities are described in W. German Pat. No. 2,630,015.

Tetrahydroindazoles having utility as intermediates and corrosion inhibitors are described in W. German Pat. No. 1,948,793.

N-Aryl-tetrahydroindazole derivatives having utility as antiinflammatory agents are described in Japan No. 5 0095-262.

1-Phenyl-4,5,6,7-tetrahydroindazole derivatives having antiphlogistic, analgesic, and antipyretic activities are described in Japan No. 5 4141-768.

1-Phenyl-5-acyloxymethylindazole derivatives having antiinflammatory, antipyretic, analgesic and antithrombotic activity are described in Japan No. 5 5019-226.

Pharmaceutically active cyclopentapyrazole derivatives having blood platelet aggregation inhibitory and antiinflammatory activity are described in Japan No. 5 7165-369.

1- or 2-Substituted-tetrahydro-2(H)-indazole-5-carboxylic acids having antiinflammatory, sedative and antipyretic activities are described in Belgium No. 806,805.

1-Arylpolymethylene-$C_{10}$-$C_{13}$-pyrazoles having antiinflammatory and antialgae activities are described in U.S. Pat. No. 3,364,227.

Dialkylamino-4,5,6,7-tetrahydroindazole derivatives having dopamine potentiating and prolactic secretion inhibiting activities are described in Belgium No. 877,330.

4,5,6,7-Tetrahydro-1H(or 2H) indazole compounds having utility in treating Parkinsonism are described in U.S. Pat. No. 4,322,430.

3-Dialkylaminoalkoxy-4,5,6,7-tetrahydro-1H-indazoles having analgesic, antiinflammatory and antipyretic activities are described in Japan No. 4 9062-462.

1-Benzyl-4,5,6,7-tetrahydro-indazolyloxyalkanoic acids having utility as antiinflammatories and analgesics are described in Japan No. 5 0126-661.

1-Benzyl-3-alkoxycarbonylmethoxy-tetrahydro-1H-indazoles having antiinflammatory and analgesic activities are described in Japan No. 5 0126-662.

1-Substituted-3-benzyloxy-tetrahydroindazole derivatives are described in Japan No. 5 1008-268.

1-Substituted-3-hydroxy-tetrahydroindazole compounds having anti-rheumatism activity are described in Japan No. 5 1006-962.

1-Aryl-3-substituted-tetrahydroindazoles having utility as antiinflammatories and antirheumatics are described in Japan No. 5 2005-765.

1-Aryl-4,5,6,7-tetrahydro(1H)-indazolyloxyalkanoic acids useful as antiinflammatories and antirheumatics are described in Japan No. 5 2007-962.

1-Substituted-dialkylaminoalkoxy-tetrahydroindazoles useful as antiinflammatories, analgesics and antipyretics are described in Japan No. 5 2042-876.

3-Amino-2-substituted tetrahydroindazoles having fertility reducing activity are described in German No. 2,519,077.

1,3-Disubstituted cycloalkanopyrazoles having antiinflammatory and antiarrhythmic activity are described in U.S. Pat. No. 3,657,438.

Antidepressants which are 1-aryl-3-aminoalkoxycycloalkanopyrazole compounds are described in U.S. Pat. No. 3,629,433 and U.S. Pat. No. 3,637,738.

1-Substituted-cycloalkanopyrazole-3-carboxylic acids having antiviral activity are described in U.S. Pat. No. 3,691,179.

6,9-Deepoxy-6,9-phenylimino-Δ-6,8-prostaglandin $I_1$ and related compounds which are useful as antiasthmatic agents are described in U.S. Pat. No. 4,294,759 and copending application U.S. Ser. No. 426,231 filed Oct. 4, 1982.

M. K. Bach et al., Adv. Prostaglandin Thromboxane Leukotriene Res., 11:39–44 (1983), describes the in vivo and in vitro actions of a new selective inhibitor of leukotriene C and D synthesis.

M. K. Bach et al., Prostaglandins, 23:759–71 (1982), describes 6,9-deepoxy-6,9-(phenylimino)-Δ6,8-prostaglandin I, as a new inhibitor of leukotriene C and D synthesis in in vitro studies.

SUMMARY OF INVENTION

The present invention provides compounds which are useful as antiasthmatic agents anti-flammatory agents or chemical intermediates which have the structure depicted as Formula XXX in the Formula Chart wherein w is 1 or 2; wherein $R_1$ is:

(a) phenyl,
(b) m- or p-biphenylyl,
(c) benzyl,
(d) benzyl, the aromatic ring of which is substituted with one or two of the following groups, wherein said groups may be the same or different:
(1) —F,
(2) —Cl,
(3) —Br,
(4) —CF$_3$,
(5) —CH$_3$,
(6) —NO$_2$,
(7) —NHCOR$_4$,
(8) —OR$_4$, or
(9) —SR$_4$;
(e) phenyl substituted with one or two of the following groups, wherein said groups may be the same or different:
(1) —F,
(2) —Cl,
(3) —Br,
(4) —CF$_3$,
(5) —CH$_3$,
(6) —NO$_2$,
(7) —NHCOR$_4$,
(8) —OR$_4$, or
(9) —SR$_4$;
wherein R$_4$ is:
(a) —(C$_1$-C$_5$) alkyl, or
(b) phenyl;
wherein X is:
(a) cis or trans —CH=CH—,
(b) —CH$_2$CH$_2$—,
(c) cis or trans

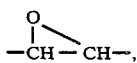

or
(d) —CH$_2$—;
wherein Y is:
(a) —(CH$_2$)$_n$—,
(b) —O—, or
(c) —S—;
wherein Z is:
(a) —COOM$_1$,
(b) —CH$_2$OH,
(c) —(CH$_2$)$_m$COOM$_1$,
(d) —(CH$_2$)$_p$CH$_2$OH,
(e) —(C$_1$-C$_4$) alkyl, or
(f) —CONR$_5$R$_6$; or
wherein X-Y-Z taken together are:
(a) —CHO,
(b)

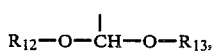

or
(c) —CH$_2$OH
wherein n is 0 to 5;
wherein m is 1 or 2;
wherein p is 2 or 3;
wherein M$_1$ is:
(a) —H,
(b) —(C$_1$-C$_4$) alkyl, (c) phenyl, or
(d) phenyl substituted with one or two of the following groups, wherein said groups may be the same or different:
(1) —F,
(2) —Cl,
(3) —Br,
(4) —CF$_3$,
(5) —CH$_3$,
(6) —NO$_2$,
(7) —NHCOR$_4$,
(8) —OR$_4$, or
(9) —SR$_4$;
wherein R$_5$ is:
(a) —H,
(b) —(C$_1$-C$_5$) alkyl,
(c) phenyl, or
(d) phenyl substituted with one or two of the following groups, wherein said groups may be the same or different:
(1) —F,
(2) —Cl,
(3) —Br,
(4) —CF$_3$,
(5) —CH$_3$,
(6) —NO$_2$,
(7) —NHCOR$_4$, or
(8) —OR$_4$;
wherein R$_6$ is:
(a) —H, or
(b) —(C$_1$-C$_5$) alkyl; or
wherein NR$_5$R$_6$ taken together are:
(a) pyrrolidino, or
(b) piperidino;
wherein R$_{12}$ and R$_{13}$ are the same and are:
(a) —CH$_3$, or
(b) —C$_2$H$_5$; or
wherein R$_{12}$R$_{13}$ taken together are:
(a) —(CH$_2$)$_q$—, or
(b) —CH$_2$C(CH$_3$)$_2$CH$_2$—;
wherein q is 2 or 3;
and pharmaceutically acceptable salts thereof; with the following provisos:
(a) when X is cis or trans-CH=CH— or —CH$_2$CH$_2$—, Y is —(CH$_2$)$_n$—, and Z is —COOM$_1$, —CH$_2$OH, —(C$_1$-C$_4$) alkyl or —CONR$_5$R$_6$;
(b) when X is —CH$_2$—, Y is —O— or —S—, and Z is —(CH$_2$)$_m$COOM$_1$ or —(CH$_2$)$_p$CH$_2$OH; and
(c) when X is cis or trans

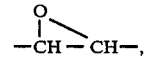

Y is —(CH$_2$)$_n$—, and Z is —COOM$_1$; and with the following compounds excluded:
(d) when X is

Y is —(CH$_2$)$_n$—, n is 0 to 5, Z is —COOM$_1$, w is 1 or 2 and R$_1$ is phenyl substituted with —SR$_4$;
(e) when X is —CH$_2$CH$_2$—, Y is —(CH$_2$)$_n$—, n is 0 to 5, Z is —(C$_1$-C$_4$) alkyl and w is 2;
(f) when X is —CH$_2$CH$_2$—, Y is —(CH$_2$)$_n$—, n is 0 or 1, Z is —CH$_3$, w is 1 and R$_1$ is phenyl substituted by one or two —F, —Cl or —Br atoms or two —NO$_2$ groups; and (g) when X-Y-Z taken together are —CH$_2$OH and w is 2.<>

All of the compounds of Formula XXX are useful as anti-asthmatic agents or antiinflammatory agents as described in detail below except for compounds of Formula XXX wherein: X is cis CH=CH, Y is (CH$_2$)$_n$, n is 3, Z is COOM$_1$, M$_1$ is H, w is 1 and R$_1$ is 4-methoxyphenyl. Although these excluded compounds do not possess anti-asthmatic properties said compounds are useful as intermediates in the preparation of compounds of Formula XXX which are useful as anti-asthmatics or antiinflammatories which will be apparent from the detailed description and specific examples set forth herein below.

The carbon atom content of various hydrocarbon-containing moieties is indicated by a prefix designating the minimum and maximum number of carbon atoms in the moiety, i.e., the prefix (C$_i$-C$_j$) indicates a moiety of the integer "i" to the integer "j" carbon atoms, inclusive. Thus, for example, (C$_1$-C$_3$) alkyl refers to alkyl of one to three carbon atoms, inclusive, or methyl, ethyl, propyl, and isopropyl.

Examples of alkyl of one to nine carbon atoms, inclusive, are methyl, ethyl, propyl, butyl, pentyl, hexyl, heptyl, octyl, and nonyl, and isomeric forms thereof.

Pharmaceutically acceptable salts of the compounds of Formula XXX wherein M$_1$ is hydrogen are those formed with any suitable inorganic or organic bases, such as those of alkali metals, for example, sodium and potassium; alkaline earth metals, for example, calcium and magnesium; light metals of Group IIIA, for example, aluminum, and organic amines. Such salts are pharmacologically acceptable amine salts, i.e., amines which are accepted by mammals in an essentially non-toxic manner when administered to mammals in conjunction with the acid moiety of the invention. Illustrative of the amines are those derived from primary, secondary, or tertiary amines. Examples of suitable amines are methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, adamantylamines, and like aliphatic, cycloaliphatic, and aralphatic amines containing up to and including about 18 carbon atoms as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, triethanolamine, ethyldiethanolamine, N-butylethanolamine, 2-amino-1-butanol, 2-amino-1-ethyl-1,3-propanediol, 2-amino-2-hydroxymethyl-1,3-propanediol (THAM), 2-amino-2-methyl-1-propanol, tri(hydroxymethyl)aminoethane, N-phenylethanolamine, N-(p-tert-amylphenyl)diethanolamine, galactamine, N-methylglucamine, N-methylglucosamine, ephedrin, phenylephrine, epinephrine, or procaine.

The compounds of the present invention will be named herein using the Chemical Abstracts numbering system (see "Naming and Indexing of Chemical Substances for Chemical Abstracts during the Ninth Collective Period (1972–1976)," a reprint of section IV from the Volume 76 Index Guide).

The process of the present invention is more completely understood by reference to the charts below. In these charts, the variables are as defined above. Formula IX represents the geometrical isomer mixture. Formulae X and XI represent the pure geometric isomers in the cis configuration and trans configuration, respectively.

The compounds of this invention are described by the procedure set forth hereinbelow. Chart A herein describes the method by which novel compounds of this invention are prepared. Charts B and C herein describe methods by which additional novel compounds of this invention are prepared from the final compound in Chart A. Chart D herein describes the method by which intermediates in Chart A may be prepared. Chart E herein describes the method by which additional novel compounds of this invention are prepared from intermediates in Chart A.

With respect to Chart A, condensation of the diazonium salt of the appropriate aromatic amine of formula I with ethyl acetoacetate provides the hydrazone of formula II. Bromination of the formula II hydrazone, as described in M. Nagakura et al., J. Med. Chem. 22:48 (1979), provides the bromo-substituted hydrazone of formula III. Dipolar cycloaddition of the nitrilamine derived from the formula III bromo-substituted hydrazone with the appropriate amine (e.g., morpholino-cyclopentene or pyrrolidino-cyclopentene; morpholino-cyclohexene or pyrrolidino-cyclohexene) provides the cyclopentapyrazole or tetrahydroindazole of formula IV where X is morpholino or pyrrolidino. Elimination of the cycloaliphatic amine moiety with aqueous acid or polyphosphoric acid in acetic acid provides the 3-carboethoxy cyclopentapyrazole or tetrahydroindazole of formula V. Precedents of the above reactions are described in M. Nagakura et al., J. Med. Chem. 22:48 (1979); R. Fusco et al., Gazz. Chim. Ital., 91:1233 (1961); R. Huisgen et al., Ang. Chem. 91:347 (1979); R. Huisgen et al., Tetrahedron Letters 32:2987 (1979). Other references include: German 2828–529; R. Scuri, Boll. Chim. Farm. 674 (1970); S. I. Nagai et al., Chem. Pharm. Bull. 27:1764 (1979); G. G. Massaroli et al., Boll. Chim. Farm. 107:613 (1968).

Reduction of the carboethoxy group of the formula V cyclopentapyrazole or tetrahydroindazole (e.g., when R$_1$ is phenyl, dichlorophenyl, difluorophenyl, trifluoromethylphenyl or methylphenyl) with lithium tetrahydroaluminate provides the carbinol of formula VII.

Alternatively, in the cases of aryl functionalities sensitive to lithium tetrahydroaluminate, the carboethoxy group of the formula V cyclopentapyrazole or tetrahydroindazole (e.g., when R$_1$ is nitrophenyl, bromophenyl, or chlorophenyl) is hydrolyzed to the acid of formula VI, and the carbinol of formula VII is obtained by treatment with diborane.

Oxidation of the carbinols of formula VII are conveniently performed with activated manganese dioxide in toluene under azeotropic distillation conditions to provide the carboxaldehydes of formula VIII. The carboxaldehydes of formula VIII are homologated to the geometrical isomer mixture of formula IX (e.g., when n is 1 to 5 and M$_1$ is —H) by Wittig reactions. The pure geometrical isomers of formula IX, i.e., formulae X and XI, are conveniently separated on silica gel as the corresponding methyl esters (e.g., when n is 1 to 5 and M$_1$ is —CH$_3$). These methyl esters are obtained by diazomethane esterification. Fisher-type esterifications (alcoholic hydrochloric acid or sulfuric acid) are applicable in larger scale operations. The pure geometrical isomers of formula IX, i.e., formulae X and XI, (e.g., when n is 1 to 5 and $M_1$ is —H) are regenerated by saponification in alcoholic sodium hydroxide solutions.

Condensation of the aldehydes of formula VIII with malonic acid provides the propenoic acids of formula XI (when n is 0 and $M_1$ is —H).

The carboxaldehydes of formula VIII are converted to the compound of formula XVII by Wittig reactions. The compound of formula XIII is obtained by reduction of the compound of formula XVII. Reduction of the vinyl group of formula XVII is conveniently performed by catalytic hydrogenation (e.g., palladium on carbon, platinum oxide catalysis) when substituents insensitive to reduction or hydrogenolysis are present (e.g., when $R_1$ is tolyl, trifluoromethylphenyl, fluorophenyl, or acetamidophenyl). Diborane reduction achieves the same objective when reduction-sensitive substituents are present (e.g., when $R_1$ is chlorophenyl, bromophenyl, or nitrophenyl). Geometrical isomers are separated on silica gel or more easily on silica gel pretreated with silver nitrate.

Further, the carboxaldehyde of formula VIII is converted to the compound of formula XXVII by reaction with alcohol (e.g., $R_{13}OH$ or $R_{12}OH$) or glycol (e.g.,

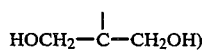

in the presence of acid (e.g., toluenesulfonic acid) neat in the case of lower-alkyl alcohols and with a solvent (e.g., toluene) in the case of glycols.

With respect to Chart B, reduction of the vinyl group of the formula IX compound to the formula XII compound is conveniently performed by catalytic hydrogenation (e.g., palladium on carbon, platinum oxide catalysis) when substituents insensitive to reduction or hydrogenolysis are present (e.g., when $R_1$ is tolyl, trifluoromethylphenyl, fluorophenyl, or acetamidophenyl). Diborane reduction achieves the same objective when reduction-sensitive substituents are present (e.g., when $R_1$ is chlorophenyl, bromophenyl, or nitrophenyl). The catalytic hydrogenations are easily performed on either the esters of formula IX (e.g., when n is 1 to 5 and $M_1$ is —CH$_3$) or the acids of formula IX (e.g., when n is 1 to 5 and $M_1$ is —H). Diborane reduction of vinyl substituents is best conducted on the esters of formula IX.

The terminal carbinols of formula XIV (when n is 1 to 5) are obtained either by lithium tetrahydroaluminate reduction of the esters or acids of formula XII (e.g., when n is 1 to 5 and $M_1$ is —CH$_3$ or —H) or by extending the reaction time with diborane.

With respect to both Charts B and C, the carboxylic acids of formulae XII and IX or pure isomers of formulae X and XI (e.g., when n is 1 to 5 and $M_1$ is —H) are activated for conversions to esters of formulae XII, IX, X and XI, respectively, (e.g., when n is 1 to 5 and $M_1$ is —(C$_1$-C$_4$) alkyl, phenyl or substituted phenyl) and amides of formula XXV and XVI (e.g., when n is 1 to 5 and $R_5$ and $R_6$ are as defined above) by procedures known in the art. Thus, the acid chlorides are synthesized by the procedure of J. Cason, Org. Syn., Coll. Vol. 3:169 (1955). For mixed anhydrides, the acid is reacted with, e.g., isobutylchloroformate/triethylamine in chlorocarbon solvents. Other methods include those of Y. Kita, Tetrahedron Letters 25:6027 (1984); K. Saigo, Bull. Chem. Soc. Japan 50:1863 (1977); and F. H. Stodola, J. Org. Chem. 29:2490 (1964).

The activated acids are then reacted with the appropriate alcohol (e.g., $M_1OH$) or amine (e.g., $HNR_5R_6$) to provide the esters or amides, respectively. The reaction of acid chlorides with alcohols or amines may be conducted in chlorocarbon solvents, tetrahydrofuran, or acetonitriles with an acid scavenger present (e.g., pyridine, triethylamine). The reaction of mixed anhydrides are conducted with or without solvent, the alcohol or amine, as noted above, being used as the solvent when convenient or the above listed solvent being used as required.

Further, with respect to Chart C, diphenylamine borane, according to the method of R. Contreras et al., Synthesis 1027 (1982), or lithium tetrahydride aluminate reduce the terminal acids or esters of formula IX (e.g., when $M_1$ is —H or —CH$_3$), respectively, to the unsaturated carbinols of formula XV.

The epoxidation reaction of the compound of formula IX (e.g., when n is 1 to 5 and $M_1$ is —H or —CH$_3$) to the formula XXVI expoxide is carried out conveniently in methylene chloride with m-chloroperoxybenzoic acid for from four to twenty-four hours. The vinyl group yields an expoxy group of like cis or trans configuration. An example of such a reaction is presented in J. Fried et al., Tetrahedron Letters 849 (1965).

With respect to Chart D, the cyclohexanone glyoxylate of formula XIX, K. V. Auwers et al., Ann. 57:469 (1929) is condensed with a hydrazine derivative of formula XVIII (e.g., when $R_1$ is 4-alkoxyphenyl, 4-thioalkylphenyl, benzyl or substituted benzyl) by literature procedures, e.g., L. G. Tensmeyer and C. Ainsworth, J. Org. Chem. 31:1878 (1966). The resulting isomeric cyclopentapyrazoles or tetrahydroindazoles of formula V (e.g., when $R_1$ is 4-alkoxyphenyl, benzyl or substituted benzyl) are separated by chromatography and the side chain of the formula V compound is elaborated by procedures described for Chart A.

With respect to Chart E, heteroatom chains of the formula XX compound (e.g., when m is 1 or 2 and $M_1$ is —CH$_3$, —CH$_2$CH$_3$ or —H) are elaborated by generation of the alkoxide from the formula VII compound and condensation with a halo ester (e.g., ethyl bromoacetate). The halomethylcyclopentapyrazole or halomethyltetrahydroindazole of formula XXI is prepared from the formula VII compound and thionyl chloride (or, alternatively, methane sulfonyl chloride). The thia side chains of the formula XXII compound, (e.g., when m is 1 or 2 and $M_1$ is —H, —CH$_3$ or —CH$_2$CH$_3$) are produced from the halomethylcyclopentapyrazole or halomethyltetrahydroindazole of formula XXI by condensation with a mercapto ester (e.g., methyl thioglycollate).

The terminal carbinols of formulae XXIII and XXIV are obtained either by lithium tetrahydroaluminate reduction of the esters or acids of formulae XX and XXII or by extending the reaction time of diborane reduction.

The compounds of Formula XXX, except for the following compounds: (1) X is cis —CH=CH—, Y is —(CH$_2$)$_n$—, n is 3, Z is —COOM$_1$, $M_1$ is —H, $R_1$ is 4-methoxyphenyl and w is 1; (2) X-Y-Z taken together are —CH$_2$OH, $R_1$ is 3,4-dichlorophenyl and w is 1; (3) X-Y-Z taken together are —CH$_2$OH, $R_1$ is 4-fluorophenyl and w is 2; and (4) X is trans —CH=CH—, Y is —(CH$_2$)$_n$—, n is 2, Z is —COOM$_1$, $M_1$ is —CH$_3$, $R_1$ is 3,4-dichlorophenyl and w is 1; are useful for the prophylactic or therapeutic treatment of allergy of a reagin or non-reagin mediated nature in humans and animals, particularly mammals. These compounds are particularly useful in treating asthma, but any allergy wherein slow reacting substance of anaphylaxis (SRSA) is thought to be involved as a pharmacological mediator of anaphylaxis can be treated. For example, the compounds can be used for treatment of such conditions as allergic rhinitis, food allergy and urticaria as well as asthma.

An effective but essentially non-toxic quantity of these pharmaceutically useful compounds are employed in treatment. The dosage of the compound used in treatment depends on the particular use, frequency of administration and the age or condition of the recipient. The compounds can be administered intravenously, intramuscularly, topically, bucally, by aerosol, inhalation, or orally to man or other animals. The dosage is about 0.01 to 10 μg/kg per minute by intravenous infusion, i.e., an i.v. drip; 0.5 to 20 mg by intravenous bolus administration one to four times per day; about 2 to 50 mg orally in single doses; 200–800 mg total daily dosage given in divided doses two or three times a day.

The pharmaceutically useful compounds are formulated into compositions for administration. The compositions of the present invention are presented for administration to humans and animals in unit dosage forms, such as tablets, capsules, pills, powders, granules, sterile parenteral solutions or suspensions, eye drops, oral solutions or suspensions, oil in water and water in oil emulsions containing suitable quantities of the compound, suppositories, aerosols and in fluid suspensions or solutions.

For oral administration, either solid or fluid unit dosage forms can be prepared. For preparing solid compositions such as tablets, the pharmaceutically useful compound of Formula XXX is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petroleum or other inert oil.

Fluid unit dosage forms for oral administration such as syrups, elixirs, and suspensions can be prepared. The forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The pharmaceutically useful compound described herein, depending on the vehicle and concentration used, can be either suspended or dissolved in the vehicle. In preparing solutions the compound can be dissolved in water for injection and filter sterilzed before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. These compounds can be sterilized by exposure to ethylene oxide or an equivalent gas before suspending in the sterile vehicle. Advantageously, a surfactant or wetting agent is included in the composition to facilitate uniform distribution of the compound.

Compositions for inhalation useful in practicing the present invention are of three basic types: (1) a powder mixture preferably micropulverized with particle size, preferably from about 2 to 5 microns; (2) an aqueous solution to be sprayed with a nebulizer; (3) an aerosol with volatile propellant in a pressurized container.

The powders are quite simply prepared by mixing a suitable pharmaceutically useful compound of Formula XXX with a solid base which is compatible with lung tissue, preferably lactose. The powders are packaged in a device adapted to emit a measured amount of powder when inhaled through the mouth.

Aqueous solutions are prepared by dissolving the appropriate compound of the Formula XXX in water and adding salt to provide an isotonic solution and buffering to a pH compatible with inhalation. The solutions are dispersed in a spray device or nebulizer and sprayed into the mouth while inhaling.

Aerosols are prepared by dissolving an appropriate pharmaceutically useful compound of Formula XXX in water or ethanol and mixing with a volatile propellant and placing in a pressurized container having a metering valve to release a predetermined amount of material.

The liquefied propellent employed is one which has a boiling point below 65° F. at atmospheric pressure. For use in compositions intended to produce aerosols for medicinal use, the liquefied propellant should be non-toxic. Among the suitable liquefied propellants which may be employed are the lower alkanes containing up to 5 carbon atoms, such as butane and pentane, or a lower alkyl chloride, such as methyl, ethyl or propyl chlorides. Further suitable liquefied propellants are the fluorinated and fluorochlorinated lower alkanes such as are sold under the trademarks "Freon" and "Genetron". Mixtures of the above-mentioned propellants may suitably be employed. Examples of these propellants are dichlorodifluoromethane ("Freon 12"), dichlorotetrafluoroethane ("Freon 114"), trichloromonofluoromethane ("Freon 11"), dichloromonofluoromethane ("Freon 21"), monochlorodifluoromethane ("Freon 22"), trichlorotrifluoroethane ("Freon 113"), difluoroethane ("Genetron 142-A") and monochlorotrifluoromethane ("Freon 13").

The compounds of Formula XXX wherein (1) X-Y-Z taken together are —CH$_2$OH, R$_1$ is 3,4-dichlorophenyl and w is 1; (2) X-Y-Z taken together are —CH$_2$OH, R$_1$ is 4-fluorophenyl and w is 2; and (3) X is trans—CH=CH—, Y is —(CH$_2$)$_n$—, n is 2, Z is —COOM$_1$, M$_1$ is —CH$_3$, R$_1$ is 3,4-dichlorophenyl and w is 1; are useful for the treatment of acute and chronic inflammatory diseases in humans and animals, particularly mammals, and are particularly valuable in the treatment of inflammatory dismenorrhea, acute rheumatic fever, rheumatic carditis, synovial inflammatic of joint disease, rheumatoic arthritis, osteoarthritis and the inflammatory components of immunological and soft tissue insults.

The above-enumerated compounds of Formula XXX as well as those set forth hereinbelow are administered for use in treating or preventing inflammatory conditions in the same dosage, mode and host as described above for the treatment of allergy. Oral and parenteral routes of administration to the particular warm blooded animal being treated are preferred. The following compounds are also particularly useful in treating inflammation:

Cyclopentapyrazole, 3-heptyl-1,4,5,6-tetrahydro-1-phenyl-; Acetic acid, [[1-(4-chlorophenyl)-1,4,5,6-tetrahydro-3-cyclopentapyrazolyl]methoxy]-; Propanoic acid, 3-[[(1,4,5,6-tetrahydro-1-phenyl-3-cyclopentapyrazolyl)methyl]thio]-; 5-Hexenoic acid, 6-[1-(4-fluorophenyl)-1,4,5,6-tetrahydro-3-cyclopentapyrazolyl]-, methyl ester; 5-Hexenoic acid, 6-[1,4,5,6-tetrahydro-1-(4-methoxyphenyl)-3-cyclopentapyrazolyl]-, (E)-; 5-Hexenoic acid, 6-[1-(3,4-dichlorophenyl)-1,4,5,6-tetrahydro-3-cyclopentapyrazolyl]-, methyl ester, (Z)-; 5-Hexenoic acid, 6-[1-(3,4a dichlorophenyl)-1,4,5,6-tetrahydro-3-cyclopentapyrazolyl]-, methyl ester, (E)-; 4-Pentenoic acid, 5-[1-(3,4-dichlorophenyl)-1,4,5,6-tetrahydro-3-cyclopentapyrazolyl]-, methyl ester, (Z)-; 4-Pentenoic acid, 5-[1-(3,4-dichlorophenyl)-1,4,5,6-tetrahydro-3-cyclopentapyrazolyl]-, methyl ester, (E)-; 4-Pentenoic acid, 5-[1-(3,4-dichlorophenyl)-1,4,5,6-tetrahydro-3-cyclopentapyrazolyl]-, (Z)-; 3-Cyclopentapyrazolepentanoic acid, 1-(3,4-dichlorophenyl)-1,4,5,6-tetrahydro-; 1-Propanol, 3-[[1,4,5,6-tetrahydro-1-[3-(trifluoromethyl)phenyl]-3-cyclopentapyrazolyl]methoxy]-; Propanoic acid, 3-[[1,4,5,6-tetrahydro-1-[3-(trifluoromethyl)phenyl]-3-cyclopentapyrazolyl]methoxy]-; 1H-Indazole-3-hexanol, 1-(4-bromophenyl)-4,5,6,7-tetrahydro-; 5-Hexenoic acid, 6-[1-(4-fluorophenyl)-4,5,6,7-tetrahydro-1H-indazol-3-yl]-, (Z)-; 1H-Indazole-3-carboxaldehyde, 4,5,6,7-tetrahydro-1-phenyl; 4-Pentanoic acid, 5-(4,5,6,7-tetrahydro-1-phenyl-1H-indazol-3-yl)-, (E)-; Acetic acid, [[(4,5,6,7-tetrahydro-1-phenyl-1H-indazol-3-yl)methyl]thio]; Acetic acid, [[1-(4-bromophenyl)-4,5,6,7-tetrahydro-1H-indazol-3-yl]methoxy]-; Propanoic acid, 3-[[4,5,6,7-tetrahydro-1-phenyl-1H-indazol-3-yl]methyl]thio]-; 1H-Indazole-3-hexanoic acid, 1-(4-fluorophenyl)-4,5,6,7-tetrahydro-; 5-Hexenoic acid, 6-[4,5,6,7-tetrahydro-1-[3-(trifluoromethyl)phenyl]-1H-indazol-3-yl]-, (Z)-; 5-Hexenoic acid, 6-[4,5,6,7-tetrahydro-1-[3-(trifluoromethyl)phenyl]-1H-indazol-3-yl]-, (E)-; and 1H-Indozole-3-pentanoic acid, 4,5,6,7-tetrahydro-1-[3-(trifluoromethyl)phenyl]-.

DESCRIPTION OF THE PREFERRED EMBODIMENTS

The abbreviations for some of the chemical names used in some of these examples are the following: DMF is dimethylformamide; DMSO is dimethylsulfoxide; THF is tetrahydrofuran; Skelly B is Skellysolve-B; $BF_3$ etherate is boronitrifluoride etherate; $PtO_2$ is platinum oxide.

The abbreviations for units of measure used in these examples are the following: psi is pounds per square inch; lit is literature; dec. is decomposition.

The data included in some of the examples are for the following tests: IR is infrared spectroscopy; NMR is nuclear magnetic resonance; MS is mass spectrum; UV is ultraviolet spectra; tlc is thin layer chromatography.

The following specific examples illustrate the preparation of compounds of the invention. These examples are not meant to be limiting and variations for processes to prepare compounds generally within the scope as defined for Formula XXX above or within the skill of an ordinary artisan.

EXAMPLE 1

6-[1-3,4-Dichlorophenyl-1,4,5,6-tetrahydro]-3-cyclopentapyrazole-5-EZ-hexenoic acid (Formula IX, $R_1$=dichlorophenyl, n=3, $M_1$=H, w=1) Refer to Chart A.

(a) 2-[(3,4-Dichlorophenyl)-hydrazono]-3-oxo-butanoic acid ethyl ester (Formula II, $R_1$ = 3,4-dichlorophenyl)

A solution of 3,4-dichloroaniline (48.6 g, 0.3 mole) in water (150 ml) and concentrated hydrochloric acid (75 ml) was prepared by heating at 90°–95° C. The solution was cooled, diluted to 500 ml with water and cooled to 0° C. A solution of sodium nitrite (20.7 g, 0.3 mole) in water (100 ml) was added in portions while retaining the reaction at 0° C.

A solution of ethyl acetoacetate (38.2 ml, 39 g, 0.3 mole) in ethanol (225 ml) containing sodium acetate (75 g) was treated with ice water (1.5 L). The diazonium salt solution was added at −5° C. and the mixture was reacted for 2 hours at 0° C., then at 4° C. for 18 hours. The precipitate was filtered and crystallized from ethanol to yield pure title compound 1(a), 78.7 g, m.p. 115° C.

(b) Bromo-[(3,4-dichlorophenyl)-hydrazono]-acetic acid ethyl ester (Formula III, $R_1$ = 3,4-dichlorophenyl)

A solution of compound 1(a) (78.7 g, 230 mmol) in glacial acetic acid (1 L), acetic anhydride (330 ml) and sodium acetate (47 g, 575 mmol) was treated dropwise during 60 minutes with bromine (11.8 ml, 230 mmol) at 2° C. The solution was reacted for 2.5 hours at 5°–8° C., diluted to 4 L with water and stirred until a granular precipitate was obtained. The precipitate was filtered to provide crude product which was recrystallized from chloroform-hexane solution to give pure title compound 1(b) (67 g), m.p. 145°–146° C.

(c)
1-(3,4-Dichlorophenyl)-1,3a,4,5,6,6a-hexahydro-6a-1-pyrrolidinyl)-3-cyclopentapyrazole-carboxylic acid ethyl ester (Formula IV, $R_1$ = 3,4-dichlorophenyl, w=1)

A suspension of compound 1(b) (50.66 g, 149 mmol) in toluene (625 ml) was cooled to −5° C. A solution of pyrrolidino-2-cyclopent-ane (20.67 g, 149 mmol) and triethylamine (20.9 ml, 15.1 g, 149 mmol) in toluene (65 ml) was added during 60 minutes. The mixture was stirred at −5° C. for 1.5 hours, brought to ambient temperature, and reacted for 18 hours. The mixture was diluted with 5% brine, dried and evaporated. The residue was crystallized from acetonitrile to yield pure title compound 1(c) (45.9 g), m.p. 135°–136° C.

(d)
1-(3,4-Dichlorophenyl)-1,4,5,6-tetrahydro-3-cyclopentapyrazole carboxylic acid ethyl ester (Formula V, $R_1$ = 3,4-dichlorophenyl, w=1)

A solution of compound 1(c) (32.8 g, 85.2 mmol) in 25% polyphosphoric acid in glacial acetic acid (330 ml)

was heated at 98° C. for 3.5 hours. The solution was cooled, poured into ice water (1.5 L) and the precipitate was filtered to yield the title compound 1(d) (22.3 g). Analytical material, m.p. 119°–120° C., was obtained by recrystallization from ethanol.

(e)

1-(3,4-Dichlorophenyl)-1,4,5,6-tetrahydro-3-cyclopentapyrazole methanol (Formula VII, $R_1$ = 3,4-dichlorophenyl, w = 1)

A solution of compound 1(d) (20.6 g, 63.3 mmol) in tetrahydrofuran (THF) (316 ml) was treated with lithium tetrahydrido aluminate (4.80 g) in portions. Ten minutes after complete addition of reagent, the suspension was cooled to 5° C., treated with 10% aqueous THF (48 ml) dropwise, 4.8 ml of 15% sodium hydroxide, and then 15 ml of water. The mixture was filtered, the filter cake washed with ethyl acetate, and the combined filtrates were washed with 5% brine, dried and evaporated. The residue was crystallized from acetonitrile to yield pure title compound 1(e) (16.14 g), m.p. 118°–119° C.

(f)

1-(3,4-Dichlorophenyl)-1,4,5,6-tetrahydro-3-cyclopentapyrazole carboxaldehyde (Formula VIII, $R_1$ = 3,4-dichlorophenyl, w = 1)

A solution of compound 1(e) (10 g, 35.5 mmol) in toluene (300 ml) at 70° C. was treated with activated manganese dioxide (30 g) and azeotropically distilled for 3 hours. The hot mixture was filtered and the filtrate evaporated to provide pure title compound 1(f), (7.9 g, 79%). An analytical sample was prepared by ethanol recrystallization, m.p. 154°–155° C.

(g)

6-[1-(3,4-Dichlorophenyl)-1,4,5,6-tetrahydro-3-cyclopentapyrazole-5-EZ hexanoic acid (Formula IX, $R_1$ = 3,4-dichlorophenyl, n = 3, $M_1$ = H, w = 1)

Dimsyl sodium was prepared from 60% sodium hydride (2.12 g, 53 mmol) in DMSO (80 ml) at 60° C. during 4 hours. The solution was cooled to 18° C. and 4-carboxy-butyltriphenylphosphonium bromide (11.7 g, 26.5 mmol) was added. The ylide was generated during 30 minutes and compound 1(f) (3.7 g, 13.2 mmol) was added and reacted for 30 minutes. The solution was poured into ice water (700 ml) and extracted with ether to remove neutral products. The aqueous phase was slowly acidified with 1N hydrochloric acid and the precipitate was filtered. The filter cake was triturated with cold ethanol and crude title compound 1(g) filtered (4.37 g, 91%).

IR (mull): 1740, 1720, 1600, 1590, 1500, 1470, 1415, 1380, 1340, 1310, 1280, 1260, 1240, 1215, 1175, 1140, 1080, 1065, 980, 955, 895, 880, and 820 cm$^{-1}$.

NMR (CDCl$_3$) δ: 1.57–3.06, 5.5–6.6, 6.5, 6.3, 6.77, 7.49, 7.74.

EXAMPLE 2

6-[1-(4-Methoxyphenyl)-1,4,5,6-tetrahydro-3-cyclopentapyra-zol-3-yl]-(E)-5-hexenoic acid and Z-6-[1-(4-methoxyphenyl)-1,4,5,6-tetrahydro-3-cyclopentapyrazol-3-yl]-5-hexenoic acid (Formula IX, $R_1$ = methoxyphenyl, n = 3, $M_1$ = H, w = 1) Refer to Charts D and A.

(a)

1-(4-Methoxyphenyl)-1,4,5,6-tetrahydro-3-cyclopentapyrazole carboxylic acid ethyl ester (Formula V, $R_1$ = methoxyphenyl, w = 1)

A solution of the compound of Formula XIX (14.7 g, 80 mmol) in ethanol (600 ml) was treated with p-methoxyphenylhydrazine hydrochloride of Formula XVIII (13.97 g, 80.3 mmol) and heated at reflux temperature for 12 hours. The dark solution was concentrated to 100 ml and poured into water (600 ml). The precipitate was extracted into ethyl acetate, washed with 1N hydrochloric acid, dried and evaporated. The dark residue was triturated with hot Skelly B and filtered to yield crude title compound (12.5 g). Crystallization from methylene chloride gave pure title compound (7.52 g), m.p. 108°–109° C.

(b)

1-(4-Methoxyphenyl)-1,4,5,6-tetrahydro-3-cyclopentapyrazolmethanol (Formula VII, $R_1$ = methoxyphenyl, w = 1)

A solution of the compound of Example 2(a) (10.16 g, 35.5 mmol) in THF (300 ml) was treated with lithium tetrahydroaluminate (2.5 g) and reacted for 3 hours. Excess reagent was quenched, the mixture diluted with ethyl acetate, and filtered. The filter cake was washed with hot ethyl acetate and the combined filtrates were washed with 5% sodium chloride, dried, and evaporated to yield the title compound. Crystallization from methylene chloride-hexane provided pure title compound, m.p. 88°–89° C.

(c)

1-(4-Methoxyphenyl)-1,4,5,6-tetrahydro-3-cyclopentapyrazolecarboxaldehyde (Formula VIII, $R_1$ = methoxyphenyl, w = 1)

A solution of the compound of Example 2(b) (6.49 g, 30 mmol) in toluene (500 ml) was treated with activated manganese dioxide (16.23 g) and azeotropically distilled for 3 hours. The hot solution was filtered, the filter cake washed with hot ethyl acetate, and the combined filtrates evaporated to yield the title compound (5.40 g). Crystallization from ethanol gave pure title compound.

(d)

6-[1-(4-Methoxyphenyl)-1,4,5,6-tetrahydro-3-cyclopentapyrazol-3-yl]-(E)-5-hexenoic acid and Z-6-[1-(4-methoxyphenyl)-1,4,5,6-tetrahydro3-cyclopentapyrazol-3-yl]-5-hexenoic acid (Formula IX, $R_1$ = methoxyphenyl, n = 3, $M_1$ = H, w = 1)

Dimsyl sodium was prepared from 60% sodium hydride (2.65 g, 65 mmol) in DMSO (130 ml) at 60°–65° C. during 4 hours. The cooled solution was treated with 4-carboxybutyl-triphenylphosphonium bromide (14.4 g, 32.5 mmol) and reacted for 30 minutes at ambient temperature. The aldehyde of Example 2(c) (4.0 g, 16.5 mmol) was added and reaction allowed to proceed for 18 hours. The solution was poured into ice water (600 ml) and neutral products removed by ether extraction.

The aqueous phase was acidified and the precipitate was extracted into ethyl acetate. The residual oil from solvent evaporation was purified on CC-4 silica gel (650 g) using 9:1 Skelly B-ethyl acetate. Fractions 80–210 (20 ml fractions) were combined to yield the Z-isomer title compound (1.06 g), m.p. 120°–121° C. Subsequent fractions gave 5.30 g of E-Z mixture. Crystallization of the E-Z mixture from toluene gave pure E-isomer title compound (1.88 g), m.p. 132°–134° C. The filtrate residue was refractionated on silica gel to provide additional Z-isomer title compound.

EXAMPLE 3

6-[1-(3,4-Dichlorophenyl)-1,4,5,6-tetrahydro-3-cyclo-entapyrazole]-5Z-hexenoic acid methyl ester and
6-[1-(3,4-dichlorophenyl)-1,4,5,6-tetrahydro-3-cyclopentapyrazole]-5E-hexenoic acid methyl ester (Formulas X and XI, $R_1 = 3,4$-dichlorophenyl, $n = 3$, $M_1 = CH_3$, $w = 1$) Refer to Chart A.

A solution of the E-Z mixture of acids of 6-[1-(3,4-dichlorophenyl)-1,4,5,6-tetrahydro-3-cyclopentapyrazole-5-EZ-hexenoic acid prepared in Example 1(g) (3.0 g) in ethyl acetate (300 ml) was cooled to 0° C. and excess ethereal diazomethane was added. Excess reagent was quenched with acetic acid and the solution was washed with 5% brine and 5% sodium bicarbonate solution. Drying and evaporation of solvent gave the isomeric esters (3.20 g). The mixed products were separated on silica gel (300 g) with 9:1 Skelly B-ethyl acetate eluent. Pure 5Z-isomer (0.90 g) was obtained in fractions 70–86 (20 ml fractions), pure 5E-isomer (0.1 g) was obtained in fractions 110–130; the intermediate fractions gave mixed products (1.1 g).

Analytical samples of the 5Z-isomer (m.p. 60°–61° C.) and 5E-isomer (m.p. 72°–73° C.) were obtained by ethanol crystallizations.

EXAMPLE 4

6-[1-(3,4-Dichlorophenyl)-1,4,5,6-tetrahydro-3-cyclopentapyrazole]-5E hexenoic acid (Formula XI, $R_1 = 3,4$-dichlorophenyl, $n = 3$, $M_1 = H$, $w = 1$)

A solution of the 5E isomer of Example 3 (0.31 g) in methanol (25 ml) and 1N sodium hydroxide was hydrolyzed at ambient temperature for 18 hours. The solution was concentrated, diluted with water, acidified, and the precipitate was filtered to yield the title compound (0.36 g). The analytical sample was obtained by ethanol crystallization, m.p. 163°–164° C.

EXAMPLE 5

5-[1-(3,4-Dichlorophenyl-1,4,5,6-tetrahydro-3-cyclopentapyrazole]-4-EZ-pentenoic acid (Formula IX, $R_1 = 3,4$-dichlorophenyl, $n = 2$, $M_1 = H$, $w = 1$) Refer to Chart A.

Dimsyl sodium was prepared from 60% sodium hydride and DMSO (80 ml) at 60°–65° C. for 4 hours. The solution was cooled to 15° C. and 3-carboxypropyltriphenylphosphonium bromide (11.37 g, 26.5 mmol) was added. The ylide was allowed to generate during 45 minutes. The solution was treated with the compound of Example 1(f) (3.7 g, 13.2 mmol) and reacted for 60 minutes. The reaction solution was poured into ice water (700 ml), extracted with ether, and the aqueous phase was acidified. The precipitate was filtered and the filter cake triturated with ethanol to yield the title compound (3.6 g).

IR (mull): 3200–2400, 1715, 1600, 1490 (sh), 1465, 1405, 1380, 1310 (sh), 1220, 1200, 1135, 1110, 1060, 1025, 965, 940, 880, 800, 780 and 765 cm$^{-1}$.

NMR (CDCl$_3$) δ: 2.25–3.20, 5.68–6.3, 6.43, 7.5–7.9.

EXAMPLE 6

6-[1-(3,4-Dichlorophenyl)-1,4,5,6-tetrahydro-3-cyclopentapyrazole]-5Z-pentenoic acid methyl ester and
6-[1-(3,4-dichlorophenyl)-1,4,5,6-tetrahydro-3-cyclopentapyrazole]-5E-pentenoic acid methyl ester (Formulas X and XI, $R_1 = 3,4$-dichlorophenyl, $n = 2$, $M_1 = CH_3$, $w = 1$) Refer to Chart A.

A solution of the isomeric acids prepared in Example 5 (3.55 g) in ethanol (50 ml) was diluted to 400 ml with ethyl acetate and esterified with excess ethereal diazomethane. Excess reaagent was quenched with acetic acid, the solution was washed with 5% brine and 5% carbonate solutions, dried and evaporated to yield 3.47 g of isomeric esters. Purification on silica gel (350 g) with 9:1 Skelly B-ethyl acetate (20 ml fractions) gave pure 5Z-isomer (1.26 g), m.p. 61°–62° C. after ethanol crystallization. Fractions 105–160 gave pure 5E-isomer (1.62 g), m.p. 92°–93° C., after ethanol crystallization.

EXAMPLE 7

6-[1-(3,4-Dichlorophenyl)-1,4,5,6-tetrahydro-3-cyclopentapyrazole]-5E-pentenoic acid (Formula IX, $R_1 = 3,4$-dichlorophenyl, $n = 2$, $M_1 = H$, $w = 1$)

A solution of the compound of Example 6 (1.2 g) was dissolved in methanol (250 ml), treated with 2N sodium hydroxide (35 ml) and reacted at ambient temperature for 18 hours. The solution was concentrated, diluted with water, acidified, and the precipitate was filtered to yield the title compound. Crystallization from ethanol provided pure compound, m.p. 176°–177° C.

EXAMPLE 8

6-[1-(3,4-Dichlorophenyl)-1,4,5,6-tetrahydro-3-cyclopentapyrazole]-5Z-hexenoic acid (Formula X, $R_1 = 3,4$-dichlorophenyl, $n = 3$, $M_1 = H$, $w = 1$)

A solution of the 5Z-isomer of Example 3 (0.29 g) in methanol (40 ml) was treated with 1N sodium hydroxide (8 ml) and reacted at ambient temperature for 18 hours. The solution was concentrated, the residue diluted with water, and acidified with 1N hydrochloric acid. The precipitated product was filtered to yield 0.28 g of the title compound. An analytical sample (m.p. 122°–123° C.) was obtained by ethanol recrystallization.

EXAMPLE 9

6-[1-(3,4-Dichlorophenyl)-1,4,5,6-tetrahydro-3-cyclopentapyrazole]-5Z-pentenoic acid (Formula X, $R_1 = 3,4$-dichlorophenyl, $n = 2$, $M_1 = H$, $w = 1$)

A solution of the 5Z-isomer of Example 6 (0.80 L g) was dissolved in methanol (150 ml), treated with 2N sodium hydroxide (24 ml) and reacted at ambient temperature for 18 hours. The solution was concentrated, diluted with water, acidified, and the precipitate was filtered to yield the title compound. Crystallization from ethanol gave 750 mg of pure title compound, m.p. 141°–142° C. as two crops.

EXAMPLE 10

6-[1-(3,4-Dichlorophenyl)-1,4,5,6-tetrahydrocyclopentapyrazole]-hexanoic acid (Formula XII, $R_1$=3,4-dichlorophenyl, n=3, $M_1$=H, w=1) Refer to Chart B.

A solution of crude compound of Example 1(g) (0.60 mg) in ethanol (100 ml) was treated with 10% palladium on carbon (0.20 g) and reduced at 40 psi for 30 minutes. The catalyst was filtered and the solvent evaporated to yield the title compound (0.36 g). Crystallization from ethanol gave pure title compound (0.35 g), m.p. 109°–110° C. as two crops.

EXAMPLE 11

6-[1-(3,4-Dichlorophenyl)-1,4,5,6-tetrahydrocyclopentapyrazole]-pentanoic acid (Formula XII, $R_1$=3,4-dichlorophenyl, n=2, $M_1$=H, w=1) Refer to Chart B.

A solution of the compound of Example 7 (0.20 g) in glacial acetic acid (30 ml) was treated with platinum oxide (20 ml) and reduced at 40 psi for 30 minutes. The catalyst was filtered and the filtrate slowly deposited pure title compound (0.17 g), m.p. 118°–119° C. An analytical sample was obtained by ethyl acetate-hexane recrystallization.

EXAMPLE 12

6-[1-(3,4-Dichlorophenyl)-1,4,5,6-tetrahydro-3-cyclopentapyrazole]carboxylic acid (Formula VI, $R_1$=3,4-dichlorophenyl, w=1) Refer to Chart A.

A solution of compound of Formula 1(c) (2.83 g) in 1:1 (volv:vol) glacial acetic acid-concentrated hydrochloric acid (60 ml) was heated at 90°–95° C. for 35 hours. The solution solution was cooled, diluted with water, and the precipitate was extracted into ethyl acetate. The extract was washed with 5% brine, dried and evaporated. Two recrystallizations gave pure title compound (0.95 g), m.p. 261° C. dec.

EXAMPLE 13

6-[1,4,5,6-Tetrahydro-1-(4-nitrophenyl)-3-cyclopentapyrazole]-(E)-5-hexenoic acid and -(Z)-5-hexenoic acid methyl esters (Formulas XI and X, $R_1$=4-nitrophenyl, n=3, $M_1$=$CH_3$, w=1) Refer to Chart A.

(a) 2-[(4-Nitrophenyl)hydrazono]-3-oxo-butanoic acid ethyl ester (Formula II, $R_1$=4-nitrophenyl)

A suspension of 4-nitroaniline (41.43 g, 0.3 mmol) in water (150 ml) and 37% hydrochloric acid (75 ml) was heated to dissolution. The cooled suspension of hydrochloride salt was treated with sodium nitrite (20.7 g) at −5° C. at a rate which maintained the reaction temperature at −2° C. The diazonium salt solution was added to a solution of ethyl acetoacetate (39 g, 0.3 mmol) in ethanol (225 ml) and ice water (1.5 L) containing sodium acetate (75 g, 0.9 mmol). The mixture thickened and sufficient water was added to permit agitation for 3.5 hours. The mixture was filtered, the filter cake washed with water, and crystallized from ethanol to yield the title compound, (79.16 g), m.p. 128° C.

(b) Bromo[(4-nitrophenyl)hydrazono-acetic acid ethyl ester (Formula III, $R_1$=4-nitrophenyl)

A suspension of compound 13(a) (78.08 g, 0.28 mmol) at 3° C. in acetic acid (500 ml), acetic anhydride (165 ml) and sodium acetate (57.23 g) was treated with bromine (44.79 g, 0.280 mmol) in acetic acid during 2 hours. Dissolution of compound 13(a) occurred during the addition. The mixture was reacted at 2°–5° C. for 1.5 hours, diluted to 4 L with ice water, and agitated for 2 hours until the precipitate became crystalline. The precipitate was filtered and dried to yield crude title compound (95.4 g). Crystallization from methylene chloride-ethanol solution gave pure title compound (82.4 g), m.p. 199°–200° C. as three crops. An analytical sample was obtained from ethanol-toluene solution, m.p. 201.5°–202° C.

(c) 1-(4-Nitrophenyl)-1,3a,4,5,6,6a-hexahydro-6a-(1-pyrrolidinyl)-3-cyclopentapyrazole carboxylic acid ethyl ester (Formula IV, $R_1$=4-nitrophenyl, w=1)

A suspension of compound 13(b) (31.6 g, 0.1 mole) in toluene (180 ml) at −5° C. was treated with pyrrolidinocyclopentene (14.5 ml, 13.7 g, 0.1 mole). The dark suspension was exothermic to 70° C. The exothermic reaction subsided after 7 minutes, and a solution of triethylamine (15.18 g, 0.15 mmol) in toluene was added during 15 minutes. The suspension was diluted with toluene to retain fluidity, reacted at 0° C. for 1.75 hours, then at ambient temperature for 17 hours. The suspension was diluted to 500 ml with toluene, then to 2.5 L with ethyl acetate. The red solution was washed with 5% saline, dried and evaporated to yield crude title compound (28.6 g), an oil which slowly solidified. Crystallization from ethanol gave pure title compound, m.p. 118° C.

(d) 1-(4-Nitrophenyl)-1,4,5,6-tetrahydro-3-cyclopentapyrazole-carboxylic acid (Formula VI, $R_1$=4-nitrophenyl, w=1)

A solution of crude compound 13(c) (28.6 g) in acetic acid (250 ml) and 1N hydrochloric acid (200 ml) was heated at reflux for 19 hours. Intermittent analyses of the reaction showed the title compound and the corresponding ethyl ester of Formula V. The suspension was concentrated, diluted with water and the precipitate mixture was filtered to yield 18.9 g of mixed acid and ester. Hydrolysis of the mixture in ethanolic (300 ml) 2N sodium hydroxide (50 ml) at reflux temperature for 5 hours and precipitation of the title compound from the acidified reaction mixture gave crude compound (15.42 g), m.p. 245°–246° C. An analytical sample, m.p. 250°–251° C. was obtained from acetone-ethanol solution.

(e) 1-(4-Nitrophenyl)-1,4,5,6-tetrahydro-3-cyclopentapyrazole methanol (Formula VII, $R_1$=4-nitrophenyl, w=1)

A suspension of compound 13(d) (10.0 g) in THF (600 ml) was treated with sodium borohydride (4.96 g) and stirred for 30 minutes. A solution of boron trifluoride ethereate (13.08 ml) was added dropwise during 50 minutes to the mixture at 0° C. Unreacted compound 13(d) was detected after 5 hours and the reaction was allowed to proceed at ambient temperature for 18 hours. The cooled mixture was treated dropwise with 10% aqueous THF. The suspension was diluted to 3 L with water and precipitated title compound was filtered. Crystallization of the precipitate from ethanol-acetate solution gave pure title compound (8.47 g) as two crops. An analytical sample, m.p. 219° C., was obtained from ethanol-ethyl acetate.

(f)
1-(4-Nitrophenyl)-1,4,5,6-tetrahydro-3-cyclopentapyrazole carboxaldehyde (Formula VIII, $R_1$=4-nitrophenyl, w=1)

A solution of compound 13(e) (8.4 g) in toluene (800 ml) was treated with activated manganese dioxide (25.2 g) and azeotropically distilled for 2.5 hours. The hot mixture was filtered, the filtrate evaporated and the residue was crystallized from ethyl acetate-ethanol solution to yield pure title compound (5.57 g), m.p. 209°-210° C.

(g)
6-[1,4,5,6-Tetrahydro-1-(4-nitrophenyl)-3-cyclopentapyrazolyl]-(E)-5-hexenoic acid and -(Z)-5-hexenoic acid methyl esters (Formulas XI and X, $R_1$=4-nitrophenyl, n=3, $M_1$=CH$_3$, w=1)

Dimsyl sodium was generated from 60% sodium hydride (3.84 g) in DMSO (200 ml) at 65° C. Carboxybutyltriphenylphosphonium bromide (21.3 g, 48 mmol) was added to the cooled solution and reacted for one hour. Solid aldehyde (6.22 g, 24 mmol) was added and reacted for 1.5 hours. The solution was poured into ice water and extracted with ether-ethyl acetate to remove neutral products. The filtrate was acidified and extracted into ethyl acetate. The crude acids were esterified with excess ethereal diazomethane and the crude esters (16.0 g) were fractionated on silica gel (1 kg) using 9:1 Skelly B-ethyl acetate (250 ml fractions). After a forerun, the Z-isomer was collected in fractions 4–16 and crystallized from ethanol to yield pure compound, 1.98 g, m.p. 76°-77° C. Fractions 28–49 provide pure E-isomer (2.18 g, m.p. 114°-115° C.).

The intermediate fractions provided 0.2 g of mixed products.

EXAMPLE 14

6-[1-[4-(Acetylamino)-phenyl]-1,4,5,6-tetrahydro-3-cyclopentapyrazolyl]-(E)-5-hexenoic acid methyl ester (Formula XI, $R_1$=4-(Acetylamino)-phenyl, n=3, $M_1$=CH$_3$, w=1)

A solution of the E-isomer of Example 13(g) (0.50 g) in 2:1 THF-methanol (120 ml) was treated with 15% aqueous titanium trichloride (40 ml) and reacted for 45 minutes. The solution was diluted with ice water, neutralized with solid sodium acetate, and extracted with ethyl acetate. The dark residue of 6-[1-[4-aminophenyl]-1,4,5,6-tetrahydro-3-cyclopentapyrazlyl]-(E)-5-hexenoic acid methyl ester (0.44 g) was dissolved in pyridine (10 ml), treated with acetic anhydride (5 ml) and reacted at 25° C. for one hour. The reaction solution was diluted with ice water, the precipitated product was extracted into ethyl acetate, washed, dried and evaporated to yield crude product (0.350 g). Purification on silica gel (50 g) with 30% ethyl acetate in Skelly B gave pure title compound (0.23 g) in fractions 120–130 (20 ml fractions). Crystallization from methylene chloride-ether solution gave the analytical sample, m.p. 118°-120° C.

EXAMPLE 15

6-[1,4,5,6-Tetrahydro-1-(4-nitrophenyl)-3-cyclopentapyrazolyl]-(E)-5-hexenoic acid (Formula XI, $R_1$=4-nitrophenyl, n=3, $M_1$=H, w=1)

A suspension of the E-isomer of Example 13(g) (0.5 g) in methanol (50 ml) and 2N sodium hydroxide was warmed at 45° C. for 1.5 hours. The solution was then reacted at ambient temperature for 18 hours. The solution was diluted with water, acidified, and the precipitate filtered to yield the title compound. Crystallization from ethanol gave pure title compound (0.32 g), m.p. 232°-233° C.

EXAMPLE 16

3-[1,4,5,6-Tetrahydro-1-(4-nitrophenyl)-3-cyclopentapyrazolyl]-(E)-2-propenoic acid (Formula XI, $R_1$=4-nitrophenyl, n=0, $M_1$=H, w=1) Refer to Chart A.

A solution of the aldehyde of Example 13(f) (1.23 g, 4.79 mmol) in pyridine (25 ml) and piperidine (0.1 ml) was treated with malonic acid (2.08 g, 20 mmol) and heated at 75° C. for 2 hours. The solution was concentrated in vacuo, diluted with water (200 ml) and acidified with hydrochloric acid. The precipitate was filtered to yield 1.4 g. Crystallization from ethanol gave pure title compound, 1.2 g, m.p. 315° C. dec.

EXAMPLE 17

6-[1,4,5,6-Tetrahydro-1-(4-nitrophenyl)-3-cyclopentapyrazolyl]-(Z)-5-hexenoic acid (Formula X, $R_1$=4-nitrophenyl, n=3, $M_1$=H, w=1)

A suspension of the Z-isomer of Example 13(g) (0.50 g) in methanol (50 ml) was treated with 2N sodium hydroxide and reacted for 18 hours. The solution was diluted with water, acidified and the precipitate was extracted into ethyl acetate. Evaporation of solvent gave the title compound. Crystallization from ethanol gave pure title comound (0.33 g), m.p. 163°-164° C.

EXAMPLE 18

6-[1-(4-Nitrophenyl)-1,4,5,6-tetrahydro-3-cyclopentapyrazole]-hexanol and
6-[1-(4-nitrophenyl)-1,4,5,6-tetrahydro-3-cyclopentapyrazolyl]-hexanoic acid methyl ester (Formula XIV, $R_1$=4-nitrophenyl, n=3, w=1; Formula XII, $R_1$=4-nitrophenyl, n=3, $M_1$=CH$_3$, w=1) Refer to Chart B.

A solution of the Z-isomer of Example 13(g) (0.63 g) in THF (10 ml) was treated with sodium borohydride (70 mg, 1.85 mmol), cooled to 0° C., and boron trifluoride ethereate (0.37 g, 2.6 mmol) in THF (6 ml) slowly added. The solution was reacted at 0°-5° C. for 18 hours, warmed to ambient temperature and reacted for 9 hours. The mixture was quenched with propionic acid, diluted with water and the reaction products were extracted into ethyl acetate. Drying and evaporation of solvent gave 0.69 g of a 2-product mixture. Fractionation of products from a duplicate preparation on silica gel (100 g) with 85:15 Skelly B-ethyl acetate (20 ml fractions) gave the hexanoic acid methyl ester (0.21 g) in fractions 26–40, m.p. 63°-65° C. Fractions 90–105 provided the hexanol compound (200 mg), m.p. 114°-115° C., after methanol crystallization.

EXAMPLE 19

1-[4-(Acetylamino)-phenyl]-1,4,5,6-tetrahydro-3-cyclopentapyrazole hexanoic acid methyl ester (Formula XII, $R_1$=4-(acetylamino)-phenyl, n=3, $M_1$=$CH_3$, w=1) Refer to Chart B.

A solution of the E-isomer of Example 13(g) (0.35 g) in acetic acid (35 ml) was treated with 10% palladium on carbon and hydrogenated at 40 psi for 2 hours. Catalyst was filtered, the filtrate evaporated, and the residue treated with 5% sodium bicarbonate. The precipitated 4-aminophenylcyclopentapyrazole was extracted into ethyl acetate, dried, and evaporated to a dark oil. The oil was dissolved in pyridine (10 ml), treated with acetic anhydride (5 ml) and reacted for 18 hours. The solution was diluted with water and extracted with ethyl acetate. The extract was washed with 1N hydrochloric acid, dried and evaporated to yield crude product. Purification on silica gel (50 g) with 50% ethyl acetate in Skelly B gave pure title compound, 0.12 g, m.p. 98°–100° C. after ether crystallization.

Reduction acylation of the E-isomer of Example 13(g) (0.35 g) in acetic acid (20 ml), acetic anhydride (20 ml), containing 4-di-methylaminopyridine (30 mg) over 10% palladium on carbon (350 mg) gave the same title product.

EXAMPLE 20

6-[1,4,5,6-Tetrahydro-1-(4-nitrophenyl)-3-cyclopentapyrazolyl]hexanoic acid (Formula XII, $R_1$=4-nitrophenyl, n=3, $M_1$=H, w=1)

A solution of 6-[1-(4-nitrophenyl)-1,4,5,6-tetrahydro-3-cyclopentapyrazolyl]hexanoic acid methyl ester (see Example 18) (0.07 g) in methanol (10 ml) was treated with 2N sodium hydroxide (2 ml) and heated at reflux temperature for 45 minutes. The solution was cooled, evaporated, diluted with water and acidified. The precipitate was extracted into ethyl acetate, washed with 5% saline, dried, and evaporated. The residue was filtered through CC-4 silica gel to remove polar impurities, and the 25% ethyl acetate in hexane effluent gave pure title compound, m.p. 131°–132° C., after ethanol-water recrystallization.

EXAMPLE 21

1-[4-(Acetylamino)-phenyl]-1,4,5,6-tetrahydro-3-cyclopentapyrazole hexanoic acid (Formula XII, $R_1$=4-(acetylamino)-phenyl, n=3, $M_1$=H, w=1)

A solution of the compound of Example 19 (0.13 g) in methanol (7 ml) and 1N sodium hydroxide (3.5 ml) was reacted at 25° C. for 2 hours. The solution was diluted with water, acidified, and the precipitate was extracted into ethyl acetate. The residue from drying and evaporation of solvent was recrystallized from acetonitrile to provide pure title compound (80 mg), m.p. 149°–150° C.

EXAMPLE 22

1-(4-Nitrophenyl)-1,4,5,6-tetrahydro-3-cyclopentapyrazole-3-carboxylic acid ethyl ester (Formula V, $R_1$=4-nitrophenyl, w=1) Refer to Chart A.

A solution of compound 13(c) (1.0 g) in 25% polyphosphoric acid in acetic acid (10 ml) was heated at 130° C. for 3 hours. The solution was diluted with ice water and the precipitate filtered to yield pure title compound (0.58 g). Additional material was recovered by the filtrate by partial neutralization with solid sodium acetate. Crystallization from ethanol provided an analytical sample of title compound, m.p. 180°–181° C.

EXAMPLE 23

6-[1-(4-Chlorophenyl)-1,4,5,6-tetrahydro-3-cyclopentapyrazolyl]-5-hexenoic acid (Formula IX, $R_1$=4-chlorophenyl, n=3, $M_1$=H, w=1) Refer to Chart A.

(a) Bromo[4-chlorophenyl)hydrazono[-acetic acid ethyl ester (Formula III, $R_1$=4-chlorophenyl A mixture of 2-[4-chlorophenyl)hydrazono]-3-oxobutanoic acid ethyl ester (70.0 g, 0.26 mmol) in acetic acid (575 ml) and acetic anhydride (190 ml) containing sodium acetate (52 g) at 0° C. was treated with bromine (13.3 ml, 0.26 mmol) in acetic acid (170 ml) during 50 minutes. The mixture was reacted for one hour, poured into ice water, and vigorously agitated. Storage at 10° C. overnight gave a crystalline precipitate of the title compound. Recrystallization from 80% acetone gave pure title compound (64.74 g), m.p. 132°–134° C.

(b) 1-(4-Chlorophenyl)-1,3a,4,5,6,6a-hexahydro-6a-(1-pyrrolidinyl)-3-cyclopentapyrazole carboxylic acid ethyl ester (Formula IV, $R_1$=4-chlorophenyl, w=1)

A solution of the compound from Example 23(a) (20.06 g, 66 mmol) in toluene (100 ml) was cooled to 0° C. and treated with freshly distilled 1-prrolidino-1-cyclopentene (9.14 g, 9.72 ml, 66 mmol). The solution was treated with triethylamine (6.74 g, 9.28 ml, 66 mmol) in toluene (15 ml) at 0° C. during 1.5 hours. The solution was reacted at ambient temperature for 4.5 hours, diluted with water and extracted with ethyl acetate. Drying and evaporation of solvent gave crude product. Recrystallization from acetonitrile gave pure title compound, m.p. 95°–96° C., indistinguished from the Example 23(a) compound except by iodine staining characteristics on silica gel thin layer chromatography.

(c) 1-(4-Chlorophenyl)-1,4,5,6-tetrahydro-3-cyclopentapyrazolecarboxylic acid ethyl ester (Formula V, $R_1$=4-chlorophenyl, w=1)

A solution of Example 23(b) compound (12.8 g, 35 mmol) in acetic acid (40 ml) and 1N hydrochloric acid (40 ml) was heated at 90°–95° C. for 20 minutes. The solution was cooled, the crystalline precipitate was filtered and washed with water to yield the title compound, 9.4 g. Recrystallization from ethanol provided the analytical sample, m.p. 122.5°–123° C.

(d) 1-(4-Chlorophenyl)-1,4,5,6-tetrahydro-3-cyclopentapyrazole methanol (Formula VII, $R_1$=4-chlorophenyl, w=1)

Lithium aluminum hydride (2.20 g, 58 mmol) in THF (475 ml) was treated with the compound of Example 23(c) (9.5 g, 32 mmol) and reacted for 30 minutes. The suspension was treated with 10% aqueous THF (10 ml), 15% sodium hydroxide (3 ml) and water (25 ml), filtered, and the filter cake was washed with ethyl acetate. The combined filtrates were evaporated to yield the title compound (7.30 g), m.p. 149°–150° C. An analytical sample (m.p. 149°–150° C.) was obtained from ethyl acetate-hexane solution.

(e) 1-(4-Chlorophenyl)-1,4,5,6-tetrahydro-3-cyclopentapyrazolecarboxyaldehyde (Formula VIII, $R_1$=4-chlorophenyl, w=1)

A solution of the compound of Example 23(d) (9.12 g, 36.7 mmol) in methylene chloride (440 ml) was treated with pyridinium dichromate (19.2 g, 55 mmol) and reacted at ambient temperature for 2.5 hours. Additional reagent (4.0 g) was added after 2.5 hours and again (2.0 g) after 4.5 hours. After the final addition the suspension was reacted for two hours, filtered, and the combined filtrate and washes were evaporated to yield 6.51 g of the title compound, m.p. 136°–137° C. Crystallization from hexane gave the analytical sample, m.p. 136°–137° C.

(f) 6-[1-(4-Chlorophenyl)-1,4,5,6-tetrahydro-3-cyclopentapyrazolyl]-5-hexenoic acid (Formula IX, $R_1$=4-chlorophenyl, n=3, $M_1$=H, w=1)

Dimsyl sodium was generated from dimethyl sulfoxide (160 ml) and 60% sodium hydride (4.24 g, 106 mmol) at 60° C. during 4 hours. The solution was cooled to 15° C., 4-carboxybutyltriphenylphosphonium bromide (23.4 g, 52.8 mmol) added, reacted for 30 minutes, and the compound of Example 23(e) (6.5 g, 26.4 mmol) added. Reaction was allowed to proceed for 24 hours, the solution poured into ice water and the precipitate filtered. The alkaline filtrate and water washes were extracted with ether and the aqueous phase was acidified. The precipitate was filtered to yield the title compound (9.22 g), m.p. 146°–147° C. Crystallization from ethanol gave the title compound as a 1:1 E:Z mixture (7.47 g).

IR (mull): 3200–2400, 1700, 1590, 1545, 1490, 1405, 1315, 1285, 1225, 1190, 1085, 1040, 1000, 970, and 920 cm$^{-1}$. NMR (CDCl$_3$) δ: 1.4–2.0, 2.0–3.1, 5.4–6.5, 6.17, 6.40, 7.3–7.8. M.S. m/e 332, 330 (M+), 273, 271 (base peak), and 111.

EXAMPLE 24

1-(4-Chlorophenyl)-1,4,5,6-tetrahydro-3-cyclopentapyrazolo-hexanoic acid methyl ester (Formula XII, $R_1$=4-chlorophenyl, n=3, $M_1$=CH$_3$, w=1) Refer to Chart B.

A solution of the compound of Example 23(f) (1.5 g, 4.5 mmol) in methanolic (50 ml) ethyl acetate (150 ml) at 0° C. was treated with excess ethereal diazomethane and reacted for 30 minutes. Excess reagent was quenched with acetic acid, the solution was diluted with ethyl acetate, washed with 5% sodium bicarbonate, dried and evaporated to yield the methyl esters of the E-Z isomers of the Example 23(f) compound (1.6 g).

The methyl esters were dissolved in ethyl acetate (100 ml), treated with platinum oxide (0.16 g) and hydrogenated at 40 psi for one hour. Catalyst was filtered and the filtrate evaporated to yield the title compound (1.32 g). Crystallization from ethanol gave pure title compound, m.p. 55° C. Sublimation provided the analytical sample, m.p. 55° C.

EXAMPLE 25

1-(4-Chlorophenyl)-1,4,5,6-tetrahydro-3-cyclopentapyrazole-hexanoic acid (Formula XII, $R_1$=4-chlorophenyl, n=3, $M_1$=H, w=1)

A solution of the compound of Example 24 (1.36 g, 3.0 mmol) in methanol (100 ml) was treated with 1N sodium hydroxide (30 ml) and reacted at ambient temperature for 7 hours. The solution was concentrated in vacuo, cooled, diluted with water, and acidified. The precipitate was extracted into ethyl acetate, dried, and evaporated. The residue was crystallized from ethanol to yield pure title compound (0.63 g), m.p. 99°–101° C.

EXAMPLE 26

1-(4-Chlorophenyl)-1,4,5,6-tetrahydro-3-cyclopentapyrazole carboxylic acid (Formula VI, $R_1$=4-chlorophenyl, w=1) Refer to Chart A.

A solution of the compound of Example 23(c) (2.5 g, 8.7 mmol) in methanol (150 ml) was treated with 1N sodium hydroxide (15.4 ml) and heated at reflux temperature for 60 minutes. Reaction was allowed to proceed at ambient temperature, the solution was diluted with water, acidified, and the precipitate filtered to yield title compound. Crystallization from ethyl acetate gave pure title compound (1.77 g) m.p. 220–221.

EXAMPLE 27

1-[(4-Chlorophenyl)-1,4,5,6-tetrahydro-3-cyclopentapyrazolyl]-methoxy-acetic acid (Formula XX, $R_1$=4-chlorophenyl, m=1, $M_1$=H, w=1) Refer to Chart E.

A suspension of 60% sodium hydride (0.26 g, 5.5 mmol) in THF (25 ml) was treated with the compound of Example 23(d) (1.31 g, 5 mmol) and heated at reflux for 3 hours. The mixture was treated with ethyl bromoacetate and reacted for 48 hours. The mixture was treated with 0.2M potassium hydrogen sulfate, and extracted with ethyl acetate. The extracts were dried and evaporated to yield a semi-solid residue (1.79 g) which contained residual compound of Example 23(d).

The crude product was dissolved in methanol (75 ml), treated with 1N sodium hydroxide (30 ml), heated at 95° C. for 5 minutes, and concentrated in vacuo. The concentrate was diluted with water and extracted with ethyl acetate. The alkaline layer was acidified and the precipitate extracted into ethyl acetate. Evaporation of solvent gave pure title compound (0.91 g), m.p. 122°–123° C. after either trituration.

EXAMPLE 28

6-[1-(4-Fluorophenyl)-1,4,5,6-tetrahydro-3-cyclopentapyrazolyl]-5-hexenoic acid (Formula IX, $R_1$=4-fluorophenyl, n=3, $M_1$=H, w=1) Refer to Chart A.

(a) 2-[4-Fluorophenyl)hydrazono]-3-oxo-butanoic acid ethyl ester (Formula II, $R_1$=4-fluorophenyl)

4-Fluoroaniline (33.3 g, 300 mmol) in water (150 ml) was treated with concentrated hydrochloric acid (75 ml) and heated at 90°–95° C. to dissolution. The solution was poured into ice water (250 ml), cooled to −5° C., and treated with a solution of sodium nitrite (20.7 g, 300 mmol) in water (38 ml). The solution was rapidly poured into a solution of ethyl acetoacetate (39 g, 300 mmol) in ethanol (225 ml) and water (1.5 L) containing sodium acetate (75 g, 0.9 mmol). The product precipitated and was stirred at room temperature for 3 hours, filtered, and washed with water. Recrystallization from ethanol gave pure title compound, m.p. 90°–91° C.

(b) Bromo[(4-fluorophenyl)hydrazono]-acetic acid ethyl ester (Formula III, $R_1$=4-fluorophenyl)

A solution of the compound of Example 28(a) (65.6 g, 260 mmol) in glacial acetic acid (575 ml) and acetic anhydride (190 ml) was treated with sodium acetate (52 g) and cooled to 2° C. The suspension was treated with bromine (13.3 ml, 260 mmol) during 60 minutes and reacted for 1.5 hours. The mixture was poured into ice water (1.5 L) and stirred for 20 hours at 10° C. The yellow precipitate was filtered and crystallized from hexane to yield the title compound (43.5 g), m.p. 99°–100° C.

(c) 1-(4-Fluorophenyl)-1,4,5,6-tetrahydro-3-cyclopentapyrazolecarboxylic acid ethyl ester (Formula V, $R_1$=4-fluorophenyl, w=1)

A solution of the compound of Example 28(b) (28.9 g, 100 mmol) in toluene (175 ml) was cooled to 0° C. and a solution of pyrrolidino-cyclopentene (14.6 ml, 13.7 g, 100 mmol) in toluene (25 ml) containing triethylamine (13.9 ml, 10.1 g, 100 mmol) was added. The solution was reacted at 0° C. for 1.5 hours then at ambient temperature for 18 hours. The solution was diluted with water, extracted with ethyl acetate, dried and evaporated to yield 1-(4-fluorophenyl)-1,3a,4,5,6,6a-hexahydro-6a-(1-pyrrolidinyl)-3-cyclopentapyrazole carboxylic acid ethyl ester of Formula IV (55 g) as a viscous oil.

Without purification the above obtained ethyl ester was dissolved in acetic acid (165 m), treated with 1N hydrochloric acid (165 ml), heated at 90°–95° C. for 20 minutes, cooled, and treated with 1N hydrochloric acid (165 ml). The product precipitated as a crystalline mass, was filtered, and washed with water to yield title compound. Additional title compound (1.34 g) was obtained from the filtrate after heating for 30 minutes.

(d) 1-(4-Fuorophenyl)-1,4,5,6-tetrahydro-3-cyclopentapyrazolemethanol (Formula VII, $R_1$=4-fluorophenyl, w=1)

Lithium tetrahydridoaluminate (2.28 g, 60 mmol) in THF (475 ml) was treated with the compound of Example 28(c) (8.23 g, 30 mmol) and reacted for 10 minutes. The reaction mixture was quenched with water and 15% sodium hydroxide, the precipitate filtered, and the filter cake was washed with ethyl acetate. The combined filtrate was evaporated and the residue crystalized from ethanol to yield the title compound (4.47 g) m.p. 77°–78° C. A sample was sublimed for analysis.

(e) 1-(4-Fluorophenyl)-1,4,5,6-tetrahydro-3-cyclopentapyrazolecarboxaldehyde (Formula VIII, $R_1$=4-fluorophenyl, w=1)

A solution of the compound of Example 28(d) (9.61 g, 41.4 mmol) in methylene chloride (450 ml) was treated with pyridinium dichromate (25.22 g, 72.5 mmol) and reacted at ambient temperature for 6 hours. The suspension was filtered, the combined filtrate and washes were filtered through silica gel (300 g) using 3:1 methylene chloride-ethyl acetate as effluent. The effluent was evaporated and recrystallized to yield pure title compound (5.2 g), m.p. 123°–125° C. Alternatively, manganese oxidation of 1 (1.16 g) in methylene chloride at reflux temperature for 72 hours gave pure title compound (0.99 g), m.p. 122°–123° C.

(f) 6-[1-(4-Fluorophenyl)-1,4,5,6-tetrahydro-3-cyclopentapyrazolyl]5-hexenoic acid (Formula IX, $R_1$=4-fluorophenyl, n=3, $M_1$=H, w=1)

Dimsyl sodium was prepared from dimethyl sulfoxide (150 ml) and 60% sodium hydride (3.54 g, 88.7 mmol) at 62° C. for 3 hours. The solution was cooled to 18° C. and 4-carboxybutyltriphenylphosphonium bromide (19.6 g, 44.3 mmol) added in portions. The solution was reacted for 30 minutes at 25° C. and treated with the compound of Example 28(e) (5.2 g, 22.6 mmol). Reaction was complete after 45 minutes and was poured into ice water. The precipitate was filtered from the alkaline solution and the combined filtrate and water washed were acidified and the precipitated acids extracted into ethyl acetate. Drying and evaporation of solvent gave a residue of crude title compound. Purification on CC-4 silica gel (400 g) with 1:1 ethyl acetate-Skelly B eluent gave 4.23 g of title compound. Crystallization from ethanol gave the E-Z isomers of the title compound (1.91 g), m.p. 124°–125° C.

EXAMPLE 29

6-[(4-Fluorophenyl)-1,4,5,6-tetrahydro-3-cyclopentapyrazolyl]5-hexenoic acid methyl ester (Formula IX, $R_1$=4-fluorophenyl, n=3, $M_1$=$CH_3$, w=1)

A solution of the compound of Example 28(f) (1.38 g, 44 mmol) in methanol (30 ml) and ethyl acetate (30 ml) at 0° C. was treated with excess ethereal diazomethane. Excess reagent was quenched with acetic acid, the solution was washed with 5% sodium bicarbonate solutions, dried and evaporated. The residue deposited the title compound (1.43 g), m.p. 67°–68° C., from hexane solution.

EXAMPLE 30

1-(4-Fluorophenyl)-1,4,5,6-tetrahydro-3-cyclopentapyrazole-hexanoic acid methyl ester (Formula XII, $R_1$=4-fluorophenyl, n=3, $M_1$=$CH_3$, w=1) Refer to Chart B.

A solution of the compound of Example 29 (0.90 g, 2.7 mmol) in ethyl acetate (100 ml) was treated with platinum oxide (0.4 g) and reduced for 3 hours at atmospheric pressure. The catalyst was filtered, the filtrate evaporated and the residue (0.87 g) was crystallized from hexane to yield the title compound, m.p. 39°–40° C.

EXAMPLE 31

1-(4-Fluorophenyl)-1,4,5,6-tetrahydro-3-cyclopentapyrazole-hexanoic acid (Formula XII, $R_1$=4-fluorophenyl, n=3, $M_1$=H, w=1)

A solution of the compound of Example 30 (1.3 g, 4 mmol) in methanol (120 ml) was treated with 1N sodium hydroxide (40 ml) and reacted at ambient temperature for 7 hours. The solution was concentrated, cooled, and acidified. The precipitate was extracted into ethyl acetate, dried and evaporated. The residue was crystallized from ethanol to yield pure title compound (1.03 g), m.p. 64°–67° C.

EXAMPLE 32

1-(4-Fluorophenyl)-1,4,5,6-tetrahydro-3-cyclopentapyrazole-hexanol (Formula XIV,
$R_1$=4-fluorophenyl, n=3, w=1) Refer to Chart B.

Lithium tetrahydridoaluminate (0.345 g, 9.1 mmol) in THF (75 ml) was treated with the compound of Example 31 (1.0 g, 3.1 mmol) and the mixture was heated at 60° C. for 2 hours. Excess reagent was quenched, the mixture filtered and the combined filtrate and ethyl acetate washes were evaporated to a colorless oil (0.76 g). Polar impurities were removed on silica gel (40 g) with 1:1 ethyl acetate-Skelly B eluent to provide title compound (0.42 g) as an oil.

EXAMPLE 33

1-(4-Fluorophenyl)-1,4,5,6-tetrahydro-3-cyclopentapyrazole carboxylic acid (Formula VI,
$R_1$=4-fluorophenyl, w=1) Refer to Chart A.

A solution of the compound of Example 28(c) (2.50 g, 9 mmol) in methanol (150 ml) was treated with 1N sodium hydroxide (18 ml). After 30 minutes at ambient temperature a precipitate formed and failed to redissolve during 18 hours. The precipitate was filtered to yield the methyl ester of the title compound. The precipitate was added to the filtrate, heated at reflux temperature for 60 minutes, diluted with water, and the solution was acidified. The precipitate was extracted in ethyl acetate, dried, and evaporated. The residue was crystallized from ethyl acetate to yield the title compound, m.p. 214°–215° C. An analytical sample was recrystallized from ethanol.

EXAMPLE 34

6-(1-Phenyl-1,4,5,6-tetrahydro-3-cyclopentapyrazolyl)-5-hexenoic acid (Formula IX, $R_1$=phenyl, n=3, $M_1$=H, w=1) Refer to Chart A.

(a) 2(Phenylhydrazono)-3-oxo-butanoic acid ethyl ester (Formula II, $R_1$=phenyl)

A solution of aniline (37.2 g, 0.4 mmol) in water (32 ml) and concentrated hydrochloric acid (100 ml) was poured into ice (400 g). The 0° C. solution was treated with a solution of sodium nitrite (27.6 g, 0.4 mmol) in water (50 ml). The diazonium salt solution was poured rapidly into a stirred solution of ethyl acetoacetate (52 g, 0.4 mmol) in ethanol (300 ml) and ice water (1.0 L) containing sodium acetate (100 g, 1.2 mmol). Th mixture was stirred at 0° C. for 2.5 hours, filtered, and the filter cake was crystallized from ethanol to yield the title compound (75.2 g), m.p. 75°–76° C. (lit 61°–64° C.).

(b) Bromo(phenylhydrazono)-acetic acid ethyl ester (Formula III, $R_1$=phenyl)

A solution of the compound of Example 34(a) (74.2 g, 316 mmol) in acetic acid (580 ml) and acetic anhydride (200 ml) containing sodium acetate (55 g) at 0° C. was treated dropwise with a solution of bromine (14.1 ml, 316 mmol) in acetic acid (175 ml). The mixture was reacted at 0° C. for 60 minutes, poured into water (1.5 L) and stirred for 18 hours at 10° C. The precipitate was filtered, washed with water, and recrystallized from ethanol to provide pure title compound (45.8 g), m.p. 82°–83° C. (lit m.p. 82°–83° C.).

(c) 1-Phenyl-1,4,5,6-tetrahydro-3-cyclopentapyrazole carboxylic acid ethyl ester (Formula V, $R_1$=phenyl, w=1)

A solution of the compound of Example 34(b) (27.1 g, 100 mmol) in toluene (175 ml) was cooled to 0° C. and a solution of cyclopenteno-pyrrolidine (13.7 g, 14.6 ml, 100 mmol) in toluene (25 ml) and triethylamine (10.1 g, 13.9 ml, 100 mmol) added slowly. The solution was reacted at 0° C. for 90 minutes, then at ambient temperature for 2 hours. The solution was diluted with water and extracted with ethyl acetate to yield 1-phenyl-1,3a,4,5,6,6a-hexahydro-6a-(1-pyrrolidinyl)-3-cyclopentapyrazole carboxylic acid ethyl ester of Formula IV (34 g), as an oil.

Without attempted purification the crude ethyl ester was dissolved in acetic acid (100 ml), treated with 1N hydrochloric acid (150 ml) and heated at 90°–95° C. for 30 minutes. The solution was poured into ice water, the precipitate filtered and crystallized from ethanol to yield the title compound (20.4 g), m.p. 156°–157° C.

(d) 1-Phenyl-1,4,5,6-tetrahydro-3-cyclopentapyrazole methanol (Formula VII, $R_1$=phenyl, w=1)

A suspension of lithium tetrahydroaluminate (7.34 g, 194 mmol) in THF (500 ml) was treated with the compound of Example 34(c) (25.1 g, 97 mmol) and heated at 50° C. for 12 hours. The excess reagent was quenched, the mixture filtered, the filtrate and ethyl acetate washes were combined, and evaporated. The residue was crystallized from toluene to yield pure title compound (15.2 g), m.p. 94°–95° C.

(e) 1-Phenyl-1,4,5,6-tetrahydro-3-cyclopentapyrazole carboxaldehyde (Formula VIII, $R_1$=phenyl, w=1)

A solution of the compound of Example 34(d) (5.0 g, 23 mmol) in methylene chloride (100 ml) was treated with activated manganese dioxide (1.0 g) and heated at reflux. Additional reagent (15 g) was added in 0.5 g aliquots during 7 days. The mixture was diluted with ethyl acetate, filtered, and the combined filtrate and ethyl acetate washes were evaporated to yield the title compound (3.8 g). Crystallization from hexane gave pure title compound (3.2 g), m.p. 111°–112° C.

Alternatively, a solution of the compound of Example 34(d) (8.87 g, 41.4 mmol) in toluene (250 ml) with manganese dioxide (17.74 g) was azeotropically distilled during 6 hours. The suspension was filtered, the filtrate evaporated to yield the title compound (8.3 g). Crystallization from methylene chloride hexane gave pure title compound (6.7 g), m.p. 108°–109° C.

(f) 6-(1-Phenyl-1,4,5,6-tetrahydro-3-cyclopentapyrazolyl)-5-hexenoic acid (Formula IX, $R_1$=phenyl, n=3, $M_1$=H, w=1)

Dimsyl sodium was prepared from 60% sodium hydride (1.28 g, 32 mmol) in dimethylsulfoxide (50 ml) at 60°–65° C. during 3 hours. The solution was cooled and treated with 4-carboxybutyltriphenylphosphonium bromide (7.0 g, 16 mmol) and reacted at ambient temperature for 30 minutes. The solution was treated with the compound of Example 34(e) (1.7 g, 8 mmol) and reacted for 30 minutes. The solution was diluted with 300 ml of ice water and extracted with ethyl acetate. The aqueous layer was acidified and the precipitate extracted into ethyl acetate. Drying and evaporation of solvent gave a semi-solid residue (5.4 g). Fractionation on CC-4 silica gel with 1:1 ethyl acetate-methylene chloride (20 ml fractions) gave the title compound (0.45 g), m.p. 130°–131° C. after ethanol crystallization.

EXAMPLE 35

(E)-1,4,5,6-Tetrahydro-1-phenyl-3-cyclopentapyrazol-3-yl)-5-hexenoic acid and (Z)-6-(1,4,5,6-tetrahydro-1-phenyl-3-cyclopentapyrazol-3-yl-5-hexenoic acid (Formulas XI and X, $R_1$=phenyl, n=3, $M_1$=H, w=1) Refer to Chart A.

The total acidic product (11.0 g) from Wittig reaction of the compound of Example 34(e) (3.4 g, 16 mmol) with the ylide from carboxybutyltriphenylphosphonium bromide (14.0 g, 32 mmol) in toluene was purified on silica gel (800 g) using 10% ethyl acetate in Skelly B as eluent (20 ml fractions) eluted pure title compound Z-isomer (1.24 g). Continued elution with 1:1 ethyl acetate-Skelly B containing 5% ethyl acetate (500 ml fractions) gave additional title compound Z-isomer (2.25 g), 1:1 mixture (1.98 g) of the title compound E and Z isomers. Trituration of the residues (3.49 g) of isomer mixture hexane gave pure title compound Z-isomer (2.05 g), m.p. 114°–115° C. The crystallization filtrate and mixtures were refractionated on CC-4 silica gel (175 g) with 9:1 Skelly B-ethyl acetate (20 ml fractions). Fractions 1–10 gave additional Z-isomer (0.88 g), fractions 11–30 gave pure E-isomer (1.6 g), m.p. 140°–141° C.

EXAMPLE 36

5-(1,4,5,6-Tetrahydro-phenyl-3-cyclopentapyrazolyl)-Z-4-pentenoic acid methyl ester and -(E)-4-pentenoic acid methyl ester (Formulas XI and X, $R_1$=phenyl, n=2, $M_1$=$CH_3$, w=1) Refer to Chart A.

Dimsyl sodium was prepared from 60% sodium hydride (1.3 g, 32 mmol) in DMSO (65 ml) at 65° C. The solution was cooled to insipient freezing and 3-carboxypropyltriphenylphosphonium bromide (6.8 g, 16 mmol) added. The ylide was allowed to form during 30 minutes at ambient temperature. The aldehyde of Example 34(e) (5.50 g, 25.9 mmol) was added and reaction was allowed to proceed for 17 hours. The solution was poured into water (400 ml) and neutral products extracted into ethyl acetate. The aqueous phase was acidified and the precipitate extracted into ethyl acetate. The residue (7.1 g) from solvent evaporation was esterified in methanolethyl acetate solution with excess etheral diazomethane to yield 5.20 g of crude esters. Fractionation on silica gel (600 g), collecting 20 ml fractions gave pure Z-isomer title compound and E-isomer title compound (1.80 g). Both esters were oils.

Z isomer:
NMR ($CDCl_3$), δ: 2.53, 2.87, 3.60, 5.86, 6.43, 7.0–7.8. M.S. m/e 296 (M+), 281, 265, 237, and 223. UV (ethanol) 281 (ε 18,000)nm.

E-isomer:
NMR ($CDCl_3$) δ: 2.3–3.0, 3.62, 6.05, 6.51, 6.9–7.6. M.S. m/e 296 (M+), 281, 265, 237, 223. UV (ethanol) 238 (ε 12,500), 281 (ε 22,400) nm.

EXAMPLE 37

3-(7-Hepten-6-yl)-1-phenyl-1,4,5,6-tetrahydro-cyclopentapyrazole (Formula XVII, $R_1$=phenyl, n=4, w=1)

Dimsyl sodium was prepared from 60% sodium hydride (1.3 g, 32 mmol) in DMSO (50 ml) at 60°–65° C. Hexyl triphenylphosphonium bromide (12.8 g, 30 mmol) was added and reacted for 30 minutes. The aldehyde of Example 34(e) (2.5 g, 11.8 mmol) was added, reacted at ambient temperature for 1.25 hours, and the reaction was quenched with ice water (300 ml). The precipitate was extracted into ethyl acetate, washed with 5% sodium chloride solutions, dried, and evaporated. The residue (11.2 g) was filtered through silica gel (350 g) and the 9:1 Skelly B-ethyl acetate effluent collected to provide the title compound (2.70 g), an oil.

IR (film): 1600, 1565, 1510, 1465, 1445, 1385, 1330, 1300, 1270, 1165, 1120, 1075, 1055, 1030, 970, 900 and 760 cm$^{-1}$.

NMR ($CDCl_3$) δ: 0.88, 1.1–1.8, 2.0–2.8, 2.90, 5.5–6.8, 7.0–7.8. MS m/e 380 (M+), 265, 251, 237.

EXAMPLE 38

3-(7-Heptyl)-1-phenyl-1,4,5,6-tetrahydro-cyclopentapyrazole (Formula XIII, $R_1$=phenyl, n=3, w=1)

A solution of the compound of Example 37 (0.41 g) in ethyl acetate (60 ml) was treated with $PtO_2$ (0.25 g) and hydrogenated at 40 psi for 3 hours. Catalyst was filtered to provide impure title compound (0.22 g). Purification on silica gel with 1% ethyl acetate in Skelly B gave pure title compound (0.17 g) as an oil.

IR (film): 1600, 1565, 1510, 1500 (sh), 1470, 1390, 1300, 1120, 1090, 1065, 1050, 1025 and 755 cm$^{-1}$.

NMR ($CDCl_3$) δ: 0.8, 1.1–1.8, 2.4–2.7, 2.93, 7.0–7.7. MS/ m/e 282 (M+), 267, 253, 225 and 198.

EXAMPLE 39

8-(1,4,5,6-Tetrahydro-1-phenyl-3-cyclopentapyrazolyl)-(Z)-7-octenoic acid and 8-(1,4,5,6-tetrahydro-1-phenyl-3-cyclopentapyrazolyl)-(E)-7-octenoic acid (Formulas X and XI, $R_1$=phenyl, n=5, $M_1$=H, w=1) Refer to Chart A.

Dimsyl sodium was prepared with 60% sodium hydrode (2.56 g, 64 mmol) in DMSO (128 ml) at 60°–65° C. The solution was cooled, treated with 6-carboxyhexyltriphenylphosphonium bromide (15.07 g, 32 mmol) and reacted for 45 minutes. The ylide solution was treated with the compound of Example 34(e) (3.4 g, 16 mmol) and reacted for 18 hours. The solution was diluted with water, the alkaline mixture extracted with ether, and the aqueous phase was acidified. The crude precipitate was extracted into ether, washed with 5% brine solution, dried and evaporated. The residual oil (12.6 g) was purified on CC-4 silica gel (700 g). The first eluted (1:9 ethyl acetate-Skelly B) product gave the Z-isomer title compound (3.6 g), the intermediate fraction gave mixed products (1.1 g), and the final eluate gave pure E-isomer title compound (0.60 g). Analytical sample of the Z-isomer title compound, m.p. 88°–90° C. and the E-isomer title compound, m.p. 86°–88° C. were obtained from methylene chloride-hexane solution.

EXAMPLE 40

1,4,5,6-Tetrahydro-1-phenyl-3-cyclopentapyrazole octanoic acid (Formula XII, $R_1$=phenyl, n=5, $M_1$=H, w=1) Refer to Chart B.

A solution of the Z-isomer of Example 39 (0.80 g) in ethyl acetate (50 ml) was treated with $PtO_2$ (0.15 g) and reduced at 40 psi hydrogen pressure for 2 hours. Catalyst was filtered and the filtrate evaporated to a viscous residue (0.68 g). Crystallization of the residue gave pure title compound (0.60 g), m.p. 55°–57° C.

EXAMPLE 41

[(1,4,5,6-Tetrahydro-1-phenyl-3-cyclopentapyrazolyl)-thiomethyl]propionic acid (Formula XXII, $R_1$=phenyl, m=2, $M_1$=H, w=1) Refer to Chart E.

(a)

3-Chloromethyl-1,4,5,6-tetrahydro-1-phenyl-cyclopentapyra-zole (Formula XXI, $R_1$-phenyl, w=1)

A solution of the compound of Example 34(d) (6.50 g, 30 mmol) in chloroform (60 ml) at 0° C. was treated with pyridine (6.4 ml) and a solution of thionylchloride (5.47 ml) in methylene chloride (40 ml). The solution was reacted at 0° C. for 1.5 hours, then at ambient temperature for 18 hours. The mixture was poured onto ice, the organics partitioned, washed with 5% brine, 5% bicarbonate and 1N hydrochloric acid solutions, dried and evaporated. The residue (8.1 g) was filtered through silica gel to remove polar impurities and the effluent residue (3.4 g) was crystallized from hexane to yield the title compound, m.p. 84°–85° C.

(b)

[(1,4,5,6-Tetrahydro-1-phenyl-3-cyclopentapyrazolyl)-thiomethyl]-propionic acid (Formula XXII, $R_1$=phenyl, m=2, $M_1$=H, w=1)

Methyl-3-mercaptopropionate (0.069 g) in DMF (5 ml) was treated with triethylamine (0.58 g) and reacted for 15 minutes. The solution was treated with a compound of Example 41(a) and reacted for 3.5 hours. Without purification, the intermediate ester was hydrolyzed by the addition of 2N sodium hydroxide and soaponification for one hour at ambient temperature. The solution was diluted with water, washed with ether, and the aqueous phase was acidified. The precipitate was filtered to yield the title compound (0.44 g). An analytic sample was obtained from acetonitrile, m.p. 94°–95° C.

EXAMPLE 42

[(1,4,5,6-Tetrahydro-1-phenyl-3-cyclopentapyrazolyl)-methyl-thio] acetic acid methyl ester (Formula XXII, $R_1$=phenyl, m=1, $M_1$=CH$_3$, w=1) Refer to Chart E.

A solution of the compound of Example 41(a) (0.81 g, 3.3 mmol) in DMF (5 ml) was treated with methyl 2-mercaptoacetate (0.46 ml, 0.61 g, 5.7 mmol), triethylamine (0.79 ml) was added, and the solution was reacted at ambient temperature for 20 hours. The solution was poured into ice water and product extracted into ethyl acetate. Evaporation of solvent gave crude methyl ester of the title compound as an oil (1.12 g).

Without purification, crude methyl ester of the title compound in methanol (75 ml) was hydrolyzed with 1N sodium hydroxide (20 ml) during 1.5 hours. The solution was concentrated, diluted with water, and acidified. Precipitated title compound was filtered and crystallized to yield 0.72 g, m.p. 118°–119° C.

EXAMPLE 43

1-Phenyl-1,4,5,6-tetrahydro-3-cyclopentapyrazolyl methoxy acetic acid (Formula XX, m=1, $M_1$=H, w=1) Refer to Chart E.

A solution of 1-phenyl-1,4,5,6-tetrahydro-3-cyclopentapyrazolemethanol (2.14 g, 10 mmol) in THF (40 ml) was cooled to −10° C. and treated with 1.6M n-butyl lithium (6.2 ml, 10 mmol) using bipyridyl indicator. After 20 minutes, ethyl bromoacetate (1.9 g, 1.26 ml, 11.4 mmol) was added, reached at −20° C. for 45 minutes, then at ambient temperature for 18 hours. The solution was poured into ice water, acidified, and the products extracted into ethyl acetate. Drying and evaporation of solvent gave a residue containing unreacted methanol starting material. The residue was soaponified in methanol (150 ml) with 2N sodium hydroxide (25 ml) for 2 hours. The solution was concentrated to 50 ml, diluted to 300 ml with water, and neutral products extracted into ethyl acetate. The alkaline solution was acidified and extracted with ethyl acetate to yield crude title compound. Purification on CC-4 silica gel (100 g) with 1:1 ethyl acetate-Skelly B eluent gave pure title compound. Crystallization from ethyl acetate provided title compound (0.50 g), m.p. 106°–107° C.

EXAMPLE 44

3-(1,4,5,6-Tetrahydro-1-phenyl-3-cyclopentapyrazolyl)-2-propenoic acid methyl ester (Formula IX, $R_1$=phenyl, n=0, $M_1$=CH$_3$, w=1) Refer to Chart A.

A solution of the compound of Example 34(e) (1.06 g) in ethanol (25 ml) was treated with malonic acid (0.52 g) and ammonium acetate (0.77 g). The solution was heated at reflux temperature for 24 hours and evaporated. The residue was dissolved in methanol and esterified with excess ethereal diazomethane. The crude product (1.76 g) was filtered through silica gel (100 g) and the filtrate evaporated to yield the title compound (0.66 g). Crystallization from ethanol provided the analytical sample, m.p. 147°–148° C.

EXAMPLE 45

3-(1,4,5,6-Tetrahydro-1-phenyl-3-cyclopentapyrazolyl)-2-propenoic acid (Formula IX, $R_1$=phenyl, n=0, $M_1$=H, w=1) Refer to Chart A.

A solution of the compound of Example 34(e) (1.20 g, 5.7 mmol) in pyridine (15 ml) was treated with malonic acid (2.35 g, 22.6 mmol) and piperidine (0.22 ml, 0.192 g) and heated at 90°–95° C. for 28 hours. The residue from solvent evaporation was suspended in water (200 ml), treated with 1N hydrochloric acid, and the solid filtered. Crystallization from ethyl acetate-hexane gave pure title compound (1.35 g), m.p. 223° C.

EXAMPLE 46

3-(1,4,5,6-Tetrahydro-1-phenyl-3-cyclopentapyrazole)-propanoic acid (Formula XII, $R_1$=phenyl, n=0, $M_1$=H, w=1) Refer to Chart B.

A solution of the compound of Example 45 (0.50 g) in acetic acid (30 ml) was treated with platinum oxide (0.20 g) and reduced at 40 psi hydrogen pressure for 2 hours. Catalyst was filtered, the filtrate evaporated and the residue was triturated with water to yield the title compound. Crystallization from ethanol gave pure title compound, m.p. 134°–135° C.

EXAMPLE 47

5-(1,4,5,6-Tetrahydro-1-phenyl-3-cyclopentapyrazolyl)-(E)-4-pentenoic acid (Formula XI, $R_1$=phenyl, n=2, $M_1$=H, w=1)

A solution of the E-isomer of Example 36 (1.5 g, 5.1 mmol) in methanol (75 ml) and 1N sodium hydroxide (25 ml) were reacted for 18 hours at ambient temperature. The solution was concentrated, diluted with water, and acidified. The precipitate was filtered to provide 1.43 g; crystallization from ethanol gave pure title compound, m.p. 133°–134° C.

EXAMPLE 48

5-(1,4,5,6-Tetrahydro-1-phenyl-3-cyclopentapyrazolyl)-(Z)-4-pentenoic acid (Formula X, $R_1$=phenyl, n=2, $M_1$=H, w=1)

A solution of the Z-isomer of Example 36 (1.0 g, 3.4 mmol) in methanol (50 ml) was treated with 1N sodium hydroxide (17 ml) and reacted for 24 hours. The solution was concentrated to 20 ml, diluted with ice water, and acidified. The precipitate was filtered to yield the title compound (0.96 g). Crystallization from ethanol-water gave pure title compound (0.80 g), m.p. 122°–125° C.

EXAMPLE 49

1-Phenyl-1,4,5,6-tetrahydro-3-cyclopentapyrazole hexanoic acid (Formula XII, $R_1$=phenyl, n=3, $M_1$=H, w=1) Refer to Chart B A solution of the compound of Example 34(f) (0.25 g, 0.8 mmol) in chloroform (50 ml) was treated with platinum oxide (0.10 g) and reduced at 40 psi of hydrogen for one hour. The catalyst was filtered, the filtrate evaporated to a non-crystalline residue. Crystallization from either acetonitrile or 3:1 methanol-water gave the title compound, m.p. 95°–96° C.

EXAMPLE 50

1,4,5,6-Tetrahydro-1-phenyl-3-cyclopentapyrazole pentanoic acid (Formula XII, $R_1$=phenyl, n=2, $M_1$=H, w=1) Refer to Chart B A solution of the crude esters produced in Example 36 (1.1 g, 3.9 mmol) in ethyl acetate (100 ml) was treated with platinum oxide (0.35 g) and reduced at 40 psi hydrogen pressure during 3 hours. Catalyst was filtered and the filtrate evaporated to yield crude methyl ester of the title compound (1.0 g) as an oil, which was dissolved in methanol (50 ml), treated with 1N sodium hydroxide (28 ml) and reacted at ambient temperature for 4 hours. The solution was concentrated, diluted with water and acidified. The precipitate was extracted into ethyl acetate, dried, and evaporated to a solid residue. Crystallization from ethanol-water gave pure title compound (0.46 g), m.p. 98°–99° C.

EXAMPLE 51

6(1-Benzyl-1,4,5,6-tetrahydro-3-cyclopentapyrazolyl)-hexanoic acid (Formula XII, $R_1$=benzyl, n=3, $M_1$=H, w=1) Refer to Charts D, A and B (a) 1-Benzyl-1,4,5,6-tetrahydro-3-cyclopentapyrazole carboxylic acid ethyl ester (Formula V, $R_1$=benzyl, w=1)

A solution of Formula XIX (3.68 g, 20 mmol) in ethanol (70 ml) was treated with benzylhydrazine 2HCl (3.9 g, 20 mmol) and the solution was heated at reflux temperature for 22 hours. The residue from solvent concentration was diluted with water, products extracted into ethyl acetate, and the extracts were washed with 5% brine solution. Drying and evaporation of solvent gave a semi-solid residue (5.22 g) containing 4 products. Two products (i, j) 1.28 g, were deposited from ethanol. The residue from evaporation of the ethanol filtrate was fractionated on silica gel (200 g) using 15% ethyl acetate in Skelly B as eluent (20 ml fractions).

Fractions 105–130 (25% ethyl acetate eluent) gave the title compound (2.23 g).

IR (film): 2950–2750, 1720:, 1515, 1495, 1480, 1455, 1380, 1355, 1300, 1240, 1110, 1030, 790, 755 and 705 cm$^{-1}$.

NMR (CDCl$_3$): 1.33, 2.43, 2.73, 4.33, 5.23, 7.23. MS m/e 270 (M+), 241, 225, 198, 197, 196, 179, 91 (base peak).

(b) 1-Benzyl-1,4,5,6-tetrahydro-3-cyclopentapyrazole methanol (Formula VII, $R_1$=benzyl, w=1)

A solution of 1-benzyl-1,4,5,6-tetrahydro-3-cyclopentapyrazole carboxylic acid ethyl ester (6.0 g, 2.22 mmol) in THF (125 ml) was treated with lithium aluminum hydride (1.73 g, 44.4 mmol) and reacted at ambient temperature for 3.5 hours. Excess reagent was quenched with 10% aqueous THF (18 ml), 15% sodium hydroxide (5.4 ml) and water (5.4 ml). The mixture was diluted with ethyl acetate and filtered. The filtrate was washed with 5% brine solutions, dried, and evaporated to provide the title compound (5.40 g) as an oil.

(c) 1-Benzoyl-1,4,5,6-tetrahydro-3-cyclopentapyrazole carboxaldehyde (Formula VIII, $R_1$=benzyl, w=1)

A solution of the compound of Example 5(b) (5.0 g, 20.5 mmol) in toluene (300 ml) was treated with activated manganese dioxide (15 g) and azeotropically distilled for 4 hours. The cooled solution was filtered and evaporated to yield crude title compound (3.09 g). Filtration through silica gel removed polar contaminants and provided pure title compound (2.16 g) as an oil.

(d) 6-(1-Benzyl-1,4,5,6-tetrahydro-3-cyclopentapyrazole)-5Z-hexenoic acid and 6-(1-Benzyl-1,4,5,6-tetrahydro-3-cyclopentapyrazole)-5E-hexenoic acid (Formulas X and XI, $R_1$=benzyl, n=3, $M_1$=H, w=1)

Dimsylsodium was prepared from 60% sodium hydride (1.40 g, 3.2 mmol) in DMSO (70 ml) at 60°–65° C. for 3.5 hours. The cooled solution was treated with 4-carboxybutyltriphenylphosphonium bromide (7.84 g, 17.7 mmol) and reacted at room temperature for 30 minutes. The solution was treated with the compound of Example 51(c) (2.0 g, 8.8 mmol) and reacted for 18 hours. The reaction solution was poured into ice water and neutral products were extracted into methylene chloride. The aqueous phase was acidified and the oily precipitate was extracted into 1:1 ether-ethyl acetate. Drying and evaporation of solvent gave 3.90 g of mixed products. The isomers were separated on CC-4 silica gel (200 g) collecting 20 ml fractions of 15% ethyl acetate in Skelly B eluent. Fractions 90–189 provided the Z-isomer title compound (0.62 g), m.p. 94°–95° C., after methylene chloride-ethyl acetate crystallization. Fractions 190–350 gave the E-isomer title compound (0.22 g), m.p. 133°–134° C., after crystallization from ethanol.

(e) 6(1-Benzyl-1,4,5,6-tetrahydro-3-cyclopentapyrazolyl)-hexanoic acid (Formula XII, $R_1$=benzyl, n=3, $M_1$=H, w=1)

A solution of the Z-isomer of Example 51(d) (0.103 g) in ethanol (50 ml) was treated with 10% palladium on carbon (0.10 g) and hydrogenated at atmospheric pressure for one hour. The catalyst was filtered, the filtrate evaporated, and the residue crystallized from acetonitrile to yield the title compound, m.p. 94°–95° C.

EXAMPLE 52

1-(4-Bromophenyl)-4,5,6,7-tetrahydro-1H-indazole-3-carboxylic acid (Formula VI, $R_1$=4-bromophenyl, w=2) Refer to Chart A (a) 2-[(4-Bromophenyl)hydrazone]-3-oxo-butyric acid ethyl ester (Formula II, $R_1$=4-bromophenyl)

A suspension of 4-bromoaniline (68.8 g) in water (32 ml) was treated with concentrated hydrochloric acid (100 ml) and heated for 30 minutes. The suspension was treated with ice (400 ml) and maintained at 0° C. while a solution of sodium nitrite (27.6 g) in water (50 ml) was added.

The diazonium salt solution was added in one portion to a solution of ethyl acetoacetate (52 g) in ethanol (300 ml) and sodium acetate (100 g) in ice water (1L). The suspension was agitated for 3 hours at 0° C. and product was filtered. Crystallization of the precipitate from ethanol provided 107.7 g of the title compound, m.p. 102°–104° C.

(b) Bromo-(4-bromophenyl)-hydrazono-acetic acid ethyl ester (Formula III, $R_1$=4-bromophenyl)

A suspension of the compound of Example 52(a) (81.4 g) in acetic acid (575 ml) and acetic anhydride (190 ml) was treated with sodium acetate (52 g) and cooled to 0° C. A solution of bromine (13.3 ml) in acetic acid (170 ml) was added during 1.5 hours and the solution was reacted at 10°–15° C. for 1.5 hours. The solution was poured into ice water and the precipitated product was filtered. Crystallization from 80% aqueous acetone gave pure title compound (78.7 g). An analytical (m.p. 150°–151° C.) sample was obtained by recrystallization from 2-propanol.

(c) 1-(4-Bromophenyl)-1,3a,4,5,6,7,7a-heptahydro-7a-(1-pyrrolidino)-indazole-3-carboxylic acid ethyl ester (Formula IV, $R_1$=4-bromophenyl, w=2)

A solution of the compound of Example 52(b) (35 g) in toluene (200 ml) was cooled to 0° C. and treated with a solution of pyrrolidinocyclohexane (15.25 g) and triethylamine (12.14 g) in toluene (60 ml). The mixture was reacted at 0° C. for 1.5 hours, then at ambient temperature for 18 hours. The mixture was poured into ice water and extracted with ethyl acetate. Drying and evaporation of the extract gave the title compound (40 g) as an oil.

IR (film): 1700, 1590, 1580, 1530, 1480, 1465 (sh), 1450 (sh), 1420, 1390, 1365, 1310, 1260, 1150, 1025, 1015 (sh), 995, 935, 835 and 775 cm$^{-1}$.

NMR (CDCl$_3$) δ: 1.0–2.25, 1.37, 2.61, 3.48, 4.33, 7.37, 7.57.

(d) 1-(4-Bromophenyl)-4,5,6,7-tetrahydro-1H-indazol-3-carboxylic acid ethyl ester (Formula V, $R_1$=4-bromophenyl, w=2)

A solution of the compound of Example 52(c) (40 g) in acetic acid (150 ml) and concentrated hydrochloric acid (150 ml) was heated at 90°–95° C. for 15 minutes. The cooled solution was diluted with water and the precipitate (32.14 g) filtered. Crystallization from ethanol gave pure title compound (29.8 g, m.p. 147° C.), lit 145°–146° C.

(e) 1-(4-Bromophenyl)-4,5,6,7-tetrahydro-1H-indazole-3-carboxylic acid (Formula VI, $R_1$=4-bromophenyl, w=2)

A solution of the mixed ethyl and methyl ester of 1-(4-bromophenyl)-4,5,6,7-tetrahydro-1H-indazole-3-carboxylic acid (3.8 g) in methanol (380 ml) was treated with 2N sodium hydroxide (54 ml), reacted for 3 hours at ambient temperature, and at reflux temperature for one hour. The solution was concentrated, diluted with water, acidified and the precipitate filtered to yield title compound (3.62 g). Recrystallization from chloroform gave pure title compound, m.p. 233°–234° C.

EXAMPLE 53

6-[1-(3-Trifluoromethylphenyl)-4,5,6,7-tetrahydro-1H-indazol-3-yl]-5Z-hexenoic acid methyl ester and -5E-hexenoic acid methyl ester (Formulae X and XI, $R_1$=3-trifluoromethylphenyl, $M_1$=CH$_3$, w=2) Refer to Chart A (a) 2-[(3-Trifluoromethyl)hydrazone]-3-oxo-butyric acid ethyl ester (Formula II, $R_1$=3-trifluoromethylphenyl)

A suspension of 3-aminobenzotrifluoride (16.13 g) in water (50 ml) was treated with concentrated hydrochloric acid (25 ml) and heated at 90° C. to dissolution. The solution was cooled and treated with ice water (85 ml). A solution of sodium nitrite (6.9 g) in water (13 ml) was added during 20 minutes and the diazonium salt solution was poured into a solution of ethyl acetoacetate (13.0 g) in a solution of ethanol (75 ml) and water (500 ml) containing sodium acetate (25° C.). The mixture was maintained at 0° C. for 3 hours and the precipitate was filtered. Crystallization of the precipitate from ethanol solution gave pure title compound (21.88 g, m.p. 90° C.).

(b) Bromo-(3-trifluoromethylphenyl)-hydrazono-acetic acid ethyl ester (Formula III, $R_1$=3-trifluoromethylphenyl)

A solution of the compound of Example 53(a) (22 g) in acetic acid (160 ml) and acetic anhydride (100 ml) was treated with sodium acetate (14.6 g), cooled to 5° C., and treated with a solution of bromine (3.8 ml) in acetic acid (50 ml) during 60 minutes. The solution was reacted at 5°–10° C. for 1.5 hours and water (500 ml) was slowly added. Precipitated title compound (23.9 g) was filtered and crystallized from 80% ethanol to yield pure compound (21.5 g), m.p. 120°–122° C.).

(c) 1-(3-Trifluoromethylphenyl)-1,3a,4,5,6,7,7a-heptahydro-7a-1-pyrrolidino-indazole-3-carboxylic acid ethyl ester (Formula IV, $R_1$=3-trifluoromethylphenyl, w=2)

A solution of the compound of Example 53(b), (34.1 g) in toluene (160 ml) at 0° C. was treated with a solution of pyrrolidinocyclohexene (16.6 g) and triethylamine (10.1 g) in toluene (50 ml) during 40 minutes. The mixture was reacted at 0° C. for 1.5 hours, then at ambient temperature for 18 hours. The mixture was poured into ice water (700 ml) and the product was extracted into ethyl acetate. The extract was washed, dried, and evaporated to yield the title compound (43.70 g) as a viscous oil.

IR (film): 2900, 2815, 1700, 1710, 1690, 1660, 1595, 1560, 1420, 1390, 1365, 1325, 1260, 1160, 1125, 1080, 1070 (sh), 1020, 995, 890, 795, 760, 730, and 700 cm$^{-1}$.
NMR (CDCl$_3$) δ: 1.0–2.2, 1.38, 2.63, 3.53, 4.34, 7.1–7.5, 7.8–8.05.

(d)
1-(3-Trifluoromethylphenyl)-4,5,6,7-tetrahydro-1H-indazole-3-carboxylic acid ethyl ester (Formula V, $R_1$=3-trifluoromethylphenyl, w=2)

A solution of the compound of Example 53(c) (42.7 g) in 25% polyphosphoric acid in acetic acid (250 ml) was heated at 90°–95° C. for 45 minutes. The solution was cooled, poured into water, and the precipitate (29.72 g) was filtered. Crystallization from Skelly B gave pure title compound (28.7 g), m.p. 77°–78° C., as two crops.

(e)
1-(3-Trifluoromethylphenyl)-4,5,6,7-tetrahydro-1H-indazole-3-methanol (Formula VII, $R_1$=3-trifluoromethylphenyl, w=2)

A solution of the compound of Example 53(d) (6.76 g) in tetrahydrofuran (150 ml) at 0° C. was treated with lithium aluminum hydride (0.76 g) and reacted for an hour. The quenched reaction mixture was filtered, the filter cake washed with THF, and the filtrate was evaporated to yield the title compound (5.86 g). Crystallization from hexane gave pure title compound (4.77 g), m.p. 93°–94° C.

(f)
1-(3-Trifluoromethylphenyl-4,5,6,7-tetrahydro-1H-indazole-3-carboxaldehyde (Formula VIII, $R_1$=3-trifluoromethylphenyl, w=2)

A solution of the compound of Example 53(e) (3.0 g) in toluene (100 ml) was treated with activated manganese (IV) oxide (12.0 g) and azeotropically distilled for 15 minutes. The suspension was cooled to 50° C., filtered, and the filtrate was evaporated to yield pure title compound (2.60 g). Hexane crystallization gave an analytical sample, m.p. 88° C.

(g)
6-[1-(3-Trifluoromethylphenyl)-4,5,6,7-tetrahydro-1H-indazol-3-yl]-5Z-hexenoic acid methyl ester and -5E-hexenoic acid methyl ester (Formulae X and XI, $R_1$=3-trifluoromethylphenyl, $M_1$=CH$_3$, w=2)

Dimsyl sodium in DMSO (80 ml) was generated with 60% sodium hydride (1.60 g) at 60°–65° C. during 2 hours, cooled to 10° C., and 4-carboxybutyltriphenylphosphonium bromide (8.86 g) was added. The aldehyde from Example 53(f) (2.94 g) was added to the ylide solution and reacted at ambient temperature for 18 hours. The solution was poured into water, neutral products were extracted with ethyl acetate, and the aqueous phase was acidified. The precipitated acids (3.51 g) were filtered and esterified with 4% methanolic hydrogen chloride (200 ml) for 2 hours to yield a mixture of the title compounds (3.7 g).

Fractionation of 2.7 g of the geometric isomer mixture on silica gel (150 g) with 9:1 Skelly B ethyl acetate gave pure E-isomer (1.81 g) and pure Z-isomer (0.79 g) as viscous oils.

The isomers were separately hydrolyzed in methanolic (50 ml) sodium hydroxide for 6.5 hours, concentrated in vacuo, and acidified to yield 0.91 g of the Z-hexenoic acid (m.p. 108° C.) and 0.69 g of the E-hexenoic acid (m.p. 105° C.).

EXAMPLE 54

5-[1-(3-Trifluoromethylphenyl)-4,5,6,7-tetrahydro-1H-indazol-3-yl]-4Z-pentenoic acid and -4E-pentenoic acid (Formulae x and XI, $R_1$=3-trifluoromethylphenyl, $M_1$=H, w=2) Refer to Chart A Dimsyl sodium was prepared at 65° C. from 60% sodium hydride (1.6 g) in DMSO (80 ml) and 3-carboxypropyltriphenylphosphonium bromide (8.58 g) was added. After 30 minutes, the aldehyde prepared in Example 53(f) (2.94 g) was added and reacted for an hour. The reaction solution was poured into ice water and neutral products were extracted into ethyl acetate. The aqueous phase was acidified and the precipitate extracted into ethyl acetate to provide 8.7 g of crude product.

The crude acids were esterified with methanolic hydrogen chloride to yield 5.05 g of crude methyl esters. Purification on silica gel (250 g) gave pure Z-ester (0.298 g) and pure E-ester (1.12 g); 60 mg of mixed products were obtained in intermediate fractions.

Hydrolysis of the Z-isomer ester in methanol (30 ml) and N sodium hydroxide for 18 hours gave 0.29 g of crude acid from acidification and ethyl acetate extraction of the hydrolysate. Crystallization from ethanol-water gave pure title compound Z-isomer (0.17 g).

Hydrolysis of the E-isomer ester in methanol (100 ml) and 3N sodium hydroxide (10 ml) for 18 hours gave the title compound E-isomer (0.92 g) as a precipitate after acidification of the hydrolysate. Crystallization from acetonitrile gave an analytical sample, m.p. 129° C., of the acid E-isomer.

EXAMPLE 55

1-(3-Trifluoromethylphenyl)-4,5,6,7-tetrahydro-1H-indazole-3-pentanoic acid (Formula XII, $R_1$=3-trifluoromethylphenyl, $M_1$=H, n=2, w=2) Refer to Chart B A solution of crude pentenoic acid prepared in Example 54 (0.7 g) in ethanol (40 ml) was treated with 10% palladium/C (0.35 g) and was reduced at 40 psi hydrogen pressure for 2 hours. Catalyst was filtered and the filtrate was evaporated to an amorphous solid (0.598 g). Crystallization from 50% aqueous acetonitrile gave pure title compound (0.32 g, m.p. 105° C).

EXAMPLE 56

6-(4,5,6,7-Tetrahydro-1-phenyl-1H-indazol-3-yl-5Z-hexenoic and -5E-hexenoic acid (Formulae X and XI, $R_1$=phenyl, $M_1$=H, n=3, w=2) Refer to Chart A

(a)
1-Phenyl-1,3a,4,5,6,7,7a-heptahydro-7a-(1-pyrrolidinyl)-3-indazole carboxylic acid ethyl ester (Formula IV, $R_1$=phenyl, w=2)

A solution of bromo(phenyl)hydrazonoacetic acid ethyl ester (27.10 g) in toluene (175 ml) at 0° C. was treated with a solution of pyrrolidino-cyclohexene (15.5 g) and triethylamine (10.1 g) in toluene (35 ml). The mixture was reacted at 0° C. for 1.5 hours, then at ambient temperature for 18 hours. The mixture was diluted with water and extracted with ethyl acetate. The extract was washed, dried and evaporated to yield the title compound (34.4 g) as a dark oil.

NMR (CDCl$_3$): 1.0–2.2, 1.33, 2.62, 3.43, 4.28, 6.8–7.7.

(b)

1-Phenyl-4,5,6,7-tetrahydro-1H-indazol-3-carboxylic acid ethyl ester (Formula V, $R_1$=phenyl, w=2)

A solution of the compound of Example 56(a) (34.4 g) in acetic acid (175 ml) and N-hydrochloric acid (150 ml) was heated at 90°-95° C. for 6.5 hours. The solution was diluted with ice water. The precipitate was filtered and crystallized from ethanol to provide pure title compound (21.9 g), m.p. 102°-103° C., lit, m.p. 103°-105.5° C.

(c)

4,5,6,7-Tetrahydro-1-phenyl-1H-indazole-3-methanol (Formula VII, $R_1$=phenyl, w=2)

A suspension of lithium tetrhydro aluminate (4.45 g, 117 mmol) in THF (400 ml) was treated with the compound of Example 56(b) (20.0 g, 78 mmol) and heated at reflux temperature for 4 hours. The suspension was cooled, excess reagent quenched, and the mixture filtered. The filtrate and ethyl acetate washes were combined, washed wit 5% sodium chloride, dried and evaporated. The residue (18.0 g) was crystallized from ethanol to yield pure title compound (11.5 g), m.p. 75°-77° C. as first crop. Subsequent crops (3.4 g) contained minor impurities.

(d)

4,5,6,7-Tetrahydro-1-phenyl-1H-indazole-3-carboxaldehyde (Formula VIII, $R_1$=phenyl, w=2)

A solution of the compound of Example 56(c) (9.0 g, 39.4 mmol) in toluene (300 ml) was treated with activated manganese dioxide (13.0 g) and azeotropically distilled for 5 hours. The mixture was filtered through a cellulose bed, the filter cake washed with hot ethyl acetate, and the combined filtrate was evaporated to yield the title compound (9.0 g). Crystallization from ethanol provided an analytical sample, m.p. 60° C.

(e)

6-(4,5,6,7-Tetrahydro-1-phenyl-1H-indazol-3-yl-5Z-hexenoic and -5E-hexenoic acid (Formulae X and XI, $R_1$=phenyl, $M_1$=H, n=3, w=2)

Dimsyl sodium was generated from 60% sodium hydride (2.17 g) in DMSO (110 ml) at 65° C. during 3 hours. The solution was cooled and 4-carboxybutyltriphenylphosphonium bromide (12.03 g) was added and reacted for 30 minutes. The ylide solution was treated with the compound of Example 56(d) (3.07 g) and reacted for 2 hours. The solution was poured into ice water and neutral products removed by ether extraction. The aqueous phase was acidified and the precipitate was extracted into ethyl acetate. The extract was washed, dried and evaporated to a viscous residue (3.25 g). Fractionated on acid-washed silica gel (750 g) gave the title compound E-isomer (1.90 g), m.p. 119°-120° C., as the first eluted product. Continued elution gave the Z-isomer (1.10 g), m.p. 145°-146° C.

EXAMPLE 57

3-(4,5,6,7-Tetrahydro-1-phenyl-1H-indazole-3-yl-2-propenoic acid (Formula IX, $R_1$=phenyl, $M_1$=H, n=0, w=2) Refer to Chart A A solution of the aldehyde prepared in Example 56(d) (1.30 g, 5.7 mmol) in pyridine (15 ml) was treated with malonic acid (2.35 g, 22 mmol) and piperidine (0.192 g) and heated at 90°-95° C. for 5 hours. The cooled solution was concentrated in vacuo to a viscous residue. The residue was diluted with water, acidified and the precipitate was filtered to yield 1.30 g. Crystallization from ethanol gave pure title compound (1.10 g), m.p. 220°-221° C.

EXAMPLE 58

5-(4,5,6,7-Tetrahydro-1-phenyl-1H-indazol-3-yl)-(Z)-4-pentenoic acid and -(E)-4-pentenoic acid (Formulae X and XI, $R_1$=phenyl, $M_1$=H, n=2, w=2) Refer to Chart A Dimsyl sodium was generated from 60% sodium hydride (1.3 g, 32 mmol) in DMSO (60 ml) at 60° C. The solution was treated with 3-carboxypropyltriphenylphosphonium bromide (6.8 g, 16 mmol) and reacted for 30 minutes at ambient temperature. The aldehyde prepared in Example 56(d) (1.8 g, 8.0 mmol) was added and reacted for 18 hours. The solution was poured into water (400 ml), extracted with ethyle acetate, and the aqueous phase acidified. The precipitate was extracted into ethyl acetate, dried, and evaporated to yield 5.6 g of crude product. Purification on CC-4 silica gel (650 g) with 9:1 Skelly B-ethyl acetate (20 ml fraction) gave Z-isomer title compound (0.5 g), m.p. 121°-122° C., in fractions 139-159; pure E-isomer title compound (0.4 g) was obtained in fractions 160-350 (m.p. 57° C.; ether hexane recrystallization).

EXAMPLE 59

1-Phenyl-4,5,6,7-tetrahydro-1H-indazole-3-hexanoic acid (Formula XII, $R_1$=phenyl, $M_1$=H, n=3, w=2) Refer to Chart B A solution of the Z-isomer prepared in Example 56(e) (0.50 g) in ethyl acetate (75 ml) was treated with platinum oxide (50 mg) and reduced at 40 psi hydrogen pressure for 3 hours. Catalyst was filtered and the filtrate evaporated to a viscous residue. Crystallization from methylene chloride-hexane solution gave pure title compound (0.43 g, m.p. 95°-97° C.).

EXAMPLE 60

[(4,5,6,7-Tetrahydro-1-phenyl-1H-indazol-3-yl)-methyl]-thioacetic acid (Formula XXII, $R_1$=phenyl, $M_1$=H, m=1, w=2) Refer to Chart E (a)

3-Chloromethyl-1-phenyl-4,5,6,7-tetrahydro-1H-indazole (Formula XXI, $R_1$=phenyl, w=2)

A solution of the alcohol prepared in Example 56(c) (6.84 g) in methylene chloride (60 ml) was treated with pyridine (2.67 ml), cooled to 0° C., and a solution of thionyl chloride (2.19 ml) in methylene chloride (20 ml) was added during 40 minutes. The solution was reacted at ambient temperature for 18 hours and poured onto crushed ice. The cold mixture was extracted with chloroform. The extract was washed with 5% sodium bicarbonate and N-hydrochloric acid solution, dried and evaporated. The residual oil (9.88 g) was purified on silica gel (800 g) (95:5 Skelly B-ethyl acetate) to yield pure title compound (4.50 g) in fractions (100 ml each) 11-30. Crystallization from hexane provided an analytical sample, m.p. 100° C.

(b)

[(4,5,6,7-Tetrahydro-1-phenyl-1H-indazol-3-yl)-methyl]-thioacetic acid (Formula XXII, $R_1$=phenyl, $M_1$=H, m—1, w=2)

A solution of methyl thioacetic acid (0.60 ml) in DMF (15 ml) was treated with triethylamine (0.94 ml). The solution was cooled to 0° C. and treated with the compound of Example 60(a) (1.10 g) in DMF (40 ml). The solution was reacted at 0°–5° C. for 30 minutes then at ambient temperature fpr 1.5 hours. The solution was diluted with waster and crude product was extracted into ethyl acetate. Drying and evaporation of solvent gave the methyl ester of the title compound as crude product (1.86 g).

Without purification, crude methyl ester was dissolved in methanol (60 ml), treated with 2N sodium hydroxide (30 ml) and reacted for 1.5 hours. The solution was concentrated to 40 ml, cooled, and acidified. The precipitate (1.33 g) was crystallized from acetonitrile to yield pure title compound, m.p. 163°–164° C.

EXAMPLE 61

3-[(4,5,6,7-Tetrahydro-1-phenyl-1H-indazole-3-yl)-methyl]thiopropionic acid (Formula XXIII, $R_1$=phenyl, $M_1$=H, m=2, w=2) Refer to Chart E A solution of methyl-3-mercaptopropionate (1.80 g) in DMF (15 ml) was treated with triethylamine (1.51 g), cooled to 0° C. and treated with the compound of Example 60(a) (2.64 g). The solution was reacted at ambient temperature for 18 hours, diluted with water, and the precipitated methyl ester of the title compound was extracted into ethyl acetate to provide 4.70 g.

The crude methyl ester was dissolved in methanol (100 ml), treated with 2N sodium hydroxide, and reacted for 5 hours. The solution was concentrated to 25 ml, cooled, and acidified. The precipitate (3.95 g) was crystallized from acetonitrile to yield pure title compound (1.79 g, m.p. 105°–106° C.).

EXAMPLE 62

6-[4,5,6,7-Tetrahydro-1-(4-nitrophenyl)-1H-indazol-3-yl]-5-Z-hexenoic acid methyl ester and -5E-hexenoic acid methyl ester (Formula X and XI, $R_1$=4-nitrophenyl, $M_1$=$CH_3$ n=3, w=2) Refer to Chart A.

(a)

1-(4-Nitrophenyl)-1,3a,4,5,6,7,7a-heptahydro-7a-(1-pyrrolidinyl)-3-indazole carboxylic acid ethyl ester (Formula IV, $R_1$=4-nitrophenyl, w=2)

A solution of bromo-(4-nitrophenyl)hydrazonoacetic acid ethyl ester (31.6 g) in toluene (150 ml) at −5° C. was treated with pyrrolidine cyclohexene (16.1 ml, 15.12 g, 0.10 mole). The orange suspension was treated with triethylamine (21 ml, 15.18 g, 0.150 mole), reacted at 0° C. for 2 hours, then at ambient temperature for 16 hours. The suspension was diluted with ethyl acetate, washed with 5% saline, dried and evaporated. The residue was crystallized from ethanol to yield the title compound (34.16 g), m.p. 135° C. The filtrate residue gave additional crude title compound (3.6 g).

(b)

1-(4-Nitrophenyl)-4,5,6,7-tetrahydro-1H-indazole-3-carboxylic acid ethyl ester (Formula V, $R_1$=4-nitrophenyl, w=2)

A solution of the compound of Example 62(a) (33.63 g) in acetic acid (150 ml) and 1N hydrochloric acid (100 ml) was heated at 95° C. for 30 minutes. The suspension was cooled, diluted to 1 L with water, and the precipitate filtered to yield the title compound 825.30 g). An analytical sample was obtained from ethanol, m.p. 173° C.

(c)

1-(4-Nitrophenyl)-4,5,6,7-tetrahydro-1H-indazole-3-carboxylic acid (Formula VI, $R_1$=4-nitrophenyl, w=2)

A solution of the compound of Example 56(b) (24.3 g) in ethanol (300 ml) was treated with 1N sodium hydroxide (160 ml) and heated at reflux temperature for one hour. The solution was cooled, diluted with ice water, and acidified. The precipitate was filtered and recrystallized from ethanol to yield pure title compound (20.9 g).

IR (mull): 3200–2100, 1680, 1595, 1520, 1495, 1340, 1305, 1260 and 1205 $cm^{-1}$.

NMR (DMSO) δ: 1.75,. 2.75, 7.83, 8.32.

(d)

1-(4-Nitrophenyl)-4,5,6,7-tetrahydro-1H-indazole-3-methanol (Formula VII, $R_1$=4-nitrophenyl, w=2)

A solution of the compound of Example 62(c) (10.0 g) in THF (600 ml) was treated with sodium borohydride (4.96 g), cooled to 2° C. and treated with boron trifluoride etherate (13.1 ml) during 45 minutes. The solution was reacted at ambient temperature for 18 hours and diluted with ice water. The precipitate was extracted into ether. The extract was dried and evaporated to yield crude product (12.0 g). Crystallization from ethanol gave pure title compound (7.73 g, m.p. 219° C.).

(e)

1-(4-Nitrophenyl)-4,5,6,7-tetrahydro-1H-indazole-3-carboxaldehyde (Formula VIII, $R_1$=4-nitrophenyl, w=2)

A solution of the compound of Example 62(d) (7.5 g) in hot toluene (750 ml) was treated with activated manganese (IV) oxide (22.5 g) and azeotropically distilled for one hour. The hot solution was filtered, the filtrate and ethyl acetate washes were evaporated to yield pure title compound (6.0 g, m.p. 147°–148° C.) after ethanol crystallization.

(f)

6-[4,5,6,7-Tetrahydro-1-(4-nitrophenyl)-1H-indazol-3-yl]-5Z-hexenoic acid methyl ester and -5E-hexenoic acid methyl ester (Formulae X and XI, $R_1$=4-nitrophenyl, $M_1$=$CH_3$, n=3, w=2)

Dimsyl sodium was generated from 60% sodium hydride (3.52 g) in DMSO (200 ml) at 65° C. during 4 hours. The cooled solution was treated with 4-carboxybutyltriphenylphosphonium bromide and reacted for one hour. The ylide solution was treated with the compound of Example 62(e) (6.0 g) and heated for an hour. The reaction solution was diluted with water and extracted with ether. The aqueous phase was acidified and the semi-solid precipitate was extracted into ethyl acetate. Drying and evaporation of solvent gave a residue (15.6 g) of crude hexenoic acid aand Wittig reaction by-products. Crystallization of the residue from methanol gave the Z-isomer (2.2 g) which was further purified by crystallization from ethanol to yield pure title compound Z-isomer (1.68 g, m.p. 178°–180° C.). Concentration of the methanolic filtrate gave 3.19 g of the Z/E-isomers as second crop product. The filtrate residue (2.3 g) from a third crop was esterified with excess ethereal diazomethane and the crude residue (4.2 g) was purified on silica gel (450 g) with 9:1 Skelly B-ethyl acetate. Visual separation of isomers was achieved to provide pure title compound Z-ester (100 mg), m.p. 113°–114° C., in fractions 1–5 (500 ml fractions) and pure E-ester (280 mg), m.p. 90°–91° C., in fractions 7–10.

The third crop products and recrystallization filtrate residues were separately esterified and purified on silica gel to yield pure Z-isomer (1.03 g) and pure E-isomer (1.8 g).

EXAMPLE 63

1-(4-Nitrophenyl)-4,5,6,7-tetrahydro-1H-indazole-3-hexanoic acid methyl ester (Formula XII, $R_1$=4-nitrophenyl, $M_1$=$CH_3$, n=3, w=2) Refer to Chart B A solution of 6-[4,5,6,7-tetrahydro-1-(4-nitrophenyl)-1H-inda-zol-3-yl]hexanoic acid (1.11 g, 3 mmol) in THF (10 ml) was treated with sodium borohydride (0.175 g) and boron trifluoride etherate (4.7 mmol) in THF (11 ml) during 0.5 hour. The solution was reacted for 18 hours at ambient temperature, treated with propionic acid (2 ml), and heated at 70° C. for 2 hours. The solution was cooled, dilution with water and the precipitate was extracted into ethyl acetate. Drying and evaporation of solvent gave crude title compound (1.69 g) as a viscous residue. Polar impurities were removed by filtration through silica gel (100 g) to yield pure title compound (0.45 g), m.p. 60°–61° C., after methanol crystallization.

EXAMPLE 64

1-(4-Nitrophenyl)-4,5,6,7-tetrahydro-1H-indazole-3-hexanoic acid (Formula XII, $R_1$=4-nitrophenyl, $M_1$=H, n=3, w=2)

A solution of the compound of Example 63 (0.20 g) in methanol (20 ml) was treated with N sodium hydroxide (7.5 ml) and heated at reflux temperature for 30 minutes. The cooled solution was acidified and the precipitate was crystallized from acetonitrile to yield pure title compound (0.15 g), m.p. 119°–121° C.

EXAMPLE 65

1-[4-(Acetylamino)phenyl]-4,5,6,7-tetrahydro-1H-indazole-3-hexanoic acid (Formula XII, $R_1$=4-(acetylamino)phenyl, $M_1$=H, n=3, w=2) Refer to Chart B A solution of 6-[4,5,6,7-tetrahydro-1-(4-nitrophenyl)-1H-inda-zol-3-yl]hexenoic acid n acetic acid (75 ml) was treated with 10% palladium/C (0.80 g) and reduced at 40 psi hydrogen pressure for 2 hours. The catalyst was filtered and the filtrate was evaporated to yield crude 1-[4-(amino)phenyl]-4,5,6,7-tetrahydro-1H-indazole-3-hexanoic acid. Acylation with acetic anhydride (5 ml) and pyridine (10 ml) gave crude title compound (0.45 g). An analytical sample (m.p. 175° C.) was obtained from methanol-ether solution.

EXAMPLE 66

6-(4-Nitrophenyl)-4,5,6,7-tetrahydro-1H-indazole-3-hexanol (Formula XIV, $R_1$=4-nitrophenyl, n=3, w=2)

A solutioin of 6-[4,5,6,7-tetrahydro-1-(4-nitrophenyl)-1H-indazol-3-yl]-5Z-hexenoic acid (0.96 g, 2.6 mmol) in THF (10 ml) was treated with sodium borohydride (0.11 g) and a solution of boron trifluoride etherate (0.38 ml) in THF (15 ml) was added during 30 minutes. The solution was reacted at ambient temperature for 18 hours, treated with propionic acid (2 ml) and heated at reflux temperature for 2 hours. The solution was diluted with water.

The precipitate was extracted into ethyl acetate and the extract was washed with 5% sodium bicarbonate solution. Drying and evaporation of solvent gave a residue (1.38 g) containing three major products. Fractionation on silica gel (100 g) with 85:15 Skelly B-ethyl acetate gave the propionate of the title compound (110 mg) in fractions 10–30 (20 ml fraction), and the hexanoate ester of the title compound of Formula XII (370 mg) in fractions 31–40. Elution with ethyl acetate provided crude alcohol.

The propionate (110 mg) was hydrolyzed in methanolic sodium hydroxide at reflux temperature. The isolated crude carbinols were combined and refractionated on silica gel (65 g) with 3:1 ethyl acetate-Skelly B. Fractions 50–80 (20 ml fractions) provided pure title compound. An analytical sample (m.p. 69°–70° C.) was obtained by crystallization from ether-hexane solution.

EXAMPLE 67

6-[1-(4-Fluorophenyl)-4,5,6,7-tetrahydro-1H-indazol-3-yl]-(Z)-5-hexenoic acid and -(E)-5-hexenoic acid (Formulae X and XI, $R_1$=4-fluorophenyl, $M_1$=H, n=3, w=2) Refer to Chart A (a)

1-(4-Fluorophenyl)-4,5,6,7-tetrahydro-1H-indazole-3-carboxylic acid ethyl ester (Formula V, $R_1$=4-fluorophenyl, w=2)

A solution of bromo-(4-fluorophenyl)hydrazonoacetic acid ethyl ester (15.6 g, 54 mmol) in toluene (90 ml) was cooled to 0° C. and treated with a solution of triethylamine (5.46 g, 54 mmol) and pyrrolidinecyclohexene (8.16 g, 54 mmol). The reaction temperature was raised to 25° C. and reacted for 18 hours. The suspension was diluted with ice water and extracted with ethyl acetate. The extracts were washed with 5% saline, dried and evaporated to yield crude 1-(4-fluorophenyl)-1,3a,4,5,6,7,7a-heptahydro-7a-1-pyrrolidino-indazole-3-carboxylic acid ethyl ester (20.4 g) as a pale yellow oil.

The crude ester in acetic acid (60 ml) and 1N hydrochloric acid (60 ml) was heated at 90°–95° C. for 30 minutes, cooled, and the crystalline material was filtered. Recrystallization from ethanol gave pure title compound (11.67 g), m.p. 100°–101° C.

(b)

1-(4-Fluorophenyl)-4,5,6,7-tetrahydro-1H-indazole-3-methanol (Formula VII, $R_1$=4-fluorophenyl, w=2)

Lithium tetrahydride aluminate (1.55 g, 80 mmol) in THF (600 ml) was treated in portions with the compound of Example 67(a) (11.67 g, 40 mmol) and reacted for one hour. The suspension was quenched by dropwise addition of water (10 ml) in THF, 15% sodium hydroxide (20 ml) and finally water. The suspension was filtered, the filter cake washed with THF and the filtrate evaporated to dryness. Recrystallization of the residue from ethyl acetate-hexane solution gave pure title compound, 8.75 g, m.p. 117°–118° C.

(c)

1-(4-Fluorophenyl)-4,5,6,7-tetrahydro-1H-indazole-3-carboxaldehyde (Formula VIII, $R_1$=4-fluorophenyl, w=2)

A solution of the compound of Example 67(b) (8.75 g, 35.5 mmol) in toluene (300 ml) was treated with activated manganese dioxide (4.6 g). Additional reagent (2.2 g) was added three times during 40 hours of reflux. Subsequent studies suggest that azeotropic distillation significantly shortens reaction times.

The suspension was filtered, the filtrate evaporated and the residue crystallized from hexane to yield pure title compound (6.60 g), m.p. 101°–102° C.

(d)

6-[1-(4-Fluorophenyl)-4,5,6,7-tetrahydro-1H-indazol-3-yl]-(Z)-5-hexenoic acid and -(E)-5-hexenoic acid (Formulae X and XI, $R_1$=4-fluorophenyl, $M_1$=H, n=3, w=2)

Dimsyl sodium was prepared from 50% sodium hydride (0.975 g, 24.36 mmol) in DMSO (50 ml) at 60°–65° C. for 3.5 hours. The solution was treated with 4-carboxybutyltriphenylphosphonium bromide (5.40 g, 12.1 mmol) at 5° C. and reacted for 1.25 hours. The ylide solution was treated with the compound of Example 67(c) (1.46 g, 6.09 mmol) and reacted at 25° C. for one hour. The solution was poured into ice water, neutral products extracted into ethyl acetate, and the aqueous phase was acidified. The precipitated acids were extracted into ethyl acetate, washed, and dried to yield crude title compounds. Isomer separation on silica gel (CC-4, 200 g) with 10% ethyl acetae in Skelly B (20 ml fractions) gave the Z-isomer (0.82 g, m.p. 118°–119° C.) in fractions 80–220 and the E-isomer (0.520 g, m.p. 149°–150° C.) was obtained in fractions 240–310.

EXAMPLE 68

1-(4-Fluorophenyl)-4,5,6,7-tetrahydro-3-propenoic acid (Formula IX, $R_1$=4-fluorophenyl, $M_1$=H, n=0, w=2) Refer to Chart A A solution of the compound of Example 67(c) (2.05 g, 8.4 mmol) in pyridine (40 ml) was treated with malonic acid (3.5 g, 33.6 mmol), piperidine (0.285 g) and heated at 100° C. for 18 hours. The solution was concentrated to a viscous residue, the residue was dissolved in water, acidified, and the precipitate extracted into ethyl acetate. Drying and evaporation of solvent gave crude title compound which crystallized from ethanol to yield pure title compound, 1.26 g, m.p. 210°–211° C.

EXAMPLE 69

1-(4-Fluorophenyl)-4,5,6,7-tetrahydro-1H-indazole-3-hexanoic acid (Formula XII, $R_1$=4-fluorophenyl, $M_1$=H, n=3, w=2) Refer to Chart B A solution of the Z-isomer of Example 67(d) (0.50 g) in ethanol (100 ml) was treated with 10% palladium on carbon (0.20 g) and hydrogenated at 40 psi for one hour. The mixture was filtered and the filtrate evaporated to yield the title compound (0.43 g). Recrystallization from acetonitrile solution gave an analytical sample, m.p. 95°–96° C.

EXAMPLE 70

1-(4-Fluorophenyl)-4,5,6,7-tetrahydro-1H-indazole-3-propionic acid (Formula XII, $R_1$=4-fluorophenyl, $M_1$=H, n=0, w=2) Refer to Chart B A solution of the compound of Example 68 (0.80 g) in ethanol (80 ml) was treated with $PtO_2$ (0.25 g) and hydrogenated at 40 psi for 3 hours. Catalyst was filtered, the filtrate evaporated, and the residue was crystallized from ethanol to yield the title compound, 0.642 g, m.p. 128°–129° C.

EXAMPLE 71

1-(4-Chlorophenyl)-4,5,6,7-tetrahydro-1H-indazole-3-carboxaldehyde (Formula VIII, $R_1$=4-chlorophenyl, w=2)

(a)

1-(4-Chlorophenyl)-4,5,6,7-tetrahydro-1H-indazole-3-carboxylic acid ethyl ester (Formula V, $R_1$=4-chlorophenyl, w=2)

A solution of bromo-(4-chlorophenyl)hydrazonoacetic acid ethyl ester (18.24 g, 60 mmol) in toluene (390 ml) and 10.02 g (60 mmol) of morpholinocyclohexene (10.02 g, 60 mmol) was cooled to 0° C. and triethylamine (12.6 ml, 90 mmol) was added. The solution was reacted for 1.5 hours at 0° C. and at ambient temperature for 48 hours. Triethylamine hydrochloride was filtered, the filtrate was washed with 10% hydrochloric acid, dried and evaporated. The crude product was crystallized from methanol to yield pure title compound (10.04 g), m.p. 139°–140° C. (lit 139°–141° C.).

(b)

1-(4-Chlorophenyl)-4,5,6,7-tetrahydro-1H-indazole-3-methanol (Formula VII, $R_1$=4-chlorophenyl, w=2)

A suspension of lithium tetrahydroaluminate (2.73 g, 72 mmol) in THF (550 ml) was treated with the compound of Examle 71(a) (11.0 g, 36 mmol) and reacted at ambient temperature for 25 minutes. The excess reagent was quenched and the mixture filtered. The filtrate and ethyl acetate washes were evaporated and the residue was evaporated from ethanol-hexane solution to yield pure title compound (5.62 g), m.p. 125°–126° C.

(c)

1-(4-Chlorophenyl)-4,5,6,7-tetrahydro-1H-indazole-3-carboxaldehyde (Formula VIII, $R_1$=4-chlorophenyl, w=2)

A solution of the compound of Example 71(b) (0.5 g) in methylene chloride (20 ml) was treated with activated manganese dioxide (5.0 g) and reacted at ambient temperature for 4 hours. The suspension was filtered and the filtrate was evaporated to yield the title compound (0.26 g). Crystallization from hexane provided an analytical sample, m.p. 117°–118° C.

EXAMPLE 72

1-(4-Chlorophenyl)-4,5,6,7-tetrahydro-1H-indazole-3-carboxylic acid (Formula VI, $R_1$=4-chlorophenyl, w=2)

A solution of the mixed ethyl and methyl esters of 1-(4-chlorophenyl)-4,5,6,7-tetrahydro-1H-indazole-3-carboxylic acid (5.5 g) in methanol (800 ml) was treated with 2N sodium hydroxide (95 ml) and reacted at ambient temperature. Only the thin layer chromatography more polar methyl ester remained. The solution was heated at reflux temperature for 60 minutes, cooled, concentrated, and acidified. The precipitate was filtered, washed with water and dried to yield the title compound, m.p. 223°–224° C. (lit m.p. 218° C.). Recrystallization from chloroform hexane solution provided the analytical sample.

EXAMPLE 73

[1-(4-Chlorophenyl)-4,5,6,7-tetrahydro-1H-indazol-3-yl]-methoxy acetic acid ethyl ester (Formula XX, $R_1$=4-chlorophenyl, $M_1$=$CH_2CH_3$, m=1, w=2) Refer to Chart E A suspension of 50% sodium hydride (0.264 g) in THF (25 ml) was treated with the compound of Example 71(b) (1.3 g) in THF (30 ml). The solution was reacted at 0° C. for one hour, treated with ethyl bromoacetate (1.2 ml) and reacted for 18 hours. The mixture was quenched with ethanol, diluted with water and the precipitate was extracted into ethyl acetate. Drying and evaporation of solvent gave crude title compound (2.22 g). Fractionation on silica gel (125 g) with 10% ethyl acetate in hexane gave pure title compound (1.08 g) in fractions 180–260. Crystallization from hexane gave the analytical sample, m.p. 86°–87° C.

EXAMPLE 74

[1-(4-Chlorophenyl)-4,5,6,7-tetrahydro-1H-indazol-3-yl]-methoxy acetic acid (Formula XX, $R_1$=4-chlorophenyl, $M_1$=H, m=1, w=2)

A solution of the compound of Example 73 (0.75 g) in methanol (15 ml) was treated with N sodium hydroxide (6 ml) and reacted at room temperature for 15 minutes. The solution was concentrated in vacuo, diluted with water, and acidified. The precipitate was filtered to yield the title compound (0.58 g). An analytical sample (m.p. 185°–186° C.) was obtained from methanol-hexane solution.

EXAMPLE 75

1-(4-Methoxyphenyl)-4,5,6,7-tetrahydro-1H-indazole-3-carboxylic acid (Formula VI, $R_1$=4-methoxyphenyl, w=2) Refer to Chart A A solution of 1-(4-methoxyphenyl)-4,5,6,7-tetrahydro-1H-indazole-3-carboxylic acid ethyl ester in methanol (50 ml) was heated at reflux temperature for one hour, cooled, concentrated in vacuo, diluted with water, and acidified. The precipitate was filtered to yield the title compound (0.360 g). An analytical sample (m.p. 233°–234° C.) was obtained from methylene chloride-hexane solution.

EXAMPLE 76

1-(2,4-Dichlorophenyl)-4,5,6,7-tetrahydro-1H-indazole-3-carboxylic acid (Formula VI, $R_1$=2,4-dichlorophenyl, w=2)

A solution of the methyl and ethyl esters of 1-(2,4-dichlorophenyl)-4,5,6,7-tetrahydro-1H-indazole-3-carboxylic acid (5 g, 1.8 g) in methanol (220 ml) was treated with 2N sodium hydroxide (28 ml), reacted at ambient temperature for 3 hours, and at reflux temperature for one hour. The cooled solution was concentrated, diluted with water, and acidified. The precipitate was filtered, washed with water and dried to yield the title compound (1.27 g), m.p. 239°–240° C. Crystallization from chloroform-hexane solution gave an analytical sample, m.p. 238° C.

EXAMPLE 77

1-(4-Bromophenyl)-4,5,6,7-tetrahydro-1H-indazole-3-methanol (Formula VII, $R_1$=4-bromophenyl, w=2) Refer to Chart A Lithium aluminum hydride (1.52 g) in THF (100 ml) was treated with 1-(4-bromophenyl)-4,5,6,7-tetrahydro-1H-indazole-3-carboxylic acid ethyl ester (6.98 g) and reacted at ambient temperature for 2 hours. Additional reagent (1.52 g) was added and the reaction was continued for one hour to complete the conversion. Excess reagent was quenched, the mixture was filtered, and the filtrate was evaporated to yield crude title compound (548 g). Crystallization from acetonitrile gave pure title compound (4.32 g, m.p. 126°–127° C.). The filtrate residue contained equal proportions of title compound and the des-bromo derivative.

EXAMPLE 78

1-(4-Bromophenyl)-4,5,6,7-tetrahydro-1H-indazole-3-carboxaldehyde (Formula VIII, $R_1$=4-bromophenyl, w=2) Refer to Chart A A toluene (150 ml) solution of the compound of Example 77 (3.0 g) was treated with activated manganese (IV) oxide (9.0 g) and azeotropically distilled during 30 minutes. The hot suspension was filtered and the filtrate evaporated to yield pure title compound (1.99 g). A repeat reaction provided 2.0 g. Crystallization of the combined product from acetonitrile gave 3.80 g, m.p. 120°–121° C.

EXAMPLE 79

[1-(4-Bromophenyl)-4,5,6,7-tetrahydro-1H-indazol-3-yl]-methoxy acetic acid (Formula XX, $R_1$=4-bromophenyl, $M_1$=H, m=1, w=2) Refer to Chart E A suspension of sodium hyride (0.63 g) in THF (65 ml) was treated with the compound of Example 77 (4.0 g) and heated at 60° C. for 3 hours. Ethyl bromoacetate (10.9 g) was added to the cooled mixture and the reaction was allowed to proceed at ambient temperature overnight. The crude methoxy acetic acid ethyl ester was poured into ethanol (200 ml), treated with 3N sodium hydroxide and heated at reflux temperature for 1.5 hours. The solution was concentrated to 100 ml, diluted to 250 ml with water and unreacted compound of Example 77 extracted into ethyl acetate. The aqueous phase was acidified and crude product filtered. Ethanol crystallization gave the title compound (2.18 g, m.p. 123° C.). An analytical sample, m.p. 183° C., was obtained from ethanol solution.

EXAMPLE 80

6-(4-Bromophenyl)-4,5,6,7-tetrahydro-1H-indazole)-hexanol (Formula XIV, $R_1$=4-bromophenyl, n=3, w=2)

A solution of crude 6-(4-bromophenyl)-4,5,6,7-tetrahydro-1H-indazole-1-hexenol (1.6 g) in ethanol (50 ml) was treated with platinum oxide (80 mg) and reduced at atmospheric pressure 1.5 hours. Catalyst was filtered and the filtrate was evaporated. The product (1.6 g), a mixture of phenyl and bromophenyl derivatives, was purified on silica gel (160 g) with 4:1 Skelly B-ethyl acetate to yield pure title compound (0.75 g), an oil.

IR (film): 3225, 2910, 2840, 1590, 1500, 1405, 1385, 1070, 1050, 1010, 850 and 755 cm$^{-1}$.

NMR (CDCl$_3$) δ: 1.2–2.1, 2.4–2.8, 3.63, 7.40, 7.60. MS m/e: 378, 376 (M+), 347, 305, 303, 293, 292, 291, 290 (base peak) and 83.

EXAMPLE 81

1-(3-Trifluoromethyl-4,5,6,7-tetrahydro-1H-indazole-3-carboxylic acid (Formula VI, $R_1$=3-trifluoromethylphenyl, w=2) Refer to Chart A A solution of the compound prepared in Example 53(d) (2.0 g) in methanol (60 ml) was treated with 3N sodium hyroxide (10 ml) and reacted at ambient temperature for 18 hours. The solution was concentrated, acidified and the precipitate (1.63 g) was crystallized from 80% ethanol to yield pure title compound (1.46 g), m.p. 183°–184° C.

EXAMPLE 82

3-[(1,4,5,6-Tetrahydro-1-(3-trifluoromethyl)phenyl)-3-cyclopentapyrazolyl]E-oxiranebutanoic acid methyl ester (Formula XXVI, n=3, $M_1$=CH$_3$, $R_1$=3-trifluoromethylphenyl, w=1)

A solution of 6[3-(trifluoromethyl)-phenyl]-1,4,5,6-tetrahydro-3-cyclopentapyrazolyl]-(E)-5-hexenoic acid methyl ester (0.21 g) in methylene chloride (10 ml) is treated with m-chloroperoxybenzoic acid (0.26 g) and reacted at room temperature for 18 hours. The solution is diluted with ether, washed with 1% thiosulfate and 5% sodium bicarbonate solution, dried and evaporated. The residue (0.169 g) is purified on silica gel (65 g) with 95:15 Skellysolve-B:ethyl acetate. Fractions 19–25 give pure title compound (11.9 mg) as an oil.

EXAMPLE 83

[(1-3,4-dichlorophenyl)-1,4,5,6-tetrahydro-3-cyclopentapyrazolyl]-E-oxiranepentanoic acid methyl ester (Formula XXVI, n=2, $M_1$=CH$_3$, $R_1$=3,4-dichlorophenyl, w=1)

A solution of 5[(3,4-dichlorophenyl]-1,4,5,6-tetrahydro-3-cyclopentapyrazolyl]-(E)-4-pentenoic acid methyl ester (1.3 g) in methylene chloride (50 ml) is treated with m-chloroperoxybenzoic acid (1.26 g) and reacted for 2 hours. The solution is diluted, washed with thiosulfate and bicarbonate solution, dried, and evaporated to yield crude epoxide (1.82 g). Purification on silica gel gives pure title compound (0.42 g), m.p. 119°–120° C., after ethanol recrystallization.

EXAMPLE 84

3-[(1,4,5,6-Tetrahydro-1-(3-trifluoromethyl)phenyl)-3-cyclopentapyrazolyl]-(Z)-oxirane butanoic acid methyl ester (Formula XXVI, n=3, $M_1$=CH$_3$, $R_1$=3-trifluoromethylphenyl, w=1)

A solution of 6-[3-(trifluoromethyl)phenyl]-1,4,5,6,-tetrahydro-3-cyclopentapyrazolyl]-(Z)-5-hexenoic acid methyl ester (0.21 g) in methylene chloride (10 ml) is treated with m-chloroperoxybenzoic acid and reacted at room temperature for 18 hours. The solution is diluted with ether, washed with 1% sodium thiosulfate and 5% sodium bicarbonate solution. The residue (0.28 g) from solvent evaporation is purified on silica gel (65 g) with 9:1 Skellysolve-B:ethyl acetate to yield pure title compound (0.103 g) as an oil.

EXAMPLE 85

1-Phenyl-1,4,5,6-tetrahydro-3-cyclopentapyrazole carboxaldehyde, neopentyl glycol acetal (Formula XXVII, $R_{12}R_{13}$ taken together=—CH$_2$C(CH$_3$)$_2$CH$_2$—, $R_1$=phenyl, w=1)

A suspension of 1-phenyl-1,4,5,6-tetrahydro-3-cyclopentapyrazole carboxaldehyde (110 g) in toluene (1 L) is treated with 2,2-dimethylpropane diol (59.3 g ), toluenesulfonic acid (600 mg), and azeotropically distilled for 2 hours. Additional diol (19.1 g) is added and distillation continued for 3 hours. The cooled solution is washed with 5% sodium bicarbonate, 5% saline, dried, and evaporated. The crystalline residue is triturated with ether to yield pure title compound (129.3 g, m.p. 108°-110°). The filtrate residue is crystallized from acetonitrile to provide additional title compound (18.3 g).

IR (mull) 1605, 1500, 1370, 1365, 1095, 1085, 1050, 1035, 1010, 985, 965, 915, 755 and 690 cm$^{-1}$.

NMR (CDCl$_3$) δ 0.77, 1.27, 2.2–3.2, 3.63, 5.52, 7.0–7.9. M.S. m/e 298 (M+), 299, 214, 213, 212, 211, 183, 77, 69, 41.

EXAMPLE 86

1-(4-Nitrophenyl)-1,4,5,6-tetrahydro-3-cyclopentapyrazole carboxaldehyde neopentyl glycol acetal (Formula XXVII, $R_{12}R_{13}$ taken together=—CH$_2$C(CH$_3$)$_2$CH$_2$—, $R_1$=4-nitrophenyl, w=1)

A solution of 1-(4-nitrophenyl)-1,4,5,6-tetrahydro-3-cyclopentapyrazole carboxaldehyde (5.14 g, 20 mmoles) in toluene (120 ml) is treated with p-toluenesulfonic acid (100 mg) and 2,2-dimethyl-1,3-propanediol. The solution is refluxed for 2 hours and cooled. The crystalline product is filtered to yield pure title compound (6.20 g, m.p. 211°–212° C.). An analytical sample is crystallized from toluene.

IR (mull) 1600, 1515, 1470, 1395, 1340, 1110, 1085, 1050, 1020, 990, 980, 935, 900, 860, 760 cm$^{-1}$.

NMR (CDCl$_3$) δ 0.80, 1.30, 2.46–3.17, 3.69, 5.53, 7.78, 8.27. M.S. m/e 343 (M+), 259, 258 (base peak), 257, 256, 228, 218 and 182.

FORMULA CHART

 I

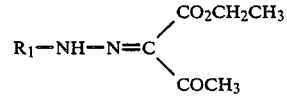 II

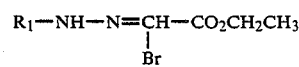 III

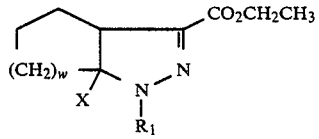 IV

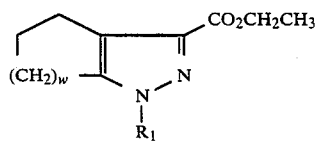 V

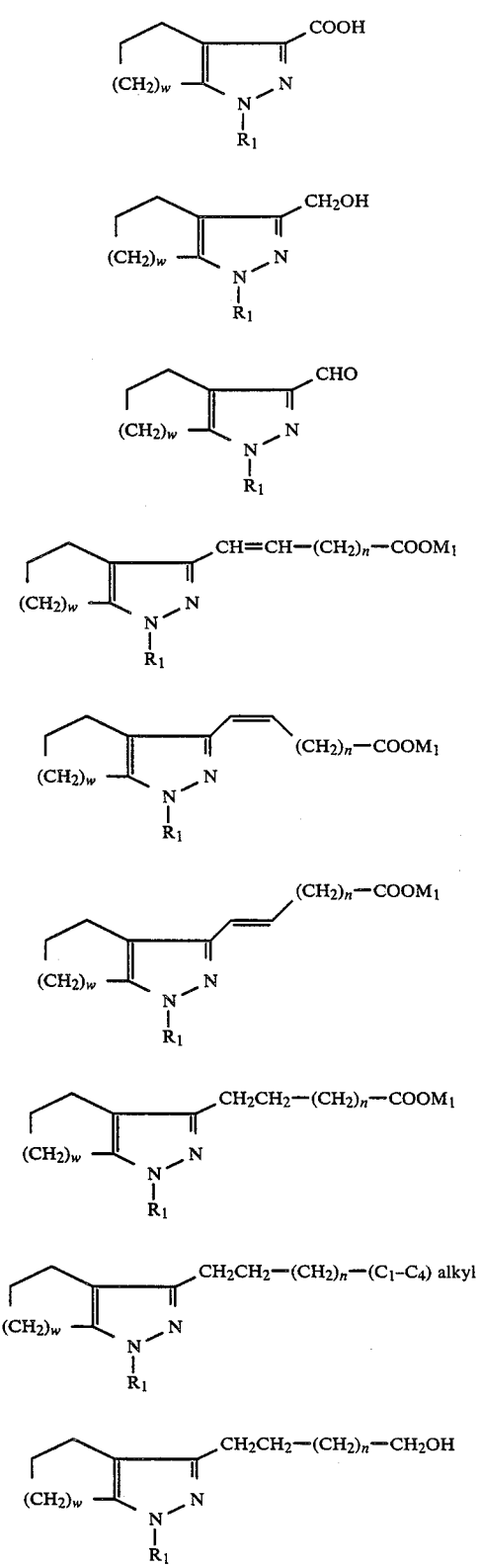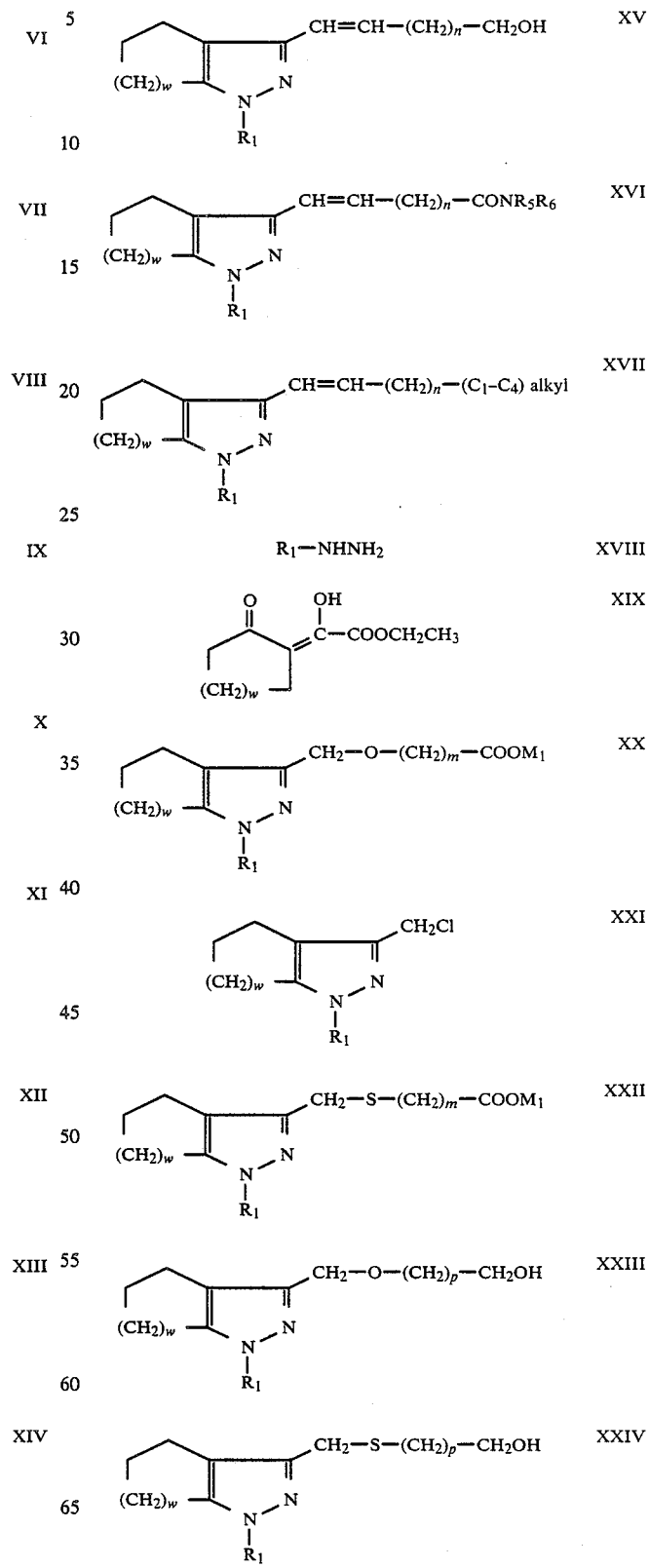

-continued
FORMULA CHART
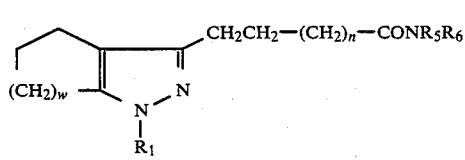
XXV
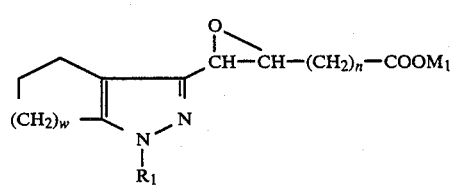
XXVI
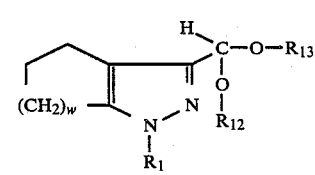
XXVII
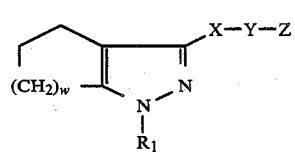
XXX
CHART A
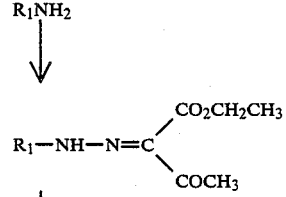
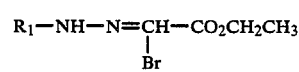 II
 III
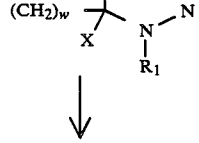 IV
-continued
CHART A
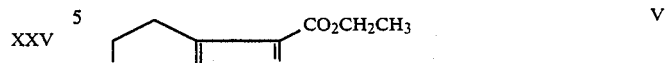 V
 VI
 VII
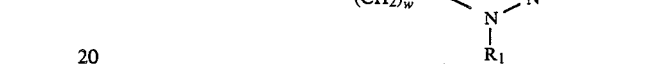 VIII
 IX
 X
 XI CHART B
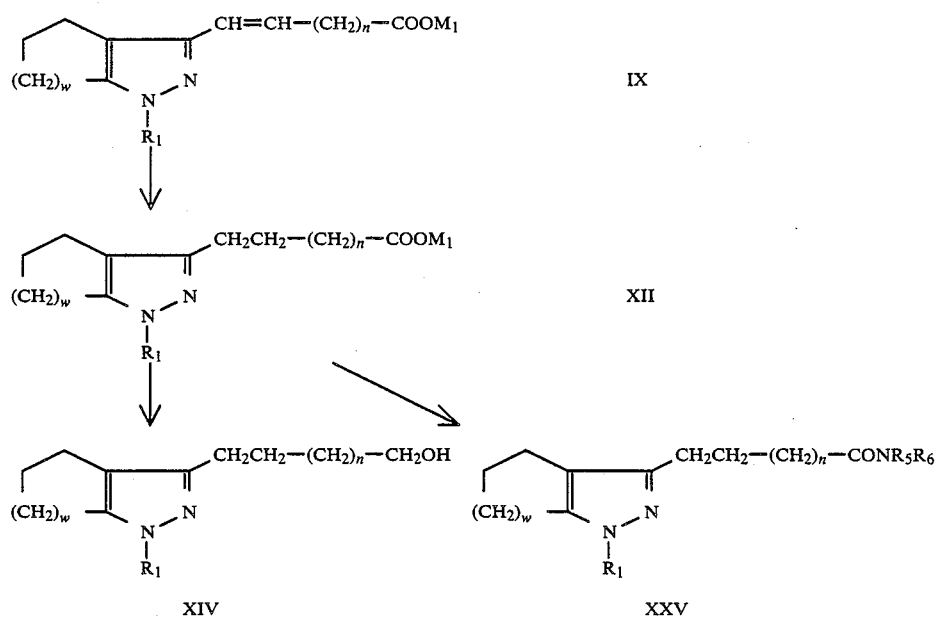
CHART C
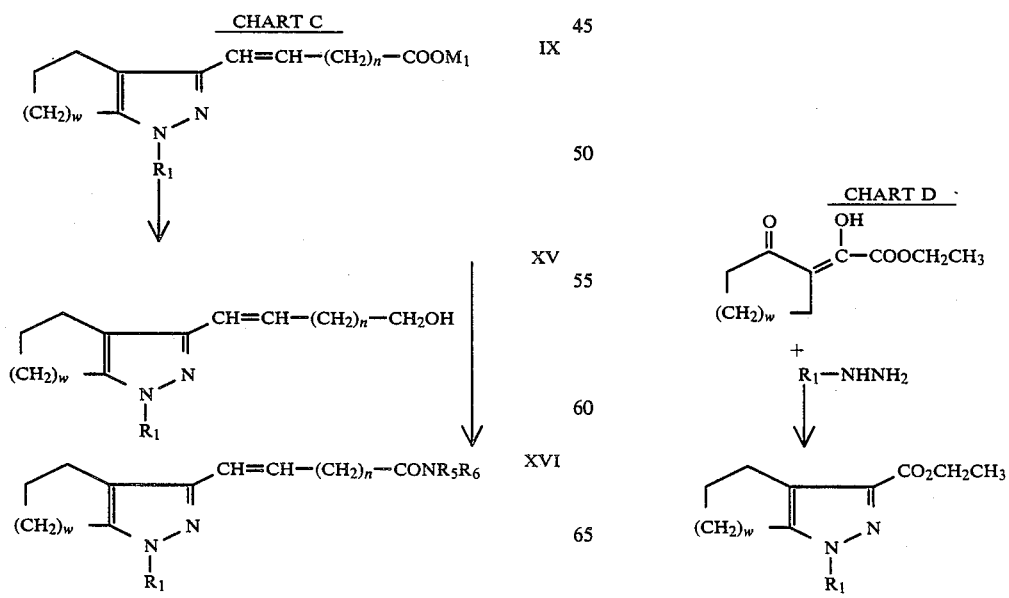
CHART D
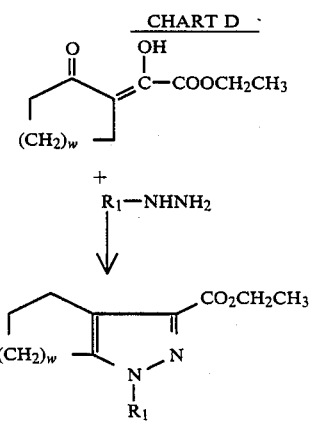

CHART E

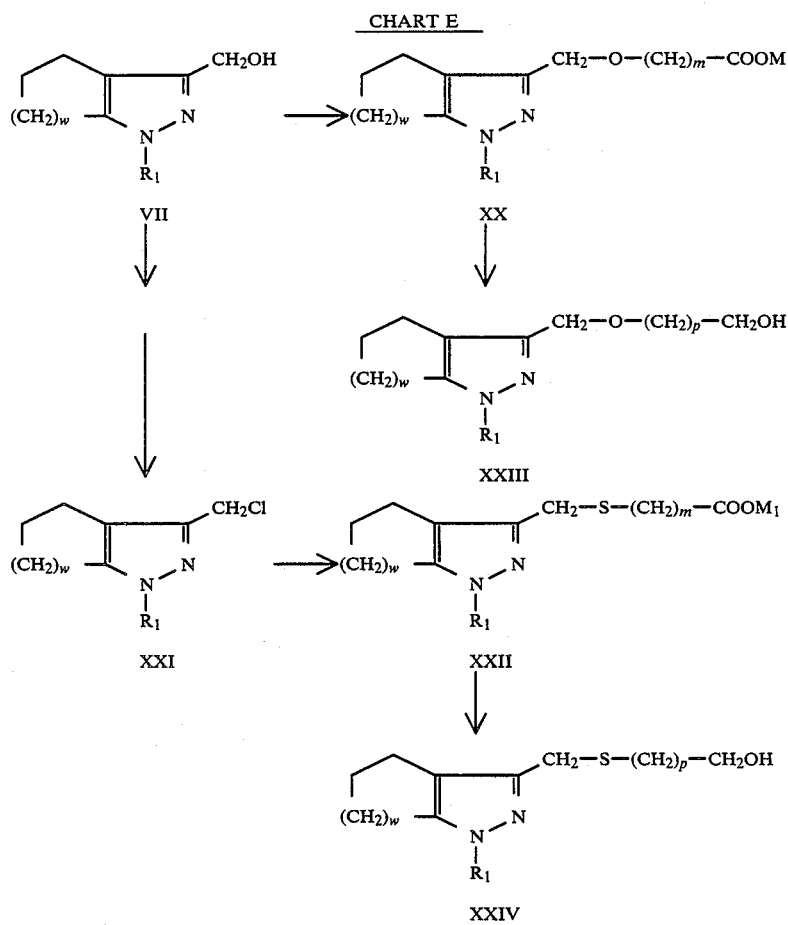

I claim:
1. A compound of formula XXX

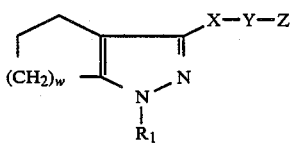   XXX wherein w is 1 or 2;
wherein $R_1$ is:
(a) phenyl,
(b) m- or p-biphenylyl,
(c) benzyl,
(d) benzyl, the aromatic ring of which is substituted with one or two of the following groups, wherein said groups may be the same or different:
(1) —F,
(2) —Cl,
(3) —Br,
(4) —$CF_3$,
(5) —$CH_3$,
(6) —$NO_2$,
(7) —$NHCOR_4$,
(8) —$OR_4$, or
(9) —$SR_4$;

(e) phenyl substituted with one or two of the following groups, wherein said groups may be the same or different:
(1) —F,
(2) —Cl,
(3) —Br,
(4) —$CF_3$,
(5) —$CH_3$,
(6) —$NO_2$,
(7) —$NHCOR_4$,
(8) —$OR_4$, or
(9) —$SR_4$;
wherein $R_4$ is:
(a) —($C_1$-$C_5$)alkyl, or
(b) phenyl;
wherein X is:
(a) cis or trans —CH=CH— or —$CH_2CH_2$— then Y is —$(CH_2)_n$—, and Z is —$COOM_1$, $CH_2OH$, —($C_1$-$C_4$)alkyl or —$CONR_5R_6$;
(b) cis or trans

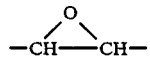

then Y is —$(CH_2)_n$—, and Z is —COOM; or
(c) —$CH_2$— then Y is —O— or —S— and Z is —$(CH_2)_mCOOM_1$ or —$(CH_2)_pCH_2OH$; or
wherein X-Y-Z taken together are:
(a) —CHO, (b)

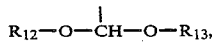

or
(c) —CH$_2$OH when w is 1,
wherein n is 0 to 5;
wherein m is 1 or 2;
wherein p is 2 or 3;
wherein M$_1$ is:
  (a) —H,
  (b) —(C$_1$-C$_4$)alkyl,
  (c) phenyl, or
  (d) phenyl substituted with one or two of the following groups,
wherein said groups may be the same or different:
  (1) —F,
  (2) —Cl,
  (3) —Br,
  (4) —CF$_3$,
  (5) —CH$_3$,
  (6) —NO$_2$,
  (7) —NHCOR$_4$,
  (8) —OR$_4$, or
  (9) —SR$_4$;
wherein R$_5$ is:
  (a) —H,
  (b) —(C$_1$-C$_5$)alkyl,
  (c) phenyl, or
  (d) phenyl substituted with one or two of the following groups,
wherein said groups may be the same or different:
  (1) —F,
  (2) —Cl,
  (3) —Br,
  (4) —CF$_3$,
  (5) —CH$_3$,
  (6) —NO$_2$,
  (7) —NHCOR$_4$, or
  (8) —OR$_4$;
wherein R$_6$ is:
  (a) —H, or
  (b) —(C$_1$-C$_5$)alkyl; or
wherein NR$_5$R$_6$ taken together are:
  (a) pyrrolidino, or
  (b) piperidino;
wherein R$_{12}$ and R$_{13}$ are the same and are:
  (a) —CH$_3$, or
  (b) —C$_2$H$_5$; or
wherein R$_{12}$R$_{13}$ taken together are:
  (a) —(CH$_2$)$_q$—, or
  (b) —CH$_2$C(CH$_3$)$_2$CH$_2$—;
wherein q is 2 or 3;
and pharmaceutically acceptable salts thereof;
and with the following compounds excluded:
(a) when X is

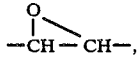

Y is —(CH$_2$)$_n$—, n is 0 to 5, Z is —COOM$_1$, w is 1 or 2 and R$_1$ is phenyl substituted with —SR$_4$;
(b) when X is —CH$_2$CH$_2$—, Y is —(CH$_2$)$_n$—, n is 0 to 5, Z is —(C$_1$-C$_4$)alkyl and w is 2;
(c) when X is —CH$_2$CH$_2$—, Y is —(CH$_2$)$_n$—, n is 0 or 1, Z is —CH$_3$, w is 1 and R$_1$ is phenyl substituted by one or two —F, —Cl or —Br atoms or two —NO$_2$ groups.

2. A compound according to claim 1 wherein w is 1, X is cis or trans —CH=CH—, Y is —(CH$_2$)$_n$—, and Z is —COOM$_1$, —CH$_2$OH or —(C$_1$-C$_4$)alkyl.

3. A compound according to claim 1 wherein w is 1, X is —CH$_2$CH$_2$—, Y is —(CH$_2$)$_n$—, and Z is —COOM$_1$, —CH$_2$OH or —(C$_1$-C$_4$)alkyl.

4. A compound according to claim 1 wherein w is 1, X is —CH$_2$—, Y is —O— or —S—, and Z is —(CH$_2$)$_m$COOM$_1$, or —(CH$_2$)$_p$CH$_2$OH.

5. A compound according to claim 1 wherein w is 1, X-Y-Z taken together are —CH$_2$OH or —CHO.

6. A compound according to claim 1 wherein w is 2, X is cis or trans —CH=CH—, Y is —(CH$_2$)$_n$— and Z is —COOM$_1$, —CH$_2$OH or —(C$_1$-C$_4$)alkyl.

7. A compound according to claim 1 wherein w is 2, X is —CH$_2$CH$_2$—, Y is —(CH$_2$)$_n$— and Z is —COOM$_1$, —CH$_2$OH or —(C$_1$-C$_4$)alkyl.

8. A compound according to claim 1 wherein w is 2, X is —CH$_2$—, Y is —O— or —S—, and Z is —(CH$_2$)$_m$COOM$_1$ or —(CH$_2$)$_p$CH$_2$OH.

9. A compound according to claim 1 wherein w is 2, X-Y-Z taken together are —CHO.

10. A compound according to claim 2 wherein the compound is:
4-Pentenoic acid, 5-(1,4,5,6-tetrahydro-1-phenyl-3-cyclopentapyrazolyl)—, methyl ester, (Z)—, wherein X is cis —CH=CH—, Y is —(CH$_2$)$_n$—, n is 2, Z is —COOM$_1$, M$_1$ is —CH$_3$ and R$_1$ is phenyl;
4-Pentenoic acid, 5-(1,4,5,6-tetrahydro-1-(3-(trifluoromethyl)phenyl)-3-cyclopentapyrazolyl)—, (Z)—, wherein X is cis —CH=CH—, Y is —(CH$_2$)$_n$—, n is 2, Z is —COOM$_1$, M$_1$ is —H and R$_1$ is 3-trifluoromethylphenyl;
5-Hexenoic acid, 6-(1-(4-chlorophenyl)-1,4,5,6-tetrahydro-3-cyclopentapyrazolyl)—, wherein X is cis or trans—CH=CH—, Y is —(CH$_2$)$_n$—, n is 3, Z is —COOM$_1$, M$_1$ is —H and R$_1$ is 4-chlorophenyl;
5-Hexenoic acid, 6-(1,4,5,6-tetrahydro-1-(4-nitrophenyl)-3-cyclopentapyrazolyl)—, methyl ester, (Z)—, wherein X is cis —CH=CH—, Y is —(CH$_2$)$_n$—, n is 3, Z is —COOM$_1$, M$_1$ is —CH$_3$ and R$_1$ is 4-nitrophenyl;
5-Hexenoic acid, 6-(1,4,5,6-tetrahydro-1-(4-nitrophenyl)-3-cyclopentapyrazolyl)—, (Z)—, wherein X is cis —CH=CH—, Y is —(CH$_2$)$_n$—, n is 3, Z is —COOM$_1$, M$_1$ is —H and R$_1$ is 4-nitrophenyl;
5-Hexenoic acid, 6-(1,4,5,6-tetrahydro-1-(4-nitrophenyl)-3-cyclopentapyrazolyl)—, methyl ester, (E)—, wherein X is trans—CH=CH—, Y is —(CH$_2$)$_n$—, n is 3, Z is —COOM$_1$, M$_1$ is —CH$_3$ and R$_1$ is 4-nitrophenyl;
5-Hexenoic acid, 6-(1-(4-fluorophenyl)-1,4,5,6-tetrahydro-3-cyclopentapyrazolyl)—, methyl ester, wherein X is cis or trans—CH=CH—, Y is —(CH$_2$)$_n$—, n is 3, Z is —COOM$_1$, M$_1$ is —CH$_3$ and R$_1$ is 4-fluorophenyl;
5-Hexenoic acid, 6-(1,4,5,6-tetrahydro-1-phenyl-3-cyclopenta-pyrazol-3-yl)—, (E)—, wherein X is trans—CH=CH—, Y is —(CH)$_n$—, n is 3, Z is —COOM$_1$, M$_1$ is —H and R$_1$ is phenyl;
5-Hexenoic acid, 6-(1,4,5,6-tetrahydro-1-(3-trifluoromethyl)phenyl)-3-cyclopentapyrazolyl)-methyl ester, (Z)—, wherein X is cis —CH=CH—, Y is —(CH$_2$)$_n$—, n is 3, Z is —COOM$_1$, M$_1$ is —CH$_3$ and R$_1$ is 3-trifluoromethylphenyl;

7-Octenoic acid, 8-(1,4,5,6-tetrahydro-1-phenyl-3-cyclopentapyrazolyl)—, (E)—, wherein X is trans—CH=CH—, Y is —(CH$_2$)$_n$—, n is 5, Z is —COOM$_1$, M$_1$ is —H and R$_1$ is phenyl;

2-Propenoic acid, 3-(1,4,5,6-tetrahydro-1-phenyl-3-cyclopentapyrazolyl)—, methyl ester, (E)—, wherein X is trans—CH=CH—, Y is —(CH$_2$)$_n$—, n is 0, Z is —COOM$_1$, M$_1$ is —CH$_3$ and R$_1$ is phenyl;

4-Pentenoic acid, 5-(1-(3,4-dichlorophenyl)-1,4,5,6-tetrahydro-3-cyclopentapyrazolyl)—, (E)—, wherein X is trans—CH=CH—, Y is —(CH$_2$)$_n$—, n is 2, Z is —COOM$_1$, M$_1$ is —H and R$_1$ is 3,4-dichlorophenyl;

4-Pentenoic acid, 5-(1-(3,4-dichlorophenyl)-1,4,5,6-tetrahydro-3-cyclopentapyrazolyl)—, (Z)—, wherein X is cis—CH=CH—, Y is —(CH$_2$)$_n$—, n is 2, Z is —COOM$_1$, M$_1$ is —H and R$_1$ is 3,4-dichlorophenyl;

4-Pentenoic acid, 5-(1-(3,4-dichlorophenyl)-1,4,5,6-tetrahydro-3-cyclopentapyrazolyl)—, methyl ester, (E)—, wherein X is trans—CH=CH—, Y is —(CH$_2$)$_n$—, n is 2, Z is —COOM$_1$, M$_1$ is —CH$_3$ and R$_1$ is 3,4-dichlorophenyl;

4-Pentenoic acid, 5-(1-(3,4-dichlorophenyl)-1,4,5,6-tetrahydro-3-cyclopentapyrazolyl)—, methyl ester, (Z)—, wherein X is cis—CH=CH—, Y is —(CH$_2$)$_n$—, n is 2, Z is —COOM$_1$, M$_1$ is —CH$_3$ and R$_1$ is 3,4-dichlorophenyl;

2-Propenoic acid, 3-(1,4,5,6-tetrahydro-1-phenyl-3-cyclopentapyrazolyl)—, (E)—, wherein X is trans—CH=CH—, Y is —(CH$_2$)$_n$—, n is 0, Z is —COOM$_1$, M$_1$ is —H and R is phenyl;

4-Pentenoic acid, 5-(1,4,5,6-tetahydro-1-phenyl-3-cyclopentapyrazolyl)—, (E)—, wherein X is trans—CH=CH—, Y is —(CH$_2$)$_n$—, n is 2, Z is —COOM$_1$, M$_1$ is —H and R$_1$ is phenyl;

5-Hexenoic acid, 6-(1,4,5,6-tetrahydro-1-(4-nitrophenyl)-3-cyclopentapyrazolyl)—, (E)—, wherein X is trans—CH=CH—, Y is —(CH$_2$)$_n$—, n is 3, Z is —COOM$_1$, M$_1$ is —H and R$_1$ is 4-nitrophenyl;

5-Hexenoic acid, 6-(1-(3,4-dichlorophenyl)-1,4,5,6-tetrahydro-3-cyclopentapyrazolyl)—, (E)—, wherein X is trans—CH=C—, Y is —(CH$_2$)$_n$—, n is 3, Z is —COOM$_1$, M$_1$ is —H and R$_1$ is 3,4-dichlorophenyl;

5-Hexenoic acid, 6-(1-(3,4-dichlorophenyl)-1,4,5,6-tetrahydro-3-cyclopentapyrazolyl)—, (Z)—, wherein X is cis—CH=CH—, Y is —(CH$_2$)$_n$—, n is 3, Z is —COOM$_1$, M$_1$ is —H and R$_1$ is 3,4-dichlorophenyl;

5-Hexenoic acid, 6-(1-(4-fluorophenyl)-1,4,5,6-tetrahydro-3-cyclopentapyrazolyl)—, (E)—, wherein X is trans—CH=CH—, Y is —(CH$_2$)$_n$—, n is 3, Z is —COOM$_1$, M$_1$ is —H and R$_1$ is 4-fluorophenyl;

5-Hexenoic acid, 6-(1,4,5,6-tetrahydro-1-(4-methoxyphenyl)-3-cyclopentapyrazolyl—, (E)—, wherein X is trans—CH=CH—, Y is —(CH$_2$)$_n$—, n is 3, Z is —COOM$_1$, M$_1$ is —H and R$_1$ is 4-methoxyphenyl;

5-Hexenoic acid, 6-(1-(3,4-dichlorophenyl)-1,4,5,6-tetrahydro-3-cyclopentapyrazolyl)—, methyl ester, (Z)—, wherein X is cis—CH=CH—, Y is —(CH$_2$)$_n$—, n is 3, Z is —COOM$_1$, M$_1$ is —CH$_3$ and R$_1$ is 3,4-dichlorophenyl;

5-Hexenoic acid, 6-(1-(3,4-dichlorophenyl)-1,4,5,6-tetrahydro-3-cyclopentapyrazolyl)—, methyl ester, (E)—, wherein X is trans—CH=CH—, Y is —(CH$_2$)$_n$—, n is 3, Z is —COOM$_1$, M$_1$ is —CH$_3$ and R$_1$ is 3,4-dichlorophenyl;

Cyclopentapyrazole, 1,4,5,6-tetrahydro-3-(1-heptenyl)-1-phenyl—, wherein X is cis or trans—CH=CH—, Y is —(CH$_2$)$_n$—, n is 4, Z is —CH$_3$ and R$_1$ is phenyl;

5-Hexen-1-ol, 6-(1-(4-bromophenyl)-1,4,5,6-tetrahydro-3-cyclopentapyrazolyl)—, (Z)—, wherein X is cis—CH=CH—, Y is —(CH$_2$)$_n$—, n is 3, Z is —CH$_2$OH and R$_1$ is 4-bromophenyl;

5-Hexen-1-ol, 6-(1-(4-bromophenyl)-1,4,5,6-tetrahydro-3-cyclopentapyrazolyl)—, (E)—, wherein X is trans—CH=CH—, Y is —(CH$_2$)$_n$—, n is 3, Z is —CH$_2$OH and R$_1$ is 4-bromophenyl; or, 5-Hexenoic acid, 6-(1,4,5,6-tetrahydro-1-(4-methoxyphenyl)-3-cyclopentapyrazolyl)—, (Z)—, wherein X is cis—CH=CH—, Y is —(CH$_2$)$_n$—, n is 3, Z is —COOM$_1$, M$_1$ is —H and R$_1$ is 4-methoxyphenyl.

11. A compound according to claim 3 wherein the compound is:

3-Cyclopentapyrazolehexanoic acid, 1,4,5,6-tetrahydro-1-(4-nitrophenyl)—, methyl ester, wherein X is —CH$_2$CH$_2$—, Y is —(CH$_2$)$_n$—, n is 3, Z is —COOM$_1$, M$_1$ is —CH$_3$ and R$_1$ is 4-nitrophenyl;

3-Cyclopentapyrazolehexanoic acid, 1,4,5,6-tetrahydro-1-(4-nitrophenyl)—, wherein X is —CH$_2$CH$_2$—, Y is —(CH$_2$)$_n$—, n is 3, Z is —COOM$_1$, M$_1$ is —H and R$_1$ is 4-nitrophenyl;

3-Cyclopentapyrazolehexanoic acid, 1,4,5,6-tetrahydro-1-(3-(trifluoromethyl)phenyl)—, wherein X is —CH$_2$CH$_2$—, Y is —(CH$_2$)$_n$—, n is 3, Z is —COOM$_1$, M$_1$ is —H and R$_1$ is 3-trifluoromethylphenyl;

3-Cyclopentapyrazoleoctanoic acid, 1,4,5,6-tetrahydro-1-phenyl—, wherein X is —CH$_2$CH$_2$—, Y is —(CH$_2$)$_n$—, n is 5, Z is —COOM$_1$, M$_1$ is —H and R$_1$ is phenyl;

3-Cyclopentapyrazolepentanoic acid, 1-(3,4-dichlorophenyl)-1,4,5,6-tetrahydro—, wherein X is —CH$_2$CH$_2$—, Y is —(CH$_2$)$_n$—, n is 2, Z is —COOM$_1$, M$_1$ is —H and R$_1$ is 3,4-dichlorophenyl;

3-Cyclopentapyrazolehexanoic acid, 1-(3,4-dichlorophenyl)-1,4,5,6-tetrahydro—, wherein X is —CH$_2$CH$_2$—, Y is —(CH$_2$)$_n$—, n is 3, Z is —COOM$_1$, M$_1$ is —H and R$_1$ is 3,4-dichlorophenyl;

3-Cyclopentapyrazolepentanoic acid, 1,4,5,6-tetrahydro-1-phenyl—, wherein X is —CH$_2$CH$_2$—, Y is —(CH$_2$)$_n$—, n is 2, Z is —COOM$_1$, M$_1$ is —H and R$_1$ is phenyl;

3-Cyclopentapyrazolehexanoic acid, 1,4,5,6-tetrahydro-1-phenyl—, wherein X is —CH$_2$CH$_2$—, Y is —(CH$_2$)$_n$—, n is 3, Z is —COOM$_1$, M$_1$ is —H and R$_1$ is phenyl;

3-Cyclopentapyrazolehexanoic acid, 1-(4-chlorophenyl)-1,4,5,6-tetrahydro—, methyl ester, wherein X is —CH$_2$CH$_2$—, Y is —(CH$_2$)$_n$—, n is 3, Z is —COOM$_1$, M$_1$ is —CH$_3$ and R$_1$ is 4-chlorophenyl;

3-Cyclopentapyrazolehexanoic acid, 1-(4-chlorophenyl)-1,4,5,6-tetrahydro—, wherein X is —CH$_2$CH$_2$—, Y is —(CH$_2$)$_n$—, n is 3, Z is —COOM$_1$, M$_1$ is —H and R$_1$ is 4-chlorophenyl;

3-Cyclopentapyrazolehexanoic acid, 1-(4-fluorophenyl)-1,4,5,6-tetrahydro—, wherein X is —CH$_2$CH$_2$—, Y is —(CH$_2$)$_n$—, n is 3, Z is —COOM$_1$, M$_1$ is —H and R$_1$ is 4-fluorophenyl;

3-Cyclopentapyrazolehexanol, 1-(4-fluorophenyl)-1,4,5,6-tetrahydro—, wherein X is —CH$_2$CH$_2$—, Y is —(CH$_2$)$_n$—, n is 3, Z is —CH$_2$OH and R$_1$ is 4-fluorophenyl;

3-Cyclopentapyrazolehexanol, 1,4,5,6-tetrahydro-1-(4-nitro-phenyl)—, wherein X is —CH$_2$CH$_2$—, Y is —(CH$_2$)$_n$—, n is 3, Z is —CH$_2$OH and R$_1$ is 4-nitrophenyl;

3-Cyclopentapyrazolehexanol, 1-(4-bromophenyl)-1,4,5,6-tetrahydro—, wherein X is —$CH_2CH_2$—, Y is —$(CH_2)_n$—, n is 3, Z is —$CH_2OH$ and $R_1$ is 4-bromophenyl; or Cyclopentapyrazole, 3-heptyl-1,4,5,6-tetrahydro-1-phenyl—, wherein X is —$CH_2CH_2$—, Y is —$(CH_2)_n$—, n is 4, Z is —$CH_3$ and $R_1$ is phenyl.

12. A compound according to claim 4 wherein the compound is:

Acetic acid, ((1-(4-chlorophenyl)-1,4,5,6-tetrahydro-3-cyclopentapyrazolyl)methoxy)—, wherein X is —$CH_2$—, Y is —O—, Z is —$(CH_2)_mCOOM_1$, m is 1, $M_1$ is —H and $R_1$ is 4-chlorophenyl;

Propanoic acid, 3-(((1,4,5,6-tetrahydro-1-phenyl-3-cyclopentapyrazolyl)methyl)thio)—, wherein X is —$CH_2$—, Y is —S—, Z is —$(CH_2)_mCOOM_1$, m is 2, $M_1$ is —H and $R_1$ is phenyl;

1-Propanol, 3-((1,4,5,6-tetrahydro-1-(3-(trifluoromethyl)phenyl)-3-cyclopentapyrazolyl)methoxy)—, wherein X is —$CH_2$—, Y is —O—, Z is —$(CH_2)_pCH_2OH$, p is 2 and $R_1$ is 3-trifluoromethylphenyl; or Propanoic acid, 3-((1,4,5,6-tetrahydro-1-(3-(trifluoromethyl)phenyl)-3-cyclopentapyrazolyl)methoxy)—, wherein X is —$CH_2$—, Y is —O—, Z is —$(CH_2)_mCOOM_1$, m is 2, $M_1$ is —H and $R_1$ is 3-trifluoromethylphenyl.

13. A compound according to claim 5 wherein the compound is:

3-Cyclopentapyrazolemethanol, 1,4,5,6-tetrahydro-1-phenyl—, wherein X-Y-Z taken together are —$CH_2OH$ and $R_1$ is phenyl;

3-Cyclopentapyrazolemethanol, 1-(4-fluorophenyl)-1,4,5,6-tetrahydro—, wherein X-Y-Z taken together are —$CH_2OH$ and $R_1$ is 4-fluorophenyl;

3-Cyclopentapyrazolecarboxaldehyde, 1-(4-chlorophenyl)-1,4,5,6-tetrahydro—, wherein X-Y-Z taken together are —CHO and R is 4-chlorophenyl;

3-Cyclopentapyrazolecarboxaldehyde, 1,4,5,6-tetrahydro-1-(4-nitrophenyl)—, wherein X-Y-Z taken together are —CHO and $R_1$ is 4-nitrophenyl;

3-Cyclopentapyrazolecarboxaldehyde, 1-(3,4-dichlorophenyl)-1,4,5,6-tetrahydro—, wherein X-Y-Z taken together are —CHO and $R_1$ is 3,4-dichlorophenyl;

3-Cyclopentapyrazolecarboxaldehyde, 1-(4-bromophenyl)-1,4,5,6-tetrahydro—, wherein X-Y-Z taken together are —CHO and $R_1$ is 4-bromophenyl; or 3-Cyclopentapyrazolecarboxaldehyde, 1,4,5,6-tetrahydro-1-(3-(trifluoromethyl)phenyl)—, wherein X-Y-Z taken together are —CHO and $R_1$ is 3-trifluoromethylphenyl.

14. A compound according to claim 6 wherein the compound is:

5-Hexenoic acid, 6-(1-fluorophenyl)-4,5,6,7-tetrahydro-1H-indazol-3-yl)—, (Z)—, wherein X is cis—CH=CH—, Y is —$(CH_2)_n$—, n is 3, Z is —$COOM_1$, $M_1$ is —H and $R_1$ is 4-fluorophenyl;

4-Pentenoic acid, 5-(4,5,6,7-tetrahydro-1-phenyl-1H-indazol-3-yl)—, (E)—, wherein X is trans—CH=CH—, Y is —$(CH_2)_n$—, n is 2, Z is —$COOM_1$, $M_1$ is —H and $R_1$ is phenyl;

5-Hexenoic acid, 6-(4,5,6,7-tetrahydro-1-(4-nitrophenyl)-1H-indazol-3-yl)—, (Z)—, wherein X is cis—CH=CH—, Y is —$(CH_2)_n$—, n is 3, Z is —$COOM_1$, $M_1$ is —H and $R_1$ is 4-nitrophenyl;

5-Hexenoic acid, 6-(4,5,6,7-tetrahydro-1-(4-nitrophenyl)-1H-indazol-3-yl)—, methyl ester, (E)—, wherein X is trans—CH=CH—, Y is —$(CH_2)_n$—, n is 3, Z is —$COOM_1$, $M_1$ is —$CH_3$ and $R_1$ is 4-nitrophenyl;

5-Hexenoic acid, 6-(4,5,6,7-tetrahydro-1-(4-nitrophenyl)-1H-indazol-3-yl)—, methyl ester, (Z)—, wherein X is cis—CH=CH—, Y is —$(CH_2)_n$—, n is 3, Z is —$COOM_1$, $M_1$ is —$CH_3$ and $R_1$ is 4-nitrophenyl;

5-Hexenoic acid, 6-(4,5,6,7-tetrahydro-1-(3-(trifluoromethyl)phenyl)-1H-indazol-3-yl)—, (Z)—, wherein X is cis—CH=CH—, Y is —$(CH_2)_n$—, n is 3, Z is —$COOM_1$, $M_1$ is —H and $R_1$ is 3-trifluoromethylphenyl;

5-Hexenoic acid, 6-(4,5,6,7-tetrahydro-1-(3-(trifluoromethyl)phenyl)-1H-indazol-3-yl)—, (E)—, wherein X is trans—CH=CH—, Y is —$(CH_2)_n$—, n is 3, Z is —$COOM_1$, $M_1$ is —H and $R_1$ is 3-trifluoromethylphenyl; or 5-Hexenoic acid, 6-(4,5,6,7-tetrahydro-1-phenyl-1H-indazol-3-yl)—, (Z)—, wherein X is cis—CH=CH—, Y is —$(CH_2)_n$—, n is 3, Z is —$COOM_1$, $M_1$ is —H and $R_1$ is phenyl.

15. A compound according to claim 7 wherein the compound is:

1H-Indazole-3-propionic acid, 1-(4-fluorophenyl)-4,5,6,7-tetrahydro—, wherein X is —$CH_2CH_2$—, Y is —$(CH_2)_n$—, n is 0, Z is —$COOM_1$, $M_1$ is —H and $R_1$ is 4-fluorophenyl;

1H-Indazole-3-hexanoic acid, 4,5,6,7-tetrahydro-1-(4-nitrophenyl)—, methyl ester, wherein X is —$CH_2CH_2$—, Y is —$(CH_2)_n$—, n is 3, Z is —$COOM_1$, $M_1$ is —$CH_3$ and $R_1$ is 4-nitrophenyl;

1H-Indazole-3-hexanoic acid, 4,5,6,7-tetrahydro-1-(4-nitrophenyl)—, wherein X is —$CH_2CH_2$—, Y is —$(CH_2)_n$—, n is 3, Z is —$COOM_1$, $M_1$ is —H and $R_1$ is 4-nitrophenyl;

1H-Indazole-3-pentanoic acid, 4,5,6,7-tetrahydro-1-(3-(trifluoromethyl)phenyl)—, wherein X is —$CH_2CH_2$—, Y is —$(CH_2)_n$—, n is 2, Z is —$COOM_1$, $M_1$ is —H and $R_1$ is 3-trifluoromethylphenyl; or 1H-Indazole-3-hexanoic acid, 1-(4-fluorophenyl)-4,5,6,7-tetrahydro—, wherein X is —$CH_2CH_2$—, Y is —$(CH_2)_n$—, n is 3, Z is —$COOM_1$, $M_1$ is —H and $R_1$ is 4-fluorophenyl.

16. A compound according to claim 8 wherein the compound is:

Acetic acid, ((1-(4-bromophenyl)-4,5,6,7-tetrahydro-1H-indazol-3-yl)methoxy)—, wherein X is —$CH_2$—, Y is —O—, Z is —$(CH_2)_mCOOM_1$, m is 1, $M_1$ is —H and $R_1$ is 4-bromophenyl;

Acetic acid, ((4,5,6,7-tetrahydro-1-phenyl-1H-indazol-3-yl)methyl)thio)—, wherein X is —$CH_2$—, Y is —S—, Z is —$(CH_2)_mCOOM_1$, m is 1, $M_1$ is —H and $R_1$ is phenyl;

Acetic acid, ((1-(4-chlorophenyl)-4,5,6,7-tetrahydro-1H-indazol-3-yl)methoxy)—, ethyl ester, wherein X is —$CH_2$—, Y is —O—, Z is —$(CH_2)_mCOOM_1$, m is 1, $M_1$ is —$CH_2CH_3$ and $R_1$ is 4-chlorophenyl; or Propanoic acid, 3-(((4,5,6,7-tetrahydro-1-phenyl-1H-indazol-3-yl)methyl)thio)—, wherein X is —$CH_2$—, Y is —S—, Z is —$(CH_2)_mCOOM_1$, m is 2, $M_1$ is —H and $R_1$ is phenyl.

17. A compound according to claim 9 wherein the compound is:

1H-Indazole-3-carboxaldehyde, 4,5,6,7-tetrahydro-1-phenyl—, wherein X-Y-Z taken together are —CHO and $R_1$ is phenyl;

1H-Indazole-3-carboxaldehyde, 1-(4-bromophenyl)-4,5,6,7-tetrahydro—, wherein X-Y-Z taken together are —CHO and $R_1$ is 4-bromophenyl; or, 1H-Indazole-3-carboxaldehyde, 4,5,6,7-tetrahydro-1-(3-(trifluoromethyl)phenyl)—, wherein X-Y-Z taken together are —CHO and $R_1$ is 3-trifluoromethylphenyl.

18. A compound according to claim 1 wherein the compound is:

4-Pentenoic acid, 5-(1-(3,4-dichlorophenyl)-1,4,5,6-tetrahydro-3-cyclopentapyrazolyl)—, (Z)—;

Propanoic acid, 3-(((4,5,6,7-tetrahydro-1-phenyl-1H-indazol-3-yl)methyl)thio)—;

5-Hexenoic acid, 6-(1,4,5,6-tetrahydro-1-(4-nitrophenyl)-3-cyclopentapyrazolyl)—, (E)—; or 1H-Indazole-3-carboxaldehyde, 1-(4-bromophenyl)-4,5,6,7-tetrahydro—.

19. A method of treating allergies in a patient in need thereof which comprises administering to said patient a compound of formula XXX

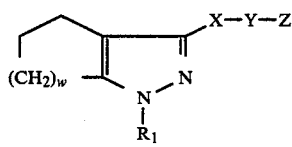

XXX wherein w is 1 or 2;
wherein $R_1$ is:
(a) phenyl,
(b) m- or p-biphenylyl,
(c) benzyl,
(d) benzyl, the aromatic ring of which is substituted with one or two of the following groups, wherein said groups may be the same or different;
(1) —F,
(2) —Cl,
(3) —Br,
(4) —CF$_3$,
(5) —CH$_3$,
(6) —NO$_2$,
(7) —NHCOR$_4$,
(8) —OR$_4$, or
(9) —SR$_4$;
(e) phenyl substituted with one or two of the following groups, wherein said groups may be the same or different:
(1) —F,
(2) —Cl,
(3) —Br,
(4) —CF$_3$,
(5) —CH$_3$,
(6) —NO$_2$,
(7) —NHCOR$_4$,
(8) —OR$_4$, or
(9) —SR$_4$;
wherein $R_4$ is:
(a) —(C$_1$–C$_5$) alkyl, or
(b) phenyl;
wherein X is:
(a) cis or trans —CH=CH— or —CH$_2$CH$_2$— then Y is —(CH$_2$)$_n$—, and Z is —COOM$_1$, CH$_2$OH, —(C$_1$–C$_4$)alkyl or —CONR$_5$R$_6$;
(b) cis or trans

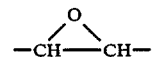

then Y is —(CH$_2$)$_n$—, and Z is —COOM; or
(c) —CH$_2$— then Y is —O— or —S— and Z is —(CH$_2$)$_m$COOM$_1$ or —(CH$_2$)$_p$CH$_2$OH; or
wherein X-Y-Z taken together are:
(a) —CHO,
(b)

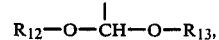

or
(c) is —CH$_2$OH when w is 1,
wherein n is 0 to 5;
wherein m is 1 or 2;
wherein p is 2 or 3;
wherein M$_1$ is:
(a) —H,
(b) —(C$_1$–C$_4$) alkyl,
(c) phenyl, or
(d) phenyl substituted with one or two of the following groups,
wherein said groups may be the same or different:
(1) —F,
(2) —Cl,
(3) —Br,
(4) —CF$_3$,
(5) —CH$_3$,
(6) —NO$_2$,
(7) —NHCOR$_4$,
(8) —OR$_4$, or
(9) —SR$_4$;
wherein R$_5$ is:
(a) —H,
(b) —(C$_1$–C$_5$) alkyl,
(c) phenyl, or
(d) phenyl substituted with one or two of the following groups,
wherein said groups may be the same or different:
(1) —F,
(2) —Cl,
(3) —Br,
(4) —CF$_3$,
(5) —CH$_3$,
(6) —NO$_2$,
(7) —NHCOR$_4$, or
(8) —OR$_4$;
wherein R$_6$ is:
(a) —H, or
(b) —(C$_1$–C$_5$) alkyl; or
wherein NR$_5$R$_6$ taken together are:
(a) pyrrolidino, or
(b) piperidino;
wherein R$_{12}$ and R$_{13}$ are the same and are:
(a) —CH$_3$, or
(b) —C$_2$H$_5$; or
wherein R$_{12}$R$_{13}$ taken together are:
(a) —(CH$_2$)$_q$—, or
(b) —CH$_2$C(CH$_3$)$_2$CH$_2$—;
wherein q is 2 or 3;
and pharmaceutically acceptable salts thereof;
and with the following compounds excluded:

(a) when X is cis—CH═CH—, Y is —(CH$_2$)$_n$—, n is 3, Z is —COOM$_1$, M$_1$ is —H, w is 1 and R$_1$ is 4-methoxyphenyl;

(b) when X-Y-Z taken together are —CH$_2$OH, R$_1$ is 3,4-dichlorophenyl and w is 1; and (c) when X is trans—CH═CH—, Y is —(CH$_2$)$_n$—, n is 2, Z is —COOM$_1$, M$_1$ is —CH$_3$, R$_1$ is 3,4-dichlorophenyl and w is 1.

20. A method of treating an inflammatory disease in a patient in need thereof which comprises administering to said patient one of the following compounds:

Cyclopentapyrazole, 3-heptyl-1,4,5,6-tetrahydro-1-phenyl—;

Acetic acid, ((1-(4-chlorophenyl)-1,4,5,6-tetrahydro-3-cyclopentapyrazolyl)methoxy)—;

Propanoic acid, 3-(((1,4,5,6-tetrahydro-1-phenyl-3-cyclopentapyrazolyl)methyl)thio)—;

5-Hexenoic acid, 6-(1-(4-fluorophenyl)-1,4,5,6-tetrahydro-3-cyclopentapyrazolyl)—, methyl ester;

5-Hexenoic acid, 6-(1,4,5,6-tetrahydro-1-(4-methoxyphenyl)-3-cyclopentapyrazolyl)—, (E)—;

5-Hexenoic acid, 6-(1-(3,4-dichlorophenyl)-1,4,5,6-tetrahydro-3-cyclopentapyrazolyl)—, methyl ester, (Z)—;

5-Hexenoic acid, 6-(1-(3,4-dichlorophenyl)-1,4,5,6-tetrahydro-3-cyclopentapyrazolyl)—, methyl ester, (E)—;

4-Pentenoic acid, 5-(1-(3,4-dichlorophenyl)-1,4,5,6-tetrahydro-3-cyclopentapyrazolyl)—, methyl ester, (Z)—;

4-Pentenoic acid, 5-(1-(3,4-dichlorophenyl)-1,4,5,6-tetrahydro-3-cyclopentapyrazolyl)—, methyl ester, (E)—;

4-Pentenoic acid, 5-(1-(3,4-dichlorophenyl)-1,4,5,6-tetrahydro-3-cyclopentapyrazolyl)—, (Z)—;

3-Cyclopentapyrazolepentanoic acid, 1-(3,4-dichlorophenyl)-1,4,5,6-tetrahydro—;

1-Propanol, 3-((1,4,5,6-tetrahydro-1-(3-(trifluoromethyl)phenyl)-3-cyclopentapyrazolyl)methoxy)—;

Propanoic acid, 3-((1,4,5,6-tetrahydro-1-(3-(trifluoromethyl)phenyl)-3-cyclopentapyrazolyl)methoxy)—;

5-Hexenoic acid, 6-(1-fluorophenyl)-4,5,6,7-tetrahydro-1H-indazol-3-yl)—, (Z)—;

1H-Indazole-3-carboxaldehyde, 4,5,6,7-tetrahydro-1-phenyl;

4-Pentenoic acid, 5-(4,5,6,7-tetrahydro-1-phenyl-1H-indazol-3-yl)—, (E)—;

Acetic acid, (((4,5,6,7-tetrahydro-1-phenyl-1H-indazol-3-yl)methyl)thio);

Acetic acid, ((1-(4-bromophenyl)-4,5,6,7-tetrahydro-1H-indazol-3-yl)methoxy)—;

Propanoic acid, 3-((4,5,6,7-tetrahydro-1-phenyl-1H-indazol-3-yl)methyl)thio)—;

1H-Indazole-3-hexanoic acid, 1-(4-fluorophenyl)-4,5,6,7-tetrahydro—;

5-Hexenoic acid, 6-(4,5,6,7-tetrahydro-1-(3-(trifluoromethyl)phenyl)-1H-indazol-3-yl)—, (Z)—;

5-Hexenoic acid, 6-(4,5,6,7-tetrahydro-1-(3-(trifluoromethyl)phenyl)-1H-indazol-3-yl)—, (E)—; and 1H-Indazole-3-pentanoic acid, 4,5,6,7-tetrahydro-1-(3-(trifluoromethyl)phenyl)—.

* * * * *